US007271245B2

(12) United States Patent  
Felding-Habermann et al.

(10) Patent No.: US 7,271,245 B2
(45) Date of Patent: Sep. 18, 2007

(54) METHODS AND COMPOSITIONS FOR INHIBITION OF METASTASIS

(75) Inventors: Brunhilde Felding-Habermann, San Diego, CA (US); Kim D. Janda, La Jolla, CA (US); Alan Saven, Del Mar, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 11/056,825

(22) Filed: Feb. 11, 2005

(65) Prior Publication Data

US 2005/0255109 A1 Nov. 17, 2005

Related U.S. Application Data

(60) Provisional application No. 60/544,807, filed on Feb. 13, 2004, provisional application No. 60/626,726, filed on Nov. 10, 2004.

(51) Int. Cl.
*C07K 1/00* (2006.01)
*C07K 16/00* (2006.01)
*A61K 39/395* (2006.01)
*A61K 39/00* (2006.01)

(52) U.S. Cl. ............... 530/350; 530/387.1; 424/130.1; 424/135.1; 424/141.1

(58) Field of Classification Search .................... None
See application file for complete search history.

(56) References Cited

U.S. PATENT DOCUMENTS

| | | | | |
|---|---|---|---|---|
| 5,502,167 A | * | 3/1996 | Waldmann et al. | 530/387.3 |
| 5,578,704 A | | 11/1996 | Kim et al. | 530/388.22 |
| 5,590,079 A | | 12/1996 | Lee et al. | 365/201 |
| 5,652,109 A | | 7/1997 | Kim et al. | 435/7.1 |
| 5,652,110 A | | 7/1997 | Kim et al. | 435/7.1 |
| 5,753,230 A | | 5/1998 | Brooks et al. | 424/158.1 |
| 6,171,588 B1 | | 1/2001 | Carron et al. | 424/143.1 |
| 6,193,968 B1 | | 2/2001 | Carron et al. | 424/155.1 |
| 6,359,126 B1 | | 3/2002 | Kim et al. | 536/23.53 |
| 6,369,204 B1 | | 4/2002 | Kim et al. | 530/388.22 |
| 6,406,693 B1 | | 6/2002 | Thorpe et al. | 424/130.1 |
| 6,531,580 B1 | | 3/2003 | Huse et al. | 530/388.22 |
| 6,596,850 B1 | | 7/2003 | Huse | 530/387.3 |
| 2002/0025510 A1 | | 2/2002 | Strongin et al. | 435/4 |
| 2003/0129188 A1 | | 7/2003 | Barbas et al. | 424/144.1 |
| 2003/0166872 A1 | | 9/2003 | Huse et al. | 530/388.22 |
| 2004/0001835 A1 | | 1/2004 | Woessner et al. | 424/155.1 |
| 2004/0005550 A1 | | 1/2004 | Shattil et al. | 435/5 |

OTHER PUBLICATIONS

Zheng et al., cancer research, vol. 59, p. 1655-1664, 1999.*
Lanza et al., Blood Cells, Molecules and Disease, vol. 23, p. 230-241, 1997.*
Tatiana et al., Experimental Cell Research vol. 254, p. 299-308, 2000.*
Felding-Habermann et al., Clinical & Experimental Metastasis, vol. 19, p. 427-436, 2002.*
Yun et al., Cancer Research, vol. 56, p. 3103-3111, 1996.*
Byzova et al., Experimental Cell Research vol. 254, p. 299-308, 2000.*
McNeel et al., "Phase I Trial of a Monoclonal Antibody Specific for $\alpha v \beta 3$ Integrin (MEDI-522) in Patients with Advanced Malignancies, Including an Assessment of Effect of Tumor Perfusion," *Clin. Cancer Res.*, 2005, 11(21), 7851-7860.
Vacca et al., "$\alpha v \beta 3$ Integrin Engagement Modulates Cell Adhesion, Proliferation, and Protease Secretion in Human Lymphoid Tumor Cells," *Exp. Hematol.*, 2001, 29(8), 993-1003.
Al Hajj, *Proc. Natl. Acad. Sci. U.S.A*, "Prospective identification of tumorigenic breast cancer cells," 100: 3983-3988, 2003.
Ali, "Medicial Management of Bone Metastases," *Clin. Orthop.*, S132-S137, 2003.
Amirkhosravi et al., "Inhibition of tumor cell-induced platelet aggregation and lung metastasis by the oral GpIIb/IIIa antagonist XV454," *Thromb. Haemost.*, 90: 549-554, 2003.
Asano et al., "Masking of Phosphatidylserine Inhibits Apoptotic Cell Engulfment and Induces Autoantibody Production In Mice," *J Exp Med*, 200:459-467, 2004.
Bakewell et al., "Platelet and osteoclast $B_3$ integrins are critical for bone metastasis," *Proc. Natl. Acad. Sci. U.S.A*, 100: 14205-14210, 2003.
Beglova et al., "Cysteine-rich module structure reveals a fulcrum for integrin rearrangement upon activation," *Nat. Struct. Biol.* 9: 282-287, 2002.
Biggerstaff et al., "Soluble fibrin augments platelet/tumor cell adherence in vitro and in vivo, and enhances experimental metastasis," *Clin.Exp.Metastasis*, 17: 723-730, 1999.
Bogenrieder et al., "Axis of evil: molecular mechanisms of cancer metastasis," *Oncogene* 22: 6524-6536, 2003.
Bougie et al., "Acute thrombocytopenia after treatment with tirofiban or eptifibatide is associated with antibodies specific for ligand-occupied CPIIb/IIIa," *Blood*, 100:2071-2076, 2002.
Brooks et al., "Integrin $\alpha_v \beta_3$ Antagonists Promote Tumor Regression by Inducing Apoptosis of Angiogenic Blood Vessels," *Cell*, 79: 1157-1164, 1994.
Brooks et al., "Requirement of Vascular Integrin $\alpha_v \beta_3$ for Angiogenesis," *Science*, 264: 569-571, 1994.
Buckley et al., "RGD peptides induce apoptosis by direct caspase-3 activation," *Nature* 397: 534-539, 1999.
Calzada et al., "Agonist-specific Structural Rearrangements of Integrin $\alpha_{IIb}\beta_3$," *J. Biol. Chem.* 277: 39899-39908, 2002.
Chen et al., "MicroPET and Autoradiographic Imaging of Breast Cancer $\alpha_v$-Integrin Expression Using $^{18}$F- and $^{64}$Cu-Labeled RGD Peptide," *Bioconjug. Chem.*, 15: 41-49, 2004.
Chu and Ng, "Interaction of West Nile Virus with $\alpha_v \beta_3$ Integrin Mediates Virus Entry into Cells," *Journal of Biol. Chem.*, 279:54533-54541, 2004.

(Continued)

*Primary Examiner*—Shanon Foley
*Assistant Examiner*—Lei Yao
(74) *Attorney, Agent, or Firm*—Woodcock Washburn LLP

(57) ABSTRACT

This invention generally relates to methods of producing an antibody phage population having affinity for a tumor cell target expressing a metastatic phenotype. The invention further relates to antibody compositions that specifically bind to a cell surface receptor on the metastatic cell.

8 Claims, 13 Drawing Sheets

OTHER PUBLICATIONS

Chung et al., "Integrin $\alpha_{IIb}\beta_3$-specific synthetic human monoclonal antibodies and HCDR3 peptides that potently inhibit platelet aggregation," *FASEB Journal*, 18:361-363, 2004.

Coelho et al., "RGD- and MLD-disintegrins, jarastatin and EC3, activated integrin-mediated signaling modulating the human neutrophils chemotaxis, apoptosis and IL-8 gene expression," *Experimental Cell Research*, 292:371-384, 2004.

Collins et al., "Identification and isolation of human prostate epithelial stem cells based on $\alpha_2\beta_1$-integrin expression," *J. Cell Sci.*, 114: 3865-3872, 2001.

Ding et al., "Promotion of Malignant Astrocytoma Cell Migration by Osteopontin Expressed in the Normal Brain: Differences in Itegrin Signaling during Cell Adhesion to Osteopontin Versus Vitronectin," *Cancer Res.*, 62: 5336-5343, 2002.

Evans et al., "A tumor-associated $\beta 1$ integrin mutation that abrogates epithelial differentiation control," *J. Cell Biol.*, 160: 589-596, 2003.

Felding-Habermann et al., "Role of $\beta_3$ Integrins in Melanoma Cell Adhesion to Activated Platelets under Flow," *J. Biol. Chem.* 271: 5892-5900, 1996.

Felding-Habermann, B., et al., "Involvement of tumor integrin $\alpha_v\beta_3$ in hematogenous metastasis of human melanoma cells," *Clin. Exp. Metastasis* 19: 427-436, 2002.

Felding-Habermann, "Integrin adhesion receptors in tumor metastasis," *Clin. Exp. Metastasis* 20: 203-213, 2003.

Felding-Habermann, et al., "Integrin activation controls metastasis in human breast cancer," *Proc. Natl. Acad. Sci. U. S. A* 98: 1853-1858, 2001.

Frenkel et al., "Filamentous phage as vector-mediated antobidy delivery to the brain," *Proc. Natl. Acad. Sci. U.S.A*, 99:5675-5679, 2002.

Furger, K. A., et al., "$\beta_3$ Integrin Expression Increases Breast Carcinoma Cell Responsiveness to the Malignancy-Enhancing Effects of Osteopontin," *Mol. Cancer Res.*, 1: 810-819, 2003.

Gao, C., et al., "De novo identification of tumor-specific internalizing human antibody-receptor pairs by phage-display methods," *J. Immunol. Methods* 274: 185-197, 2003.

Garnett, M. C., "Targeted drug conjugates: principles and progress," *Adv. Drug Deliv. Rev.*, 53: 171-216, 2001.

Gladson et al., "Stage-Specific Expression of Integrin $\alpha_v\beta_3$ in Neuroblastic Tumors," *Am. J. Pathol.*, 148: 1423-1434, 1996.

Gladson et al., "Extracellular Matrix of Gliomas: Modulation of Cell Function," *J. Neuropathol. Exp. Neurol.*, 58: 1029-1040, 1999.

Gline et al., "A 50-Å Separation of the Integrin $\alpha_v\beta_3$ Extracellular Domain C Termini Reveals an Intermediate Activation State," *J Biol Chem*, 279:54567-54572, 2004.

Goldenberg, D. M., "Advancing role of radiolabeled antibodies in the therapy of cancer," *Cancer Immunol. Immunother.*, 52: 281-296, 2003.

Gui et al., "Integrin expression in primary breast cancer and its relation to axillary nodal status," *Surgery*, 117: 102-108, 1995.

Hood et al., "Role of Integrins in Cell Invasion and Migration," *Nat. Rev. Cancer* 2: 91-100, 2002.

Hughes et al., "Breaking the Integrin Hinge," *J. Biol. Chem.* 271: 6571-6574, 1996.

Huse et al., "Generation of a Large Combinatorial Library of the Immunoglobulin Repertoire in Phage Lambda," *Science*, 246:1275-1281, 1989.

Karadag et al., "Bone Sialoprotein, Matrix Metalloproteinase 2, and $\alpha_v\beta_3$ Integrin in Osteotropic Cancer Cell Division," *J Natl. Cancer Inst.*, 96:956-965, 2004.

Kiosses et al., "Rac recruits high-affinity integrin $\alpha_v\beta_3$ to lamellipodia in endothelial cell migration," *Nat. Cell Biol.* 3: 316-320, 2001.

Kortt et al., "Dimeric and trimeric antibodies: high avidity scFvs for cancer targeting," *Biomol. Eng*, 18: 95-108, 2001.

Langner et al., "RGD-mutants of B-lymphotropic polyomavirus capsids specifically bind to $\alpha_v\beta_3$ integrin," *Arch Virol*, 149:1877-1896, 2004.

Lerner et al., "On the use of combinatorial libraries to clone the "fossil record" of an individual's immune response," *Proc Natl. Acad. Sci.*, 88:9705-9706, 1991.

Liapis et al., "Integrin $\alpha_v\beta_3$ Expression by Bone-residing Breast Cancer Metastases," *Diagn. Mol. Pathol.* 5: 127-135, 1996.

Liddington et al., "Integrin activation takes shape," *J.Cell Biol.*, 158: 833-839, 2002.

Mao et al., "Phage-display library selection of high-affinity human single-chain antibodies to tumor-associated carbohydrate antigens sialyl Lewis and Lewis," *Proc. Natl. Acad. Sci. U.S.A.* 96: 6953-6958, 1999.

Mayer et al., "Radioimmunoguided Surgery in Colorectal Cancer Using a Genetically Engineered Anti-CEA Single-Chain Fv Antibody," *Clin. Cancer Res.*, 6: 1711-1719, 2000.

McCafferty et al., "Phage antibodies: filamentous phage displaying antibody variable domains," *Nature*, 348: 552, 1990.

McDonald et al., "Significance of Blood Vessel Leakiness in Cancer," *Cancer Res.* 62; 5381-5385, 2002.

Ménard et al., "Biologic and therapeutic role of HER2 in cancer," *Oncogene*, 22: 6570-6578, 2003.

Mould et al., "Role of ADMIDAS Cation-binding Site in Ligand Recognition by Intgrin $\alpha_5\beta_1$," *J Biol Chem*, 278:51622-51629, 2003.

Pampori et al., "Mechanisms and Consequences of Affinity Modulation of Integrin $\alpha_v\beta_3$ Detected with a Novel Patch-engineering Monovalent Ligand," *J. Biol. Chem.* 274: 21609-21616, 1999.

Perez. et al., "Clinical Cardiac Tolerability of Trastuzumab," *J. Clin. Oncol.*, 22: 322-329, 2004.

Pignatelli et al., "Integrins and Their Accessory Adhesion Molecules in Mammary Carcinomas: Loss of Polarization in Poorly Differentiated Tumors," *Hum. Pathol.* 23: 1159-1166, 1992.

Pilch et al., "Unique Ability of Integrin $\alpha_v\beta_3$ to Support Tumor Cell Arrest under Dynamic Flow Conditions," *J. Biol. Chem.*, 277: 21930-21938, 2002.

Power et al., "Generation of Recombinant Multimeric Antibody Fragments for Tumor Diagnosis and Therapy," *Methods. Mol. Biol.*, 207: 335-350, 2003.

Rolli et al., "Activated integrin $\alpha_v\beta_3$ cooperates with metalloproteinase MMP-9 in regulating migration of metastatic breast cancer cells," *Proc. Natl. Acad. Sci. U. S. A* 100: 9482-9487, 2003.

Rudland et al., "Prognostic Significance of the Metastasis-associated Protein Osteopontin in Human Breast Cancer," *Cancer Res.*, 62: 3417-3427, 2002.

Ruggeri, "Platelets n atherothrombosis," *Nat. Med.* 8: 1227-1234, 2002.

Ruoslahti et al., "RGD and Other Recognition Sequences for Integrins," *Annu. Rev. Cell Dev. Biol.*, 12: 697-715, 1996.

Ruoslahti, "The RGD story: a personal account," *Matrix Biology*, 22:459-465, 2003.

Savage et al., "Mechanisms of platelet aggregation," *Curr. Opin. Hematol.*, 8: 270-276, 2001.

Schoolmeester et al., "Monoclonal antibody IAC-1 is specific for activated $\alpha_2\beta_1$ and binds to amino acids 199 to 201 to the integrin $\alpha_2$ I-domain*Blood*," 104:390-396, 2004.

Schraa et al., "RGD-modified anti-CD3 antibodies redirect cytolytic capacity of cytotoxic T lymphocytesToward $\alpha_v\beta_3$ Expressing Endothelial Cells," *Int. J. Cancer*, 112:279-285, 2004.

Shattil et al., "Perspectives Series: Cell Adhesion in Vascular Biology. Integrin Signaling in Vascular Biology," *J. Clin. Invest.* 100: 1-5, 1997.

Shinohara et al., "$\beta_1$—and $\alpha_6$-integrin are surface markers on mouse spermatogonial stem cells," *Proc. Natl. Acad. Sci. U.S.A*, 96: 5504-5509, 1999.

Siddiqui et al., "The presence and release of tissue factor from human platelets," *Platelets*, 13: 247-253, 2002.

Singhal et al., "Elevated Plasma Osteopontin in Metastatic Breast Cancer Associated with Increased Tumor Burden and Decreased Survival," *Clin. Cancer Res.*, 3: 605-611, 1997.

Smith, "Methods for Analysis of the Integrin Ligand Binding Event," *Methods Cell Biol.* 69: 247-259, 2002.

Smith, "Retuximab (monoclonal anti-CD20 antibody): mechanisms of action and resistance," *Oncogene*, 22: 7359-7368, 2003.

Spigel et al., "Trastuzumab Regimens for HER2-Overexpressing Metastatic Breast Cancer," *Clin. Breast Cancer*, 4: 329-337, 2003.

Stupack et al., "Apoptosis of adherent cells by recruitment of caspase-8 to unligated integrins," *Cell Biol.* 155: 459-470, 2001.

Su et al., "In vitro cell studies of technetium-99m labeled RGD-HYNIC peptide, a comparison of tricine and EDDA as co-ligands," *Nucl. Med. Biol.*, 30: 141-149, 2003.

Sun et al., "Disruption of the long-range CPIIIa Cys5-Cys435 disulfide bond results in the production of constitutively active CPIIb-IIIa ($\alpha_{IIb}\beta_3$) integrin complexes," *Blood*, 100:2094-2101, 2002.

Tadokoro et al., "Talin Binding to Integrin β Tails: A Final Common Step in Integrin Activation," *Science* 302: 103-106, 2003.

Thumshirn et al., "Multimeric Cyclic RGD Peptides as Potential Tools for Tumor Targeting: Solid-Phase Peptide Synthesis and Chemoselective Oxime Ligation," *Chemistry.*, 9: 2717-2725, 2003.

Tuck et al., "Osteopontin Expression in a Group of Lymph Node Negative Breast Cancer Patients," *Int. J. Cancer*, 79: 502-508, 1998.

Tucker et al., αv Integrin inhibitors and cancer therapy, *Curr. Opin. Investig. Drugs*, 4: 722-731, 2003.

Van Belle et al., "Progression-Related Expression of $\alpha_v\beta_3$ Integrin In Melanomas and Nevi," *Hum. Pathol.*, 30:562-567, 1999.

Varner et al., "Tumor Angiogenesis and the Role Vascular Cell Integrin $\alpha_v\beta_3$," *Important. Adv. Oncol.*, 69-87: 69-87, 1996.

Vasudevan et al., "A single amino acid change in the binding pocket alters specificity of a anti-integrin antibody AP7.4 as revealed by its crystal structure," *Blood Cells, Molecules, and Diseases*, 32:176-181, 2004.

Wang et al., "Transcriptional regulation of the human osteopontin promoter: functional analysis and DNA-protein interactions," *Oncogene*, 19: 5801-5809, 2000.

Wang and Newman, "Adhesive and Signaling Properties of a Naturally Occuring Allele of Glycoprotein IIIa With an Amino Acid Substitution Within the Ligand Binding Domain—The Pen[a]/Pen[b] Platelet Alloantigenic Epitopes," *Blood*, 92:3260-3267, 1998.

Wayner et al., "Integrins $\alpha_v\beta_3$ and $\alpha_v\beta_5$ Contribute to Cell Attachment to Vitronectin but Differentially Distribute on the Cell Surface," *Journal of Cell Biology*, 113:919-929, 1991.

Weinreb et al., "Function-blocking Integrin $\alpha_v\beta_6$ Monoclonal Antibodies," *Journal of Biol. Chem.*, 279:17875-17887, 2004.

Woodside et al., "Integrin Activation," *Thromb. Haemost.*, 86: 316-323, 2001.

Wu et al., "Tumor localization of anti-CEA single-chain Fvs: improved targeting by non-covalent dimers," *Immunotechnology.*, 2: 21-36, 1996.

Xiong et al., "Crystal Structure of the Extracellular Segment of Integrin $\alpha_v\beta_3$ in Complex with an Arg-Gly-Asp Ligand," *Science* 296: 151-155, 2002.

Xiong et al., "Crystal Structure of the Extracellular Segment of Integrin αvβ3," *Science* 294: 339-345, 2001.

Xiong et al., "Integrins, cations and ligands: making the connection," *J. Thromb. Haemost.*, 1:1642-1654, 2003.

Xiong et al., "New insights into the structural basis of integrin activation," *Blood*, 102:1155-1159, 2003.

Yano et al., "RGD motif enhances immunogenicity and adjuvanicity of peptide antigens following intranasal immunization," *Vaccine*, 22:237-243, 2003.

Zheng et al., "Prostatic Carcinoma Cell Migration via $\alpha_v\beta_3$ Integrin Is Modulated by a Focal Adhesion Kinase Pathway," *Cancer Res.*, 59: 1655-1664, 1999.

Zheng et al., "Substrate Specificty of $\alpha_v\beta_3$ Integrin-mediated Cell Migration and Phosphatidylinositol 3-Kinase/AKT Pathway Activation," *J. Biol. Chem.*, 275: 24565-24574, 2000.

\* cited by examiner scFv BC-12 cDNA (SEQ ID NO: 1)

ATGGCACAGGTTCAGCTGGTACAGTCTGGAGCTGAGGTGAAGAAGCCTG
GGGCCTCAGTGAAGGTCTCCTGCAAGGCTTCTGGTTACACCTTTTCCAAC
TATGGTATCACCTGGGTGCGACAGGCCCCTGGACAAGGGCTTGAGTGGA
TGGGATGGATCAACAATGGTAACACACTATGCACAGAAGTTCCAGGG
CAGAGTCACCATGACCACAGACACATCCACGAGCACAGCCTACATGGA
GCTGAGGAGCCTTAGATCTGACGACACGGCCGTTTATTACTGTGCGAGA
GACCCCCGGGGTGACGACGAGCCCTACTGGGGCCAGGGAACCCTGGTC
ACCGTCTCCTCAGGCGGCGGCGGCTCTGGCGGAGGTGGCAGCGGCGGTG
GCGGATCCGAAATTGTGTTGACGCAGTCTCCACTCTCCTGCCCGTCACC
CTTGGACAGCCGGCCTCCATCTCCTGCCGGTCTAGTCAAAACCTCGTATA
CAGTGATGGAAACACCTACTTGAGTTGGTTTCAGCAGAGGCCAGGCCAA
TCTCCAAGGCGCCTAATTTATAAGGTTTCTAACCGGGACTCTGGGGTCCC
AGACAGATTCAGTGGCAGTGGGTCAGGCACTGATTTCACACTGAAAATC
AGCAGGGTGGAGGCTGAGGATATTGGGGTCTATTACTGCATGCAAGGCA
CACACTGGCCTCCGCGGACGTTCGGCCAAGGGACCAAGGTGGAGATCA
AACGTGGCCTCGGGGGCCTGGTCGACTACAAAGATGACGATGACAAAT
AA scFv Bc-15 cDNA (SEQ ID NO: 3)

ATGGCACAGGTGCAGCTGGTACAGTCTGGAGCTGAGGTGAAGGAGCC
TGGGTCCTCGGTGAAGGTCTCCTGCAAGGCTTCTGGAGGCACCTTCAG
CAGCTATGCTATCTACTGGGTGCGACAGGCCCCTGGACAAGGGCTTGA
GTGGATGGGATGGATCAATCCTGACAGTGGTGACACAAACTCTGCACA
GCAGTTTCAGGGCAGGGTCACCATGACCAGGGACACGTCCATCAGCAC
AGCCTATATGGAGCTGAGCAGGCTGAGATCTGACGACACGGCCATGTA
TTACTGTGCGAGACCCCCCGTGGGGATGGACCTGACTACTGGGGCCA
GGGCACCCTGGTCACCGTCTCCTCAGGCGGCGGTGGCGGATCCGAAAT
TGTGCTGACTCAGTCTCCAGGCACCCTGTCTTTGTCTCCAGGGGAAAG
AGCCACCCTCTCCTGCAGGGCCAGTCAGAGTGTTAGCAGCAGCTACTT
AGCCTGGTACCAGCAGAAACCTGGCCAGGCTCCCAGGCTCCTCATCTA
TGGTGCATCCAGCAGGGCCACTGGCATCCAGACAGGTTCAGTGGTAG
TGGGTCTGGGACAGACTTCACTCTCACCATCAGCAGACTGGAGCCTGA
AGATTTTGCAGTGTATTACTGTCAGCAGTATGGTAGCTCACCTCGGAC
GTTCGGCCAAGGGACCAAAGTGGATATCAAACGTGGCCTCGGGGGCC
TGGTCGACTACAAAGATGACGATGACAAATAA

Figure 2C scFv Mut-12 (SEQ ID NO: 5)

ATGGCACAGGTTCAGCTGGTACAGTCTGGAGCTGAGGTGAAGAAGC
TGGGGGCCTCAGTGAAGGTCTCCTGCAAGGCTTCTGGTTACACCTTTT
CCAACTATGGTATCACCTGGGTGCGACAGGCCCCTGGACAAGGGCTT
GAGTGGATGGGATGGATCAACAATGGTAACACACACTATGCACAGA
AGTTCCAGGGCAGAGTCACCATGACCACAGACACATCCACGAGCAC
AGCCTACATGGAGCTGAGGAGCCTTAGATCTGACGACACGGCCGTTT
ATTACTGTGCGAGAGACCCCGGGGTGAGGACGAGCCCTACTGGGG
CCAGGGAACCCTGGTCACCGTCTCCTCAGGCGGCGGCGGCTCTGGCG
GAGGTGGCAGCGGCGGTGGCGGATCCGAAATTGTGTTGACGCAGTCT
CCACTCTCCCTGCCCGTCACCCTTGGACAGCCGGCCTCCATCTCCTGC
CGGTCTAGTCAAAACCTCGTATACAGTGATGGAAACACCTACTTGAG
TTGGTTTCAGCAGAGGCCAGGCCAATCTCCAAGGCGCCTAATTTATA
AGGTTTCTAACCGGGACTCTGGGGTCCCAGACAGATTCAGTGGCAGT
GGGTCAGGCACTGATTTCACACTGAAAATCAGCAGGGTGGAGGCTG
AGGATATTGGGGTCTATTACTGCATGCAAGGCACACACTGGCCTCCG
CGGACGTTCGGCCAAGGGACCAAGGTGGAGATCAAACGTGGCCTCG
GGGGCCTGGTCGACTACAAAGATGACGATGACAAATAA scFv Mut-15 (SEQ ID NO: 6)

ATGGCACAGGTGCAGCTGGTACAGTCTGGAGCTGAGGTGAAGGAGCC
TGGGTCCTCGGTGAAGGTCTCCTGCAAGGCTTCTGGAGGCACCTTCAG
CAGCTATGCTATCTACTGGGTGCGACAGGCCCCTGGACAAGGGCTTG
AGTGGATGGGATGGATCAATCCTGACAGTGGTGACACAAACTCTGCA
CAGCAGTTTCAGGGCAGGGTCACCATGACCAGGGACACGTCCATCAG
CACAGCCTATATGGAGCTGAGCAGGCTGAGATCTGACGACACGGCCA
TGTATTACTGTGCGAGACCCCCCGTGGGGAGGGACCTGACTACTGG
GGCCAGGGCACCCTGGTCACCGTCTCCTCAGGCGGCGGTGGCGGATC
CGAAATTGTGCTGACTCAGTCTCCAGGCACCCTGTCTTTGTCTCCAGG
GGAAAGAGCCACCCTCTCCTGCAGGGCCAGTCAGAGTGTTAGCAGCA
GCTACTTAGCCTGGTACCAGCAGAAACCTGGCCAGGCTCCCAGGCTC
CTCATCTATGGTGCATCCAGCAGGGCCACTGGCATCCCAGACAGGTTC
AGTGGTAGTGGGTCTGGGACAGACTTCACTCTCACCATCAGCAGACT
GGAGCCTGAAGATTTTGCAGTGTATTACTGTCAGCAGTATGGTAGCTC
ACCTCGGACGTTCGGCCAAGGGACCAAAGTGGATATCAAACGTGGCC
TCGGGGGCCTGGTCGACTACAAAGATGACGATGACAAATAG

FIG. 2D

SEQUENCE LISTING

<160> NUMBER OF SEQ ID NOS: 13

<210> SEQ ID NO 1
<211> LENGTH: 786
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(786)

<400> SEQUENCE: 1

```
atg gca cag gtt cag ctg gta cag tct gga gct gag gtg aag aag cct      48
Met Ala Gln Val Gln Leu Val Gln Ser Gly Ala Glu Val Lys Lys Pro
1               5                  10                  15 ggg gcc tca gtg aag gtc tcc tgc aag gct tct ggt tac acc ttt tcc      96
Gly Ala Ser Val Lys Val Ser Cys Lys Ala Ser Gly Tyr Thr Phe Ser
            20                  25                  30 aac tat ggt atc acc tgg gtg cga cag gcc cct gga caa ggg ctt gag     144
Asn Tyr Gly Ile Thr Trp Val Arg Gln Ala Pro Gly Gln Gly Leu Glu
        35                  40                  45 tgg atg gga tgg atc aac aat ggt aac aca cac tat gca cag aag ttc     192
Trp Met Gly Trp Ile Asn Asn Gly Asn Thr His Tyr Ala Gln Lys Phe
    50                  55                  60 cag ggc aga gtc acc atg acc aca gac aca tcc acg agc aca gcc tac     240
Gln Gly Arg Val Thr Met Thr Thr Asp Thr Ser Thr Ser Thr Ala Tyr
65                  70                  75                  80 atg gag ctg agg agc ctt aga tct gac gac acg gcc gtt tat tac tgt     288
Met Glu Leu Arg Ser Leu Arg Ser Asp Asp Thr Ala Val Tyr Tyr Cys
                85                  90                  95 gcg aga gac ccc cgg ggt gac gac gag ccc tac tgg ggc cag gga acc     336
Ala Arg Asp Pro Arg Gly Asp Asp Glu Pro Tyr Trp Gly Gln Gly Thr
            100                 105                 110 ctg gtc acc gtc tcc tca ggc ggc ggc ggc tct ggc gga ggt ggc agc     384
Leu Val Thr Val Ser Ser Gly Gly Gly Gly Ser Gly Gly Gly Gly Ser
        115                 120                 125 ggc ggt ggc gga tcc gaa att gtg ttg acg cag tct cca ctc tcc ctg     432
Gly Gly Gly Gly Ser Glu Ile Val Leu Thr Gln Ser Pro Leu Ser Leu
    130                 135                 140 ccc gtc acc ctt gga cag ccg gcc tcc atc tcc tgc cgg tct agt caa     480
Pro Val Thr Leu Gly Gln Pro Ala Ser Ile Ser Cys Arg Ser Ser Gln
145                 150                 155                 160 aac ctc gta tac agt gat gga aac acc tac ttg agt tgg ttt cag cag     528
Asn Leu Val Tyr Ser Asp Gly Asn Thr Tyr Leu Ser Trp Phe Gln Gln
                165                 170                 175 agg cca ggc caa tct cca agg cgc cta att tat aag gtt tct aac cgg     576
Arg Pro Gly Gln Ser Pro Arg Arg Leu Ile Tyr Lys Val Ser Asn Arg
            180                 185                 190 gac tct ggg gtc cca gac aga ttc agt ggc agt ggg tca ggc act gat     624
Asp Ser Gly Val Pro Asp Arg Phe Ser Gly Ser Gly Ser Gly Thr Asp
        195                 200                 205 ttc aca ctg aaa atc agc agg gtg gag gct gag gat att ggg gtc tat     672
Phe Thr Leu Lys Ile Ser Arg Val Glu Ala Glu Asp Ile Gly Val Tyr
    210                 215                 220
```

```
tac tgc atg caa ggc aca cac tgg cct ccg cgg acg ttc ggc caa ggg      720
Tyr Cys Met Gln Gly Thr His Trp Pro Pro Arg Thr Phe Gly Gln Gly
225                 230                 235                 240 acc aag gtg gag atc aaa cgt ggc ctc ggg ggc ctg gtc gac tac aaa      768
Thr Lys Val Glu Ile Lys Arg Gly Leu Gly Gly Leu Val Asp Tyr Lys
                245                 250                 255 gat gac gat gac aaa taa                                              786
Asp Asp Asp Asp Lys
            260

<210> SEQ ID NO 2
<211> LENGTH: 261
<212> TYPE: PRT
<213> ORGANISM: Artificial
<220> FEATURE:
<223> OTHER INFORMATION: Synthetic Construct

<400> SEQUENCE: 2

Met Ala Gln Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Ser
            20                  25                  30

Asn Tyr Gly Ile Thr Trp Val Arg Gln Ala Pro Gly Gln Gly Leu Glu
        35                  40                  45

Trp Met Gly Trp Ile Asn Asn Gly Asn Thr His Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro Arg Gly Asp Asp Glu Pro Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Glu Ile Val Leu Thr Gln Ser Pro Leu Ser Leu
    130                 135                 140

Pro Val Thr Leu Gly Gln Pro Ala Ser Ile Ser Cys Arg Ser Ser Gln
145                 150                 155                 160

Asn Leu Val Tyr Ser Asp Gly Asn Thr Tyr Leu Ser Trp Phe Gln Gln
                165                 170                 175

Arg Pro Gly Gln Ser Pro Arg Arg Leu Ile Tyr Lys Val Ser Asn Arg
            180                 185                 190

Asp Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Ile Gly Val Tyr
    210                 215                 220

Tyr Cys Met Gln Gly Thr His Trp Pro Pro Arg Thr Phe Gly Gln Gly
225                 230                 235                 240

Thr Lys Val Glu Ile Lys Arg Gly Leu Gly Gly Leu Val Asp Tyr Lys
                245                 250                 255

Asp Asp Asp Asp Lys
            260

<210> SEQ ID NO 3
<211> LENGTH: 750
<212> TYPE: DNA
<213> ORGANISM: Artificial
```

```
<220> FEATURE:
<223> OTHER INFORMATION: Synthetic Construct
<220> FEATURE:
<221> NAME/KEY: CDS
<222> LOCATION: (1)..(750)

<400> SEQUENCE: 3
```

| | | | | | | | | | | | | | | | | |
|---|---|---|---|---|---|---|---|---|---|---|---|---|---|---|---|---|
| atg | gca | cag | gtg | cag | ctg | gta | cag | tct | gga | gct | gag | gtg | aag | gag | cct | 48 |
| Met | Ala | Gln | Val | Gln | Leu | Val | Gln | Ser | Gly | Ala | Glu | Val | Lys | Glu | Pro | |
| 1 | | | | 5 | | | | | 10 | | | | | 15 | | |
| ggg | tcc | tcg | gtg | aag | gtc | tcc | tgc | aag | gct | tct | gga | ggc | acc | ttc | agc | 96 |
| Gly | Ser | Ser | Val | Lys | Val | Ser | Cys | Lys | Ala | Ser | Gly | Gly | Thr | Phe | Ser | |
| | | | 20 | | | | | 25 | | | | | 30 | | | |
| agc | tat | gct | atc | tac | tgg | gtg | cga | cag | gcc | cct | gga | caa | ggg | ctt | gag | 144 |
| Ser | Tyr | Ala | Ile | Tyr | Trp | Val | Arg | Gln | Ala | Pro | Gly | Gln | Gly | Leu | Glu | |
| | | 35 | | | | | 40 | | | | | 45 | | | | |
| tgg | atg | gga | tgg | atc | aat | cct | gac | agt | ggt | gac | aca | aac | tct | gca | cag | 192 |
| Trp | Met | Gly | Trp | Ile | Asn | Pro | Asp | Ser | Gly | Asp | Thr | Asn | Ser | Ala | Gln | |
| 50 | | | | | 55 | | | | | 60 | | | | | | |
| cag | ttt | cag | ggc | agg | gtc | acc | atg | acc | agg | gac | acg | tcc | atc | agc | aca | 240 |
| Gln | Phe | Gln | Gly | Arg | Val | Thr | Met | Thr | Arg | Asp | Thr | Ser | Ile | Ser | Thr | |
| 65 | | | | 70 | | | | | 75 | | | | | 80 | | |
| gcc | tat | atg | gag | ctg | agc | agg | ctg | aga | tct | gac | gac | acg | gcc | atg | tat | 288 |
| Ala | Tyr | Met | Glu | Leu | Ser | Arg | Leu | Arg | Ser | Asp | Asp | Thr | Ala | Met | Tyr | |
| | | | | 85 | | | | | 90 | | | | | 95 | | |
| tac | tgt | gcg | aga | ccc | ccc | cgt | ggg | gat | gga | cct | gac | tac | tgg | ggc | cag | 336 |
| Tyr | Cys | Ala | Arg | Pro | Pro | Arg | Gly | Asp | Gly | Pro | Asp | Tyr | Trp | Gly | Gln | |
| | | | 100 | | | | | 105 | | | | | 110 | | | |
| ggc | acc | ctg | gtc | acc | gtc | tcc | tca | ggc | ggc | ggt | ggc | gga | tcc | gaa | att | 384 |
| Gly | Thr | Leu | Val | Thr | Val | Ser | Ser | Gly | Gly | Gly | Gly | Gly | Ser | Glu | Ile | |
| | | 115 | | | | | 120 | | | | | 125 | | | | |
| gtg | ctg | act | cag | tct | cca | ggc | acc | ctg | tct | ttg | tct | cca | ggg | gaa | aga | 432 |
| Val | Leu | Thr | Gln | Ser | Pro | Gly | Thr | Leu | Ser | Leu | Ser | Pro | Gly | Glu | Arg | |
| 130 | | | | | 135 | | | | | 140 | | | | | | |
| gcc | acc | ctc | tcc | tgc | agg | gcc | agt | cag | agt | gtt | agc | agc | agc | tac | tta | 480 |
| Ala | Thr | Leu | Ser | Cys | Arg | Ala | Ser | Gln | Ser | Val | Ser | Ser | Ser | Tyr | Leu | |
| 145 | | | | | 150 | | | | | 155 | | | | | 160 | |
| gcc | tgg | tac | cag | cag | aaa | cct | ggc | cag | gct | ccc | agg | ctc | ctc | atc | tat | 528 |
| Ala | Trp | Tyr | Gln | Gln | Lys | Pro | Gly | Gln | Ala | Pro | Arg | Leu | Leu | Ile | Tyr | |
| | | | | 165 | | | | | 170 | | | | | 175 | | |
| ggt | gca | tcc | agc | agg | gcc | act | ggc | atc | cca | gac | agg | ttc | agt | ggt | agt | 576 |
| Gly | Ala | Ser | Ser | Arg | Ala | Thr | Gly | Ile | Pro | Asp | Arg | Phe | Ser | Gly | Ser | |
| | | | 180 | | | | | 185 | | | | | 190 | | | |
| ggg | tct | ggg | aca | gac | ttc | act | ctc | acc | atc | agc | aga | ctg | gag | cct | gaa | 624 |
| Gly | Ser | Gly | Thr | Asp | Phe | Thr | Leu | Thr | Ile | Ser | Arg | Leu | Glu | Pro | Glu | |
| | | 195 | | | | | 200 | | | | | 205 | | | | |
| gat | ttt | gca | gtg | tat | tac | tgt | cag | cag | tat | ggt | agc | tca | cct | cgg | acg | 672 |
| Asp | Phe | Ala | Val | Tyr | Tyr | Cys | Gln | Gln | Tyr | Gly | Ser | Ser | Pro | Arg | Thr | |
| 210 | | | | | 215 | | | | | 220 | | | | | | |
| ttc | ggc | caa | ggg | acc | aaa | gtg | gat | atc | aaa | cgt | ggc | ctc | ggg | ggc | ctg | 720 |
| Phe | Gly | Gln | Gly | Thr | Lys | Val | Asp | Ile | Lys | Arg | Gly | Leu | Gly | Gly | Leu | |
| 225 | | | | 230 | | | | | 235 | | | | | 240 | | |
| gtc | gac | tac | aaa | gat | gac | gat | gac | aaa | taa | | | | | | | 750 |
| Val | Asp | Tyr | Lys | Asp | Asp | Asp | Asp | Lys | | | | | | | | |
| | | | | 245 | | | | | | | | | | | | |

```
<210> SEQ ID NO 4
<211> LENGTH: 249
<212> TYPE: PRT
<213> ORGANISM: Artificial
<220> FEATURE:
<223> OTHER INFORMATION: Synthetic Construct
```

<400> SEQUENCE: 4

```
Met Ala Gln Val Gln Leu Val Gln Ser Gly Ala Glu Val Lys Glu Pro
1               5                   10                  15
Gly Ser Ser Val Lys Val Ser Cys Lys Ala Ser Gly Gly Thr Phe Ser
            20                  25                  30
Ser Tyr Ala Ile Tyr Trp Val Arg Gln Ala Pro Gly Gln Gly Leu Glu
        35                  40                  45
Trp Met Gly Trp Ile Asn Pro Asp Ser Gly Asp Thr Asn Ser Ala Gln
50                  55                  60
Gln Phe Gln Gly Arg Val Thr Met Thr Arg Asp Thr Ser Ile Ser Thr
65                  70                  75                  80
Ala Tyr Met Glu Leu Ser Arg Leu Arg Ser Asp Asp Thr Ala Met Tyr
                85                  90                  95
Tyr Cys Ala Arg Pro Pro Arg Gly Asp Gly Pro Asp Tyr Trp Gly Gln
            100                 105                 110
Gly Thr Leu Val Thr Val Ser Ser Gly Gly Gly Gly Ser Glu Ile
        115                 120                 125
Val Leu Thr Gln Ser Pro Gly Thr Leu Ser Leu Ser Pro Gly Glu Arg
130                 135                 140
Ala Thr Leu Ser Cys Arg Ala Ser Gln Ser Val Ser Ser Ser Tyr Leu
145                 150                 155                 160
Ala Trp Tyr Gln Gln Lys Pro Gly Gln Ala Pro Arg Leu Leu Ile Tyr
                165                 170                 175
Gly Ala Ser Ser Arg Ala Thr Gly Ile Pro Asp Arg Phe Ser Gly Ser
            180                 185                 190
Gly Ser Gly Thr Asp Phe Thr Leu Thr Ile Ser Arg Leu Glu Pro Glu
        195                 200                 205
Asp Phe Ala Val Tyr Tyr Cys Gln Gln Tyr Gly Ser Ser Pro Arg Thr
210                 215                 220
Phe Gly Gln Gly Thr Lys Val Asp Ile Lys Arg Gly Leu Gly Gly Leu
225                 230                 235                 240
Val Asp Tyr Lys Asp Asp Asp Lys
                245
```

<210> SEQ ID NO 5
<211> LENGTH: 786
<212> TYPE: DNA
<213> ORGANISM: Artificial
<220> FEATURE:
<223> OTHER INFORMATION: Synthetic Construct

<400> SEQUENCE: 5

```
atggcacagg ttcagctggt acagtctgga gctgaggtga agaagcctgg ggcctcagtg      60
aaggtctcct gcaaggcttc tggttacacc ttttccaact atggtatcac ctgggtgcga     120
caggcccctg gacaagggct tgagtggatg ggatggatca acaatggtaa cacacactat     180
gcacagaagt tccagggcag agtcaccatg accacagaca catccacgag cacagcctac     240
atggagctga ggagccttag atctgacgac acggccgttt attactgtgc gagagacccc     300
cggggtgagg acgagcccta ctggggccag ggaaccctgg tcaccgtctc ctcaggcggc     360
ggcggctctg gcggaggtgg cagcggcggt ggcggatccg aaattgtgtt gacgcagtct     420
ccactctccc tgcccgtcac ccttggacag ccggcctcca tctcctgccg gtctagtcaa     480
aacctcgtat acagtgatgg aaacacctac ttgagttggt tcagcagag gccaggccaa     540
```

```
tctccaaggc gcctaattta taaggttttct aaccgggact ctggggtccc agacagattc      600
agtggcagtg ggtcaggcac tgatttcaca ctgaaaatca gcagggtgga ggctgaggat      660 attgggggtct attactgcat gcaaggcaca cactggcctc cgcggacgtt cggccaaggg     720
accaaggtgg agatcaaacg tggcctcggg ggcctggtcg actacaaaga tgacgatgac     780
aaataa                                                                 786
```

<210> SEQ ID NO 6
<211> LENGTH: 750
<212> TYPE: DNA
<213> ORGANISM: Artificial
<220> FEATURE:
<223> OTHER INFORMATION: Synthetic Construct

<400> SEQUENCE: 6

```
atggcacagg tgcagctggt acagtctgga gctgaggtga aggagcctgg gtcctcggtg       60
aaggtctcct gcaaggcttc tggaggcacc ttcagcagct atgctatcta ctgggtgcga      120
caggcccctg gacaagggct tgagtggatg ggatggatca atcctgacag tggtgacaca      180
aactctgcac agcagtttca gggcagggtc accatgacca gggacacgtc catcagcaca      240
gcctatatgg agctgagcag gctgagatct gacgacacgg ccatgtatta ctgtgcgaga      300
cccccccgtg ggaggggacc tgactactgg ggccagggca ccctggtcac cgtctcctca      360
ggcggcggtg gcggatccga aattgtgctg actcagtctc caggcaccct gtctttgtct      420
ccaggggaaa gagccaccct ctcctgcagg gccagtcaga gtgttagcag cagctactta      480
gcctggtacc agcagaaacc tggccaggct cccaggctcc tcatctatgg tgcatccagc      540
agggccactg gcatcccaga caggttcagt ggtagtgggt ctgggacaga cttcactctc      600
accatcagca gactggagcc tgaagatttt gcagtgtatt actgtcagca gtatggtagc      660
tcacctcgga cgttcggcca agggaccaaa gtggatatca aacgtggcct cgggggcctg      720
gtcgactaca aagatgacga tgacaaatag                                       750
```

<210> SEQ ID NO 7
<211> LENGTH: 259
<212> TYPE: PRT
<213> ORGANISM: Artificial
<220> FEATURE:
<223> OTHER INFORMATION: Synthetic Construct

<400> SEQUENCE: 7

```
Met Ala Gln Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Ser
            20                  25                  30

Asn Tyr Gly Ile Thr Trp Val Arg Gln Ala Pro Gly Gln Gly Leu Glu
        35                  40                  45

Trp Met Gly Trp Ile Asn Asn Gly Asn Thr His Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro Arg Gly Asp Asp Glu Pro Tyr Trp Gly Gln Gly Thr
            100                 105                 110

Leu Val Thr Val Ser Ser Gly Gly Gly Gly Ser Gly Gly Gly Gly Ser
        115                 120                 125
```

```
Gly Gly Gly Gly Ser Glu Ile Val Leu Thr Gln Ser Pro Leu Ser Leu
            130                 135                 140

Pro Val Thr Leu Gly Gln Pro Ala Ser Ile Ser Cys Arg Ser Ser Gln
145                 150                 155                 160

Asn Leu Val Tyr Ser Asp Gly Asn Thr Tyr Leu Ser Trp Phe Gln Gln
                165                 170                 175

Arg Pro Gly Gln Ser Pro Arg Arg Leu Ile Tyr Lys Val Ser Asn Arg
            180                 185                 190

Asp Ser Gly Val Pro Asp Arg Phe Ser Gly Ser Gly Ser Gly Thr Asp
        195                 200                 205

Phe Thr Leu Lys Ile Ser Arg Val Glu Arg Glu Asp Ile Gly Val Tyr
    210                 215                 220

Tyr Cys Met Gln Gly Thr His Trp Pro Pro Arg Thr Phe Gly Gln Gly
225                 230                 235                 240

Thr Lys Val Glu Ile Lys Arg Gly Leu Gly Gly Leu Val Asp Tyr Lys
                245                 250                 255

Asp Asp Asp

<210> SEQ ID NO 8
<211> LENGTH: 247
<212> TYPE: PRT
<213> ORGANISM: Artificial
<220> FEATURE:
<223> OTHER INFORMATION: Synthetic Construct

<400> SEQUENCE: 8

Met Ala Gln Val Gln Leu Val Gln Ser Gly Ala Glu Val Lys Glu Pro
1               5                   10                  15

Gly Ser Ser Val Lys Val Ser Cys Lys Ala Ser Gly Gly Thr Phe Ser
            20                  25                  30

Ser Tyr Ala Ile Tyr Trp Val Arg Gln Ala Pro Gly Gln Gly Leu Glu
        35                  40                  45

Trp Met Gly Trp Ile Asn Pro Asp Ser Gly Asp Thr Asn Ser Ala Gln
    50                  55                  60

Gln Phe Gln Gly Arg Val Thr Met Thr Arg Asp Thr Ser Ile Ser Thr
65                  70                  75                  80

Ala Tyr Met Glu Leu Ser Arg Leu Arg Ser Asp Asp Thr Ala Met Tyr
                85                  90                  95

Tyr Cys Ala Arg Pro Pro Arg Gly Asp Gly Pro Asp Tyr Trp Gly Gln
            100                 105                 110

Gly Thr Leu Val Thr Val Ser Ser Gly Gly Gly Gly Ser Glu Ile
        115                 120                 125

Val Leu Thr Gln Ser Pro Gly Thr Leu Ser Leu Ser Pro Gly Glu Arg
    130                 135                 140

Ala Thr Leu Ser Cys Arg Ala Ser Gln Ser Val Ser Ser Ser Tyr Leu
145                 150                 155                 160

Ala Trp Tyr Gln Gln Lys Pro Gly Gln Ala Pro Arg Leu Leu Ile Tyr
                165                 170                 175

Gly Ala Ser Ser Arg Ala Thr Gly Ile Pro Asp Arg Phe Ser Gly Ser
            180                 185                 190

Gly Ser Gly Thr Asp Phe Thr Leu Thr Ile Ser Arg Leu Glu Pro Glu
        195                 200                 205

Asp Phe Ala Val Tyr Tyr Cys Gln Gln Tyr Gly Ser Ser Pro Arg Thr
    210                 215                 220
```

-continued

Phe Gly Gln Gly Thr Lys Val Asp Ile Lys Arg Gly Leu Gly Gly Leu
225                 230                 235                 240

Val Asp Tyr Lys Asp Asp Asp
                245

<210> SEQ ID NO 9
<211> LENGTH: 189
<212> TYPE: PRT
<213> ORGANISM: Artificial
<220> FEATURE:
<223> OTHER INFORMATION: Synthetic Construct

<400> SEQUENCE: 9

Met Ala Gln Val Gln Leu Val Gln Ser Gly Ala Glu Val Lys Pro Gly
1               5                   10                  15

Ser Val Lys Val Ser Cys Lys Ala Ser Gly Thr Phe Ser Tyr Ile Trp
                20                  25                  30

Val Arg Gln Ala Pro Gly Gln Gly Leu Glu Trp Met Gly Trp Ile Asn
            35                  40                  45

Gly Thr Ala Gln Phe Gln Gly Arg Val Thr Met Thr Asp Thr Ser Ser
        50                  55                  60

Thr Ala Tyr Met Glu Leu Leu Arg Ser Asp Asp Thr Ala Tyr Tyr Cys
65                  70                  75                  80

Ala Arg Pro Arg Gly Asp Tyr Trp Gly Gln Gly Thr Leu Val Thr Val
                85                  90                  95

Ser Ser Gly Gly Gly Gly Ser Glu Ile Val Leu Thr Gln Ser Pro
            100                 105                 110

Leu Gly Ala Ser Cys Arg Ser Gln Ser Tyr Leu Trp Gln Gln Pro Gly
        115                 120                 125

Gln Pro Arg Leu Ile Tyr Ser Arg Gly Pro Asp Arg Phe Ser Gly Ser
    130                 135                 140

Gly Ser Gly Thr Asp Phe Thr Leu Ile Ser Arg Glu Glu Asp Val Tyr
145                 150                 155                 160

Tyr Cys Gln Gly Pro Arg Thr Phe Gly Gln Gly Thr Lys Val Ile Lys
                165                 170                 175

Arg Gly Leu Gly Gly Leu Val Asp Tyr Lys Asp Asp
            180                 185

<210> SEQ ID NO 10
<211> LENGTH: 257
<212> TYPE: PRT
<213> ORGANISM: Artificial
<220> FEATURE:
<223> OTHER INFORMATION: Synthetic Construct

<400> SEQUENCE: 10

Met Ala Gln Val Gln Leu Val Gln Ser Gly Gly Gly Leu Val Gln Pro
1               5                   10                  15

Gly Gly Ser Leu Arg Leu Ser Cys Ala Ala Ser Gly Phe Thr Phe Ser
                20                  25                  30

Ser Tyr Trp Met Ser Trp Val Arg Gln Ala Pro Gly Lys Gly Leu Glu
            35                  40                  45

Trp Val Ala Asn Ile Lys Gln Asp Gly Ser Glu Lys Tyr Tyr Val Asp
        50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

```
Tyr Cys Ala Arg Asp Gly Gly Phe Ala Gly Trp Ala Phe Asp Ile Trp
                100                 105                 110
Gly Gln Gly Thr Thr Val Thr Val Ser Ser Gly Gly Gly Ser Gly
            115                 120                 125
Gly Gly Gly Ser Gly Gly Gly Ser Asp Ile Gln Met Thr Gln Ser
        130                 135                 140
Pro Ser Ala Leu Ser Ala Ser Val Gly Asp Arg Val Thr Ile Thr Cys
145                 150                 155                 160
Arg Ala Ser Gln Gly Leu Asp Asn Tyr Leu Ala Trp Tyr Gln Leu Gln
                165                 170                 175
Pro Gly Lys Ala Pro Lys Leu Leu Ile Tyr Asp Ala Phe Thr Leu Gln
            180                 185                 190
Ser Gly Val Pro Ser Arg Phe Ser Gly Gly Gly Ser Gly Thr Asp Phe
        195                 200                 205
Thr Leu Thr Ile Ser Ser Leu Gln Pro Glu Asp Phe Ala Thr Tyr Phe
210                 215                 220
Cys Gln Gln Leu Gln Ser Tyr Pro Leu Thr Phe Gly Gly Gly Thr Lys
225                 230                 235                 240
Val Glu Ile Lys Arg Gly Leu Gly Leu Val Asp Tyr Lys Asp Asp
                245                 250                 255
Asp

<210> SEQ ID NO 11
<211> LENGTH: 7
<212> TYPE: PRT
<213> ORGANISM: Artificial
<220> FEATURE:
<223> OTHER INFORMATION: Synthetic Construct

<400> SEQUENCE: 11

Gly Arg Gly Asp Ser Pro Lys
1               5

<210> SEQ ID NO 12
<211> LENGTH: 48
<212> TYPE: DNA
<213> ORGANISM: Artificial
<220> FEATURE:
<223> OTHER INFORMATION: Primer

<400> SEQUENCE: 12
aaatagacta gtggaggcgg tggctctatg agtgttttag tgtattct               48

<210> SEQ ID NO 13
<211> LENGTH: 39
<212> TYPE: DNA
<213> ORGANISM: Artificial
<220> FEATURE:
<223> OTHER INFORMATION: Primer

<400> SEQUENCE: 13
gatttagcta gcttattatg aggaagtttc cattaaacg               39
```

METHODS AND COMPOSITIONS FOR INHIBITION OF METASTASIS

CROSS-REFERENCE TO RELATED APPLICATIONS

This application claims the benefit of U.S. Application No. 60/544,807, filed Feb. 13, 2004, and U.S. Application No. 60/626,726, filed Nov. 10, 2004, the entire disclosures of which are incorporated herein by reference.

STATEMENT OF GOVERNMENT SUPPORT

This invention was made with Government support by Grant Nos. NCI-CA95458 and NIAID-AI47127, awarded by the National Institutes of Health and Grant No. DAMD 17-99-1-9368, awarded by the U.S. Army Breast Cancer Research Program. The Government has certain rights in this invention.

FIELD

This invention generally relates to methods of producing an antibody phage population having affinity for a tumor cell target expressing a metastatic phenotype. The invention further relates to antibody compositions that specifically bind to a cell surface receptor on the metastatic cell.

BACKGROUND

Breast cancer metastasis to lungs, liver, bone and brain is the primary cause of death in breast cancer patients. It involves cancer cell dissemination via the blood stream and depends on adhesive and invasive tumor cell functions and their ability to survive and proliferate at the target site. Bogenrieder et al., *Oncogene* 22: 6524-6536, 2003. These events are supported by integrins, a family of transmembrane adhesion receptors composed of $\alpha$ and $\beta$ subunits. Felding-Habermann, *Clin. Exp. Metastasis* 20: 203-213, 2003; Hood et al., *Nat. Rev. Cancer* 2: 91-100, 2002. Integrins exist in distinct states of activation, which determine the affinity for ligand and regulate whether soluble ligands are bound, which matrix proteins are recognized, and the degree to which cells can adhere, migrate and arrest under dynamic flow conditions as found in the circulation. Tadokoro et al., *Science* 302: 103-106, 2003; Shattil et al., *J. Clin. Invest.* 100: 1-5, 1997; Felding-Habermann, et al., *Proc. Natl. Acad. Sci. U.S.A* 98: 1853-1858, 2001.

An integrin found on breast cancer cells, but not on normal breast epithelium is $\alpha v\beta 3$. Expressio[n of this receptor correlates with invasion and cancer progression. Liapis et al., *Diagn. Mol. Pathol.* 5: 127-135, 1996; Pignatelli et al., *Hum. Pathol.* 23: 1159-1166, 1992. Human breast cancer cells can express $\alpha v\beta 3$ in an activated or a non-activated functional state. Activated $\alpha v\beta 3$ supports breast cancer cell attachment during blood flow, and strongly promotes invasive tumor cell migration. In particular, only the activated state supports target organ colonization by circulating breast cancer cells in a mouse model, and metastatic cells isolated from breast cancer patient blood express $\alpha v\beta 3$ in a constitutively activated form. Felding-Habermann et al.; *Proc. Natl. Acad. Sci. U.S.A* 98: 1853-1858, 2001; Rolli et al., *Proc. Natl. Acad. Sci. U.S.A* 100: 9482-9487, 2003. Integrin transition between distinct states of activation is associated with conformational changes within the heterodimer. Calzada et al., *J. Biol. Chem.* 277: 39899-39908, 2002; Beglova et al., *Nat. Struct. Biol.* 9: 282-287, 2002; Xiong et al., *Science* 294: 339-345, 2001; Xiong et al., *Science* 296: 151-155, 2002; Pampori et al., *J. Biol. Chem.* 274: 21609-21616, 1999.

Like other integrins, $\alpha v\beta 3$ can exist in distinct states of activation and functional affinity. The activated or high affinity state of $\alpha v\beta 3$ has a unique molecular conformation that is distinct from the non-activated state. Xiong et al., *Science,* 294: 339-345, 2001; Xiong et al., *Science,* 296: 151-155, 2002; Xiong et al., *Blood,* 102: 1155-1159, 2003.

In contrast to the non-activated receptor, activated $\alpha v\beta 3$ is functionally characterized primarily through its ability to bind soluble ligand proteins, to support tumor cell interaction with platelets during blood flow and thereby mediated tumor cell arrest under conditions as found in the vasculature, and to promote invasive tumor cell and endothelial cell migration very strongly. The latter is probably very important for angiogenesis. The ability of the activated $\alpha v\beta 3$ integrin to bind soluble ligands is a key property that enables the ligand-mimetic scFv antibodies to bind specifically and exclusively to the activated conformation of $\alpha v\beta 3$.

No therapy is known today that prevents cancer, for example, breast cancer, from becoming systemic, and there is little understanding of even how to design and test such drugs; yet metastases ultimately are responsible for much of the suffering and mortality from breast cancer. A need exists to identify and target molecular and functional markers that identify metastatic breast cancer cells and to generate reagents for their specific inhibition.

SUMMARY

The invention is generally related to methods of producing an antibody phage population having affinity for a tumor cell target which is a tumor cell expressing a metastatic phenotype. The tumor cell expressing the metastatic phenotype can be a cell line expressing an activated cell surface receptor, for example, an activated integrin receptor or an $\alpha v\beta 3$ integrin receptor. The invention further relates to an antibody composition that specifically binds to a cell surface receptor on a metastatic cell. The antibody composition specifically binds to an activated cell surface receptor on a metastatic cell, for example, an activated integrin receptor or an $\alpha v\beta 3$ integrin receptor. The invention further relates to methods for alleviating a disease state in a mammal by treatment with a cancer therapeutic comprising the step of administering to the mammal a therapeutic amount of the pharmaceutical composition of the antibody composition. The invention further relates to methods of detecting an activated cell surface receptor on a metastatic tumor cell surface in a mammalian tissue sample and to methods of identifying cells liable to undergo metastasis associated with a disease state comprising contacting a patient suspected of being at risk for metastasis with the antibody composition, the antibody having associated therewith an imaging moiety.

Cells or tumor cells with a non-activated $\alpha v\beta 3$ integrin receptor refers to a conformation of $\alpha v\beta 3$ that is unable to bind soluble ligands and does not support tumor cell arrest under dynamic flow conditions as during blood flow under conditions found in the vasculature. This non-activated conformation of $\alpha v\beta 3$ can be associated with non-metastatic tumor cells and it is not recognized by an antibody, for example, scFv antibodies Bc-12 or Bc-15.

In one embodiment, an antibody which specifically binds to an activated $\alpha v\beta 3$ integrin receptor which is differentially produced on a cell in a metastatic state compared to a similar, non-metastatic cell. In a detailed embodiment, the antibody comprises scFv antibody Bc-12. In a further detailed embodiment, the antibody comprises SEQ ID NO: 2. In a detailed embodiment, the antibody comprises scFv antibody Bc-15. In a further detailed embodiment, the antibody comprises SEQ ID NO: 4. In a further embodiment, the antibody comprises an R-G-D sequence in a complementary determining region (CDR). In a detailed aspect, the CDR can be CDR-H3. In a further detailed aspect, the metastatic cell targets to a tissue selected from breast, brain, lung, liver, or bone. In a further detailed aspect, a pharmaceutical composition comprises the antibody.

The present invention further provides a cDNA encoding scFv Bc-12 in a phage display vector for expression and production of scFv antibody Bc-12. In a detailed embodiment, the cDNA encoding scFv Bc-12 comprises SEQ ID NO: 1. The cDNA encoding scFv Bc-12 has an ATCC accession number PTA-6303, date of deposit: Nov. 12, 2004. The present invention further provides a cDNA encoding scFv Bc-15 in a phage display vector for expression and production of scFv antibody Bc-15. In a detailed embodiment, the cDNA encoding scFv Bc-15 comprises SEQ ID NO: 3. The cDNA encoding scFv Bc-15 has an ATCC accession number PTA-6304, date of deposit: Nov. 12, 2004.

In another embodiment, an antibody specifically binds to an activated αvβ3 integrin receptor and does not bind to a non-activated αxβ3 integrin receptor. In a further aspect, the activated αvβ3 integrin receptor is differentially produced on a cell in a metastatic state compared to a similar, non-metastatic cell.

In another embodiment, an antibody comprises a ligand mimetic which specifically binds to an activated αvβ3 integrin receptor which is differentially produced on a cell in a metastatic state compared to a similar, non-metastatic cell.

In another embodiment, a method for treating a disease state in a mammal comprises administering to the mammal an antibody which specifically binds to an activated αvβ3 integrin receptor which is differentially produced on a cell in a metastatic state as compared to a similar, non-metastatic cell. In a detailed aspect, the disease state is neoplastic disease, solid tumor, hematological malignancy, leukemia, colorectal cancer, benign or malignant breast cancer, uterine cancer, uterine leiomyomas, ovarian cancer, endometrial cancer, polycystic ovary syndrome, endometrial polyps, prostate cancer, prostatic hypertrophy, pituitary cancer, adenomyosis, adenocarcinomas, meningioma, melanoma, bone cancer, multiple myeloma, CNS cancer, glioma, or astroblastoma. In a further detailed aspect, the neoplastic disease is tumor cell metastasis in the mammal or the neoplastic disease state is breast cancer metastasis in the mammal.

In a detailed embodiment, a method for treating a disease state in a mammal comprises administering to the mammal an antibody comprising SEQ ID NO: 2 or SEQ ID NO: 4. In a detailed aspect, the disease state is neoplastic disease, solid tumor, hematological malignancy, leukemia, colorectal cancer, breast cancer, uterine cancer, uterine leiomyomas, ovarian cancer, endometrial cancer, polycystic ovary syndrome, endometrial polyps, prostate cancer, prostatic hypertrophy, pituitary cancer, adenomyosis, adenocarcinomas, meningioma, melanoma, bone cancer, multiple myeloma, CNS cancer, glioma, or astroblastoma. In a further detailed aspect, the neoplastic disease is tumor cell metastasis in the mammal or the neoplastic disease state is breast cancer metastasis in the mammal.

In another embodiment, a cell line comprises a tumor cell variant with a metastatic homing propensity to a target tissue. In a further aspect, the tumor cell variant is derived from solid tumor, hematological malignancy, leukemia, colorectal cancer, breast cancer, uterine cancer, uterine leiomyomas, ovarian cancer, endometrial cancer, polycystic ovary syndrome, endometrial polyps, prostate cancer, prostatic hypertrophy, pituitary cancer, adenomyosis, adenocarcinomas, meningioma, melanoma, bone cancer, multiple myeloma, CNS cancer, glioma, or astroblastoma. In a further aspect, the target tissue is selected from brain, liver, lung, or bone.

In another embodiment a method of producing an antibody phage population having affinity for a tumor cell target, comprises providing a phage library derived from a blood lymphocyte cDNA library from a cohort of cancer patients, subtracting the phage library on a cell line expressing a non-metastatic phenotype, selecting a first antibody phage population that do not bind to the cell line expressing the non-metastatic phenotype, panning the first antibody phage population on a cell line expressing a metastatic phenotype, selecting a second antibody phage population that binds to the cell line expressing the metastatic phenotype, purifying an antibody phage clone that binds to the cell line expressing the metastatic phenotype and binds to the tumor cell target. In a further aspect, the cell line expressing the metastatic phenotype is a cell line expressing an activated cell surface receptor. In a further aspect, the activated cell surface receptor is an activated integrin receptor. In a detailed aspect, the activated cell surface receptor is an αvβ3 integrin receptor. In a further aspect, the cell line expressing the metastatic phenotype is a tumor cell variant with a metastatic homing propensity to a target tissue. In a further aspect, the target tissue is selected from brain, liver, lung, or bone. In a further detailed aspect, the tumor cell target is a metastatic cell. In a further detailed aspect, the metastatic cell is a metastatic breast tumor cell. In a further detailed aspect, the antibody phage population is a single chain (scFv) antibody phage population.

In a further embodiment the method further comprises testing the antibody phage clone for (a) binding to tumor cells expressing activated integrin receptor on a cell surface; and (b) reduced binding to tumor cells expressing non-activated integrin receptor on a cell surface.

In a further embodiment the method further comprises measuring binding efficiency of the antibody phage population for the cell line expressing activated integrin receptor increased in the presence of cations selected from $Ca^{++}$, $Mg^{++}$, or $Mn^{++}$.

In another embodiment, a method of detecting tumor cells in a mammal by treatment with a cancer therapeutic comprises linking a detectable marker to an antibody composition that specifically binds to an activated integrin receptor, contacting the detectable marker-antibody composition complex to the mammal or a mammalian tissue, detecting binding of the detectable marker-antibody composition complex to the tumor cell in the mammalian tissue. In a detailed aspect, the tumor cells are metastatic tumor cells.

In another embodiment, a method for inducing or enhancing an immune response to an antigen in a mammal comprises administering to the mammal an antibody to a cell surface receptor on a metastatic cell such that plasma concentration of the anti-cell surface receptor antibody is maintained above detectable levels for at least four months. In a further embodiment, the cell surface receptor is an activated integrin receptor. In a further embodiment, the activated integrin receptor is an αvβ3 integrin receptor. In a further aspect, the anti-cell surface receptor antibody is administered multiple times such that plasma concentration is maintained above detectable levels for at least four months. In a further aspect, the anti-cell surface receptor antibody is administered in an amount and at intervals such that the plasma concentration of the anti-integrin receptor antibody in the mammal is at least 2 µg/ml for at least four months, or at least 5 µg/ml for at least four months or at least 10 µg/ml for at least four months. In a detailed aspect, the mammal is a human. In a further detailed aspect, the antibody to an activated integrin receptor is a human anti-activated integrin receptor antibody. In a further detailed aspect, the antibody to an activated integrin receptor is a humanized anti-activated integrin receptor antibody. In a further detailed aspect, the antibody to an activated integrin receptor is a human sequence anti-activated integrin receptor antibody.

In another embodiment, a method for treating a mammal for a metastatic cancer disease, comprises administering to the mammal an antibody to a cell surface receptor on a metastatic cell linked to a cytotoxic agent such that the mammal is treated for the metastatic cancer disease. In a further embodiment, the cell surface receptor is an activated integrin receptor. In a further aspect, the cytotoxic agent is a cytotoxic drug. In a further aspect, the cytotoxic agent is a radioactive isotope.

In another embodiment, a method of detecting an activated cell surface receptor on a metastatic tumor cell surface in a mammalian tissue sample, comprises contacting the mammalian tissue with a first human antibody immobilized to a solid phase, and a second human antibody in solution, wherein the first and second antibodies bind to different epitopes of the activated cell surface receptor if present in the tissue sample; detecting binding of the activated cell surface receptor to the first and second antibodies, binding indicating presence of the activated cell surface receptor in the tissue sample; wherein the first and second human antibodies are produced by subcloning nucleic acids encoding the first and second human antibodies provided by a phage library derived from a blood lymphocyte cDNA library from a cohort of cancer patients, subtracting the phage library on a cell line expressing a non-metastatic phenotype; selecting a first antibody phage population that do not bind to the cell line expressing the non-metastatic phenotype; panning the first antibody phage population on a cell line expressing a metastatic phenotype; selecting a second antibody phage population that binds to the cell line expressing the metastatic phenotype; purifying an antibody phage clone that binds to the cell line expressing the metastatic phenotype and binds to the tumor cell target.

In a detailed embodiment, the activated cell surface receptor is an activated integrin receptor. In another detailed embodiment, the activated integrin receptor is an $\alpha v \beta 3$ integrin receptor. In another embodiment, the second antibody is labelled and wherein the detecting step detects binding of the second antibody to the activated cell surface receptor.

In another further embodiment, the tissue sample is contacted with a first population of human antibodies immobilized to the solid phase and a second population of human antibodies in solution, wherein members from the first and second populations bind to different epitopes on the activated cell surface receptor. In another detailed aspect, the second population of human antibodies is labeled. In another further aspect, the first and second human antibodies each have an affinity of at least $10^9$ $M^{-1}$ for their respective epitopes on the activated cell surface receptor. In another detailed aspect, the first and second human antibodies each have an affinity of at least $10^{10}$ $M^{-1}$ for the activated cell surface receptor. In another detailed aspect, the first and second human antibodies have an affinity of a least $10^{11}$ $M^{-1}$ for the activated cell surface receptor. In a further embodiment, the binding of the first and second human antibodies to the activated cell surface receptor reaches equilibrium within an hour. In another detailed embodiment, the first and second human antibodies were produced by expression by expression of recombinant constructs in E. coli. In another detailed aspect, at least 90% of molecules of the first and second antibody are immunoreactive with the activated cell surface receptor.

In a further embodiment, a method of interfering with cells liable to undergo metastasis associated with a disease state comprises contacting a patient suspected of being at risk for metastasis with an antibody which specifically binds to an activated $\alpha v \beta 3$ integrin receptor which is differentially produced on a cell in a metastatic state compared to a similar, non-metastatic cell, the antibody having associated therewith a cytotoxic moiety. In a detailed embodiment, the antibody composition comprises SEQ ID NO: 2. In a further detailed embodiment, the antibody composition comprises SEQ ID NO: 4. In another detailed embodiment, the cytotoxic moiety is a chemical toxin. In further detailed embodiment, the cytotoxic moiety is a biological toxin. In another detailed embodiment, the cytotoxic moiety is a radioactive agent. In further detailed embodiment, the association is a covalent bond. In another detailed embodiment, the association is a ligand interaction. In a further detailed embodiment, the association is a physical interaction. In a further detailed embodiment, the association comprises containment within a vessel. In another detailed embodiment, the vessel is a liposome or other blood circulating vessel.

In a further embodiment, a method of identifying cells liable to undergo metastasis associated with a disease state comprises contacting a patient suspected of being at risk for metastasis with an antibody which specifically binds to an activated $\alpha v \beta 3$ integrin receptor which is differentially produced on a cell in a metastatic state compared to a similar, non-metastatic cell, the antibody having associated therewith an imaging moiety. In a further embodiment, the imaging moiety can be imaged through magnetic resonance spectroscopy, X-ray spectroscopy, or positron emission tomography (PET). In a detailed embodiment, the association is a covalent bond. In a further detailed embodiment, the association is a non-covalent bond.

A method for treating a mammal for a metastatic cancer disease is provided which comprises administering to the mammal an antibody to a cell surface receptor on a metastatic cell, and inducing programmed cell death of the metastatic cell, such that the mammal is treated for said metastatic cancer disease. In one aspect, the cell surface receptor is an activated integrin receptor. In a further aspect, the activated integrin receptor is an $\alpha v \beta 3$ integrin receptor.

The present invention provides an isolated Bc-12 polynucleotide comprising a nucleotide sequence that has at least 90% percent identity to SEQ ID NO: 1. The present invention further provides an isolated polypeptide comprising a nucleotide sequence that has at least 90% sequence identity to SEQ ID NO: 1 or shares a biological function with Bc-12. In a detailed aspect, a vector comprises the isolated Bc-12 polynucleotide with at least 90% percent identity to SEQ ID NO: 1. In a detailed aspect, an expression vector comprising the isolated Bc-12 polynucleotide with at least 90% percent identity to SEQ ID NO: 1 in which the nucleotide sequence of the polynucleotide is operatively linked with a regulatory sequence that controls expression of the polynucleotide in a host cell. In a detailed aspect, a host cell comprising the isolated Bc-12 polynucleotide with at least 90% percent identity to SEQ ID NO: 1, or progeny of the cell. In a further aspect, an isolated Bc-12 polypeptide comprises the amino acid sequence that has at least 90% identity to SEQ ID NO: 2.

The present invention provides an isolated Bc-15 polynucleotide comprising a nucleotide sequence that has at least 90% percent identity to SEQ ID NO: 3. The present invention further provides an isolated polypeptide comprising a nucleotide sequence that has at least 90% sequence identity to SEQ ID NO: 3 or shares a biological function with Bc-15. In a detailed aspect, a vector comprises the isolated Bc-15 polynucleotide with at least 90% percent identity to SEQ ID NO: 3. In a detailed aspect, an expression vector comprising the isolated Bc-15 polynucleotide with at least 90% percent identity to SEQ ID NO: 3 in which the nucleotide sequence of the polynucleotide is operatively linked with a regulatory sequence that controls expression of the polynucleotide in a host cell. In a detailed aspect, a host cell comprising the isolated Bc-15 polynucleotide with at least 90% percent identity to SEQ ID NO: 3, or progeny of the cell. In a further aspect, an isolated Bc-15 polypeptide comprises the amino acid sequence that has at least 90% identity to SEQ ID NO: 4.

A method for determining anti-metastatic activity of a test compound in a mammal is provided which comprises administering to the mammal a tumor cell variant with a metastatic homing propensity to a target tissue, administering the test compound to the mammal, measuring anti-metastatic activity of the test compound in the mammal compared to anti-metastatic activity of a control compound in a control mammal. In a further embodiment the method comprises measuring metastatic foci in the target tissue of the mammal, wherein a reduction in metastatic foci in the mammal in response to the test compound compared to metastatic foci in a control animal in response to a control compound indicates the anti-metastatic activity of the test compound. In one aspect, the tumor cell variant and the test compound are administered to the peripheral blood circulation of the mammal. In a further aspect, the tumor cell variant and the test compound are administered orthotopically into the mammary fat pad of the mammal. In a detailed aspect, the tumor cell variant is BCM-1, BCM-2 or BMS. In a further aspect, the test compound is an antibody, a single chain Fv antibody, a small molecule, an antisense oligonucleotide, double stranded RNA molecule, short interfering RNA (siRNA,) or short hairpin RNA (shRNA). In a further embodiment, the mammal is a non-human mammal, for example, a rodent, rabbit, canine, feline, or non-human primate. In a further detailed embodiment the mammal is a mouse or an immune deficient mouse.

BRIEF DESCRIPTION OF THE DRAWINGS

FIGS. 2A, 2B, 2C, 2D. Translation of scFv DNA sequence analyses. (A) Consensus amino acid sequence (SEQ ID NO: 9) of Bc-12 (SEQ ID NO: 7) and Bc-15 (SEQ ID NO: 8) (specific for activated $\alpha v\beta 3$) compared to Bc-20 (specific for $\alpha v$) (SEQ ID NO: 10). (B) scFv binding to BMS human breast cancer cells by flow cytometry, indicating loss of Bc-12 and Bc-15 binding when CDR-H3 RGD is mutated to RGE (Mut-12 and Mut-15). Mut-15 signal is equivalent to negative control. (C) cDNA sequences for scFv Bc-12 (SEQ ID NO: 1) and scFv Bc-15 (SEQ ID NO: 3). The cDNA encoding scFv Bc-12 has an ATCC accession number PTA-6303, date of deposit: Nov. 12, 2004. The cDNA encoding scFv Bc-15 has an ATCC accession number PTA-6304, date of deposit: Nov. 12, 2004. (D) cDNA sequences for scFv Mut-12 (SEQ ID NO: 5) and scFv Mut-15 (SEQ ID NO: 6). scFv Mut-12 is the RGE containing mutant version of scFv Bc-12. scFv Mut-15 is the RGE containing mutant version of scFv Bc-15.

DETAILED DESCRIPTION

Figure 1:
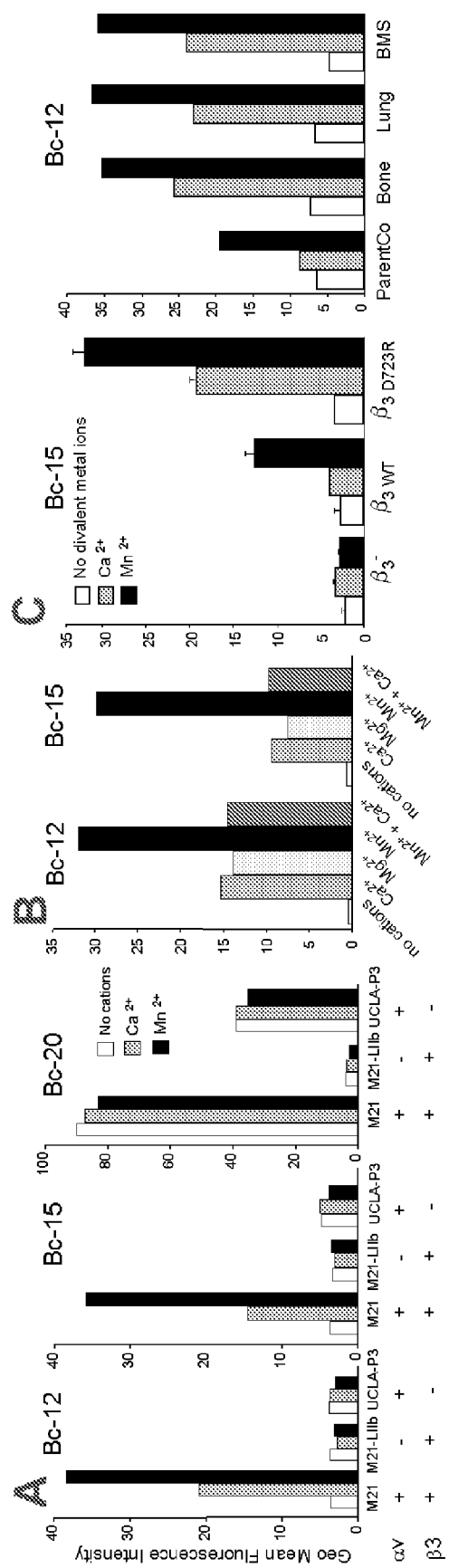
FIGS. 1A, 1B, 1C. Patient derived scFvs Bc-12 and Bc-15 recognize tumor cell integrin $\alpha v\beta 3$ in a cation and activation dependent manner. Flow cytometric analyses in TBS with or without 1 mM $Ca^{2+}$, 1 mM $Mg^{2+}$, or 0.2 mM $Mn^{2+}$ as indicated. Binding of soluble scFv detected after incubation with anti-Flag M2 murine mAb followed by FITC-anti mouse F(ab')$_2$. (A) scFv binding to human melanoma cells (M21: $\alpha v\beta 3$ plus other $\alpha v$ integrins) (M21-LIIb: $\alpha IIb\beta 3$, no $\alpha v$ integrins) or lung adenocarcinoma cells (UCLA-P3: $\alpha v$ integrins, no $\beta 3$ integrin). (B) scFv binding to M21 melanoma cells. (C) scFv binding to variants of MDA-MB 435 human breast cancer cells that lack ($\beta 3^-$) or express $\alpha v\beta 3$ either in a non-activated ($\beta 3_{WT}$, ParentCo) or activated form ($\beta 3_{D723R}$, Bone, Lung, and BMS metastatic cancer cells isolated from breast cancer patient blood). Similar results were obtained in several independent experiments for Bc-12 and Bc-15 on each of these cell types.

The invention is generally related to methods of producing an antibody phage population having affinity for a tumor cell target which is a tumor cell expressing a metastatic phenotype. The tumor cell expressing the metastatic phenotype can be a cell line expressing an activated cell surface receptor, for example, an activated integrin receptor or an αvβ3 integrin receptor. The invention further relates to an antibody composition that specifically binds to a cell surface receptor on a metastatic cell. The antibody composition specifically binds to a activated cell surface receptor on a metastatic cell, for example, an activated integrin receptor or an αvβ3 integrin receptor. The invention further relates to methods for alleviating a disease state in a mammal by treatment with a cancer therapeutic comprising the step of administering to the mammal a therapeutic amount of said pharmaceutical composition of the antibody composition. The invention further relates to methods of detecting an activated cell surface receptor on a metastatic tumor cell surface in a mammalian tissue sample and to methods of identifying cells liable to undergo metastasis associated with a disease state comprising contacting a patient suspected of being at risk for metastasis which includes contacting a patient suspected of being at risk for metastasis with the antibody composition, said antibody having associated therewith an imaging moiety.

It has now been discovered that an activated functional form of αvβ3 integrin can be used as a target in a therapeutic regime for the inhibition of cancer metastasis, especially in breast cancer metastasis. Human single-chain Fv antibody libraries of cancer patient immune repertoire has been developed containing antibodies that can recognize αvβ3 integrin specifically in its activated form. The present invention provides isolation, characterization and in vivo use of these antibodies to disrupt the activated form of αvβ3 and prevent breast cancer metastasis.

Although breast tumors can be detected at ever smaller size, one cannot presently predict when these will begin to metastasize and to inhibit this process effectively. To improve the therapeutic potential of surgery and anti-cancer treatment, new molecular targets are needed to identify and inhibit metastatic cells. Studies, in vitro and in vivo, with human breast cancer cell models and metastatic cells from breast cancer patients demonstrate that expression of activated cell surface receptors on metastatic cells, e.g., the adhesion receptor integrin αvβ3 in a functionally activated form, strongly promotes metastatic activity. To exploit this metastasis related expression, selection of cancer patient derived human single-chain Fv antibody libraries yielded antibodies that specifically recognize the activated form of αvβ3 and block critical functions of this receptor. Two of these antibodies, Bc-12 and Bc-15, were found to be natural ligand mimetics that bind αvβ3 in a cation dependent manner via an Arg-Gly-Asp integrin recognition motif within CDR-H3. These antibodies, but not their Arg-Gly-Glu mutants, interfered with αvβ3 mediated tumor cell adhesion and migration, specifically recognized metastatic breast cancer cells in blood, and inhibited platelet supported tumor cell arrest during blood flow. Importantly, scFvs Bc-12 and Bc-15 prevented lung colonization by human breast cancer cells in immune deficient mice. These data imply that disrupting the functions of activated αvβ3 can inactivate tumor cells in the circulation and thus prevent breast cancer metastasis.

There is an absence of reagents available which recognize murine αvβ3 integrin receptor. Having access to such a reagent would offer the scientific community a valuable research reagent. Based on the nature of the scFvs disclosed herein, it is anticipated that Bc-12 and Bc-15 could react with murine αvβ3 integrin receptor. If they do, these reagents would be very helpful for use in vivo studies utilizing mouse models of human disease states. Murine αvβ3 integrin receptor reagents would be of particular use for angiogenesis-based studies which are performed to a large degree in mouse models. It is expected that the scFvs of the invention react with activated murine αvβ3 integrin receptor on angiogenic endothelial cells, possibly in a murine model and very likely in humans.

ScFvs Bc-12 and Bc-15 are novel reagents because they selectively bind to the activated conformation of αvβ3 integrin receptor and do not bind to the non-activated conformation of αvβ3 integrin receptor. Amongst tumor cells expressing the αvβ3 integrin receptor that have been tested so far, only cells with a metastatic phenotype express αvβ3 integrin receptor in a constitutively activated conformation.

Surprisingly, scFvs Bc-12 and Bc-15 utilize an RGD ligand motif (CDR-H3) combined with high specificity for αvβ3 integrin receptor. Other known antibodies containing the RGD motif react with multiple integrins that recognize the RGD sequence. As demonstrated herein, scFv Bc-12 and Bc-15 do not bind to other integrins known as major receptors for the RGD motif, including, but not limited to, integrin αvβ5, αvβ1, alpha IIb beta 3, and α5β1.

Breast cancers are known to be extremely heterogeneous. A subset of human breast cancer cells can be identified based on expression of an adhesion receptor, the integrin αvβ3, in its constitutively activated functional form. This activated integrin promotes platelet binding and tumor cells arrest in the vasculature. In this way, activation of integrin αvβ3 endows metastatic cells with key properties likely to be critical for successful dissemination and colonization of target organs. The combined immune repertoire of a number of cancer patients has been mined using antibody phage display technology by subtractive panning on poorly versus strongly metastatic variants of a human breast cancer cell line. This approach yielded single chain Fv (scFv) antibodies that specifically recognize the activated functional conformation of the tumor cell adhesion receptor, integrin αvβ3. The antibodies react selectively with metastatic variants of the breast cancer cell models and with metastatic cells isolated from blood samples of stage IV breast cancer patients. Importantly, these antibodies inhibit colonization of the lungs by human breast cancer cells in immune deficient mice.

Antibody compositions and methods of the present invention are useful to investigate the ability of human single chain Fv (scFv) antibodies to report the activated form of integrin αvβ3 as a diagnostic marker of metastatic cancer cells, e.g., metastatic breast cancer cells. These scFv antibodies and their derivatives can specifically detect metastatic breast cancer cells and report the localization of metastatic disease. Antibody compositions and methods of the present invention are further useful to identify therapeutic antibody compositions for treatment of cancer metastasis, e.g., metastatic breast cancer.

Antibody compositions and methods of the present invention are useful to investigate the ability of human single chain Fv (scFv) antibodies to detect and report the activated form of integrin αvβ3 as a prognostic marker of metastatic breast cancer. These scFv antibodies and their derivatives can specifically detect breast cancer cells that have a propensity to metastasize.

Antibody compositions and methods of the present invention are useful to analyze effects of human scFv antibodies and their derivatives against constitutively activated integrin αvβ3 on breast cancer metastasis. Targeted inhibition of cells expressing the activated form of integrin αvβ3 can prevent breast cancer metastasis and interfere with established metastatic disease.

Imaging and mammography technology can detect very early breast tumors. However, current prognostic criteria for breast cancer do not accurately indicate how aggressive a tumor is, whether it has already begun to spread, and which treatment options should be chosen to achieve the best possible outcome in each individual case. Complications from metastatic disease are the primary cause of death in breast cancer. Breast cancer metastasis to major target organs, such as lungs, bone, liver, and brain involves tumor cell dissemination via the blood stream. An important requirement for successful target organ colonization in this environment is the ability of the tumor cells to arrest within the vasculature of their target organs, despite shear forces generated by blood flow which physically opposed cell attachment. One mechanism supporting the arrest process has been identified as an interaction between the tumor cell adhesion receptor, integrin αvβ3, and platelet integrin αIIbβ3, connected to each other by di- or multivalent plasma proteins as bridging ligands. Felding-Habermann et al., *J. Biol. Chem.*, 271: 5892-5900, 1996; Pilch et al., *J. Biol. Chem.*, 277: 21930-21938, 2002; Felding-Habermann et al, *Proc. Natl. Acad. Sci. U.S.A*, 98: 1853-1858, 2001; Bakewell et al., *Proc. Natl. Acad. Sci. U.S.A*, 100: 14205-14210, 2003; Biggerstaff et al., *Clin. Exp. Metastasis*, 17: 723-730, 1999.

Integrins are a family of transmembrane cell adhesion receptors that are composed of α and β subunits and mediate cell attachment to proteins within the extracellular matrix. In addition to recognizing ligand proteins immobilized within a matrix, the receptors may also react with soluble ligand proteins, for instance certain plasma proteins, but only if the receptor molecules are present in an activated functional conformation. Liddington et al., *J. Cell Biol.*, 158: 833-839, 2002; Woodside et al., *Thromb. Haemost.*, 86: 316-323, 2001. Thus, recognition of soluble ligands by integrins strictly depends on specific changes in receptor conformation. This provides a molecular switch that controls the ability of cells to aggregate in an integrin dependent manner and to arrest under the dynamic flow conditions of the vasculature. This mechanism is well established for leukocytes and platelets, that circulate within the blood stream in a resting state while expressing non-activated integrins. Upon stimulation through proinflammatory or prothrombotic agonists, these cell types promptly respond with a number of molecular changes including the switch of key integrins, β2 integrins for leucocytes and αvβ3 for platelets, from 'resting' to 'activated' conformations. This enables these cell types to arrest within the vasculature, promoting cell cohesion and leading to thrombus formation. Savage et al., *Curr. Opin. Hematol.*, 8: 270-276, 2001. It has demonstrated that a metastatic subset of human breast cancer cells expresses integrin αvβ3 in a constitutively activated form. Rolli et al., *Proc. Natl. Acad. Sci. U.S.A*, 100: 9482-9487, 2003. Aberrant expression of αvβ3 plays a role in metastasis of breast cancer as well as prostate cancer, melanoma, and neuroblastic tumors, but it is important to understand that it is specifically the activated functional conformation of the receptor that promotes metastatic activity. Felding-Habermann et al, *Proc. Natl. Acad. Sci. U.S.A*, 98: 1853-1858, 2001; Felding-Habermann et al., *Clin. Exp.-Metastasis*, 19: 427-436, 2002; Gladson et al., *Am. J. Pathol.*, 148: 1423-1434, 1996; Zheng et al., *Cancer Res.*, 59: 1655-1664, 1999; Zheng et al., *J. Biol. Chem.*, 275: 24565-24574, 2000; Van Belle et al., *Hum. Pathol.*, 30: 562-567, 1999; Gui et al., *Surgery*, 117: 102-108, 1995. The activated receptor strongly promotes breast cancer cell migration and enables the cells to arrest under blood flow conditions. In this way, activation of αvβ3 endows metastatic cells with key properties likely to be critical for successful dissemination and colonization of target organs. Integrin mediated tumor cell-platelet interactions have been implicated in metastasis to lung and bone and it has been suggested that, in addition to enabling arrest in the circulation, platelet coating of tumor cells may prevent immune recognition by cloaking tumor antigens, or may supply the tumor cells with growth factors such as epidermal growth factor or platelet derived growth factor. Biggerstaff et al., *Clin. Exp. Metastasis*, 17: 723-730, 1999; Felding-Habermann et al., *Clin. Exp. Metastasis*, 19: 427-436, 2002; Amirkhosravi et al., *Thromb. Haemost.*, 90: 549-554, 2003; Siddiqui et al., *Platelets*, 13: 247-253, 2002; Furger, K. A., et al., *Mol. Cancer Res.*, 1: 810-819, 2003. Tumor cells that have successfully entered a target organ may further utilize αvβ3 to thrive in the new environment, as αvβ3 matrix interactions can promote cell survival and proliferation. For example, αvβ3 binding to osteopontin, a bone matrix protein, promotes malignancy and elevated levels of osteopontin correlate with a poor prognosis in breast cancer. Zheng et al., *J. iol. Chem.*, 275: 24565-24574, 2000; Singhal et al., *Clin. Cancer Res.*, 3: 605-611, 1997; Tuck et al., *Int. J. Cancer*, 79: 502-508, 1998; Rudland et al., *Cancer Res.*, 62: 3417-3427, 2002; Ding et al., *Cancer Res.*, 62: 5336-5343, 2002; Wang et al., *Oncogene*, 19: 5801-5809, 2000; Gladson et al., *J. Neuropathol. Exp. Neurol.*, 58: 1029-1040, 1999.

For all of these reasons, and its established role in angiogenesis the αvβ3 integrin is one of the most widely studied integrins and antagonists of this molecule have significant potential to serve as diagnostic imaging agents and for use in targeted drug delivery. Bakewell et al., *Proc. Natl. Acad. Sci. U.S.A*, 100: 14205-14210, 2003; Varner et al.,. *Important. Adv. Oncol.*, 69-87: 69-87, 1996; Tucker et al., *Curr. Opin. Investig. Drugs*, 4: 722-731, 2003. Two separate approaches have been used to target this molecule. One of these uses the high binding specificity to αvβ3 of peptides containing the Arg-Gly-Asp (RGD) sequence. This tripeptide, naturally present in extracellular matrix proteins, is the primary binding site of the αvβ3 integrin. Ruoslahti et al., *Annu. Rev. Cell Dev. Biol.*, 12: 697-715, 1996. Initial problems with RGD based reporter probes are due to fast blood clearance, high kidney and liver uptake and fast tumor washout, currently being addressed by chemically modifying cyclised RGD peptides to increase their stability and valency. Menard et al., *Oncogene*, 22: 6570-6578, 2003; Chen et al., *Bioconjug. Chem.*, 15: 41-49, 2004; Thumshirn et al., *Chemistry.*, 9: 2717-2725, 2003; Su et al., *Nucl. Med. Biol.*, 30: 141-149, 2003. These modified peptides are then coupled to radio-isotpes and used either for tumor imaging or to inhibit tumor growth. One such molecule, Cilengitide, is currently in Phase II clinical trials to inhibit tumor progression. The other approach uses antibodies, either alone or as immunoconjugates. Attempts to develop monoclonal antibodies (mAbs) as therapeutic agents for cancer patients have intensified the search for cancer-related antigens as molecular targets. Function blocking antibodies against integrin αvβ3, especially mAb LM609 and its derivatives, have been shown to interfere with critical adhesive tumor cell functions and neoangiogenesis. Brooks et al., *Cell*, 79: 1157-1164, 1994; Brooks et al., *Science*, 264: 569-571, 1994. It was earlier found that LM609 antibody also inhibited metastatic activity of human melanoma cells in a mouse model. Felding-Habermann et al., *Clin. Exp. Metastasis*, 19: 427-436, 2002. Antibodies recognizing tumor cells or supporting host cells have been used in immunoradiotherapy and radioimmunolocalization, as well as toxin and chemotherapeutic agent delivery. Goldenberg, *Cancer Immunol. Immunother.*, 52: 281-296, 2003; Power et al., *Methods Mol. Biol.*, 207: 335-350, 2003; Kortt et al., *Biomol. Eng*, 18: 95-108, 2001; Garnett *Adv. Drug Deliv. Rev.*, 53: 171-216, 2001. Advances in immunoconjugate technology, together with the availability of fully human antibodies have revitalized the "magic bullet" promise of immunotherapy for cancer treatment. In the past few years, several mAbs received FDA approval for cancer treatment. These include Rituximab, a chimeric antibody against CD20 for the treatment of non-Hodgkin's lymphoma, and Trastuzumab (Herceptin), a murine and now humanized antibody against the Her-2 proto oncogene protein for the treatment of metastatic breast cancer. Menard et al., *Oncogene*, 22: 6570-6578, 2003; Smith, *Oncogene*, 22: 7359-7368, 2003; Perez. et al., *J. Clin. Oncol.*, 22: 322-329, 2004; Spigel et al., *Clin. Breast Cancer*, 4: 329-337, 2003; Ali, *Clin. Orthop.*, S132-S 137, 2003. A list of therapeutic mAbs currently 'in the pipeline' for treatment of breast cancer, and mAbs selected for testing in new clinical trials in combination with chemotherapeutic or other regimens are summarized in tables presented in the appendix. Results of clinical trials with single agent Trastuzumab (anti-Her-2) and in combination with paclitaxel, docetaxel, vinorelbine, gemcitabine and platinum salts have been encouraging, and durable remissions (>5 years) have been reported occasionally. However, none of the current therapies, including chemo- and antibody based treatments, could effectively stop or prevent metastasis. Thus, enhancement of existing treatment options by improved antibody therapy, specifically identifying or targeting metastatic cells would have a major impact on breast cancer management and diagnosis.

To identify target molecules associated with metastatic human breast cancer cells, and to isolate antibodies of human origin directed against such markers, the combined immune repertoire of a number of cancer patients was mined using antibody phage display technology. This approach yielded single chain Fv (scFv) antibodies that recognize the tumor cell adhesion receptor, integrin αvβ3, but only in its activated functional conformation. The antibodies react selectively with metastatic variants of the breast cancer cell models and with metastatic cells isolated from blood samples of stage IV breast cancer patients. Importantly, these antibodies inhibit colonization of the lungs by human breast cancer cells in immune deficient mice. These antibodies act as ligand mimetics. They contain the RGD integrin recognition sequence which contributes to their affinity. However, they also demonstrate the ligand specificity of an antibody-antigen interaction. In this way, they offer the possibility of combining the advantages of both of the above therapeutic approaches.

ScFv fragments have several distinct advantages over whole IgG for cancer immunotherapy. First, due to their relatively small size (27 kDa), scFvs clear from plasma readily and can penetrate rapidly and deeply into tissue. Garnett, *Adv. Drug Deliv. Rev.*, 53: 171-216, 2001. For example, $^{125}$I-labeled anti-CEA (carcino embryonic antigen) scFv showed superior tumor localization compared to whole IgG. Wu et al., *Immunotechnology.*, 2: 21-36, 1996; Mayer et al., *Clin. Cancer Res.*, 6: 1711-1719, 2000. Second, potential side effects may be reduced, since lack of the constant region ensures that scFvs are not retained in organs with high density of cells expressing Fc receptors, like the liver and/or kidney. Third, scFvs can be re-engineered with PCR based approaches into several different formats such as diabody, triabody, or bispecific antibody so that the size, flexibility and valency of each antibody fragment can be tailored to suit specific applications for in vivo imaging and therapy. Kortt et al., *Biomol. Eng*, 18: 95-108, 2001. These scFv antibodies are often internalized by tumors following antigen engagement and can be conjugated to highly toxic, small molecules. In addition these antibody fragments have been reported to be capable of crossing the blood-brain barrier. Frenkel et al., *Proc. Natl. Acad. Sci. U.S.A*, 99: 5675-5679, 2002. Brain metastases present a particularly intractable problem in breast and other cancers and therapeutic advances in this area would have a very significant impact.

Another application addresses the concept that breast tumors contain a minor, distinct, sub-population of progenitor- or stem- like cells that are responsible for the initiation of the tumor. Al Hajj, *Proc. Natl. Acad. Sci. U.S.A*, 100: 3983-3988, 2003.

A library of scFv antibodies to integrins can be used to define the characteristics that would allow one to prospectively identify the putative tumor initiating population in human breast cancer. In other organ systems, stem cells occupy a basal compartment, adhering to the underlying basement membrane via integrins. Integrin expression patterns have been found to differ between the stem cells and their differentiated progeny. In prostate epithelium, spermatogenesis and epidermal keratinocytes, β1 integrin expression has been used to identify and isolate populations of putative stem cells. Collins et al., *J. Cell Sci.*, 114: 3865-3872, 2001; Shinohara et al., *Proc. Natl. Acad. Sci. U.S.A*, 96: 5504-5509, 1999; Evans et al., *J. Cell Biol.*, 160: 589-596, 2003. Integrin expression can be used as a marker for breast tumor initiating populations. The library of scFv antibodies contains several antibodies against distinct activation states of different integrins. In an alternative approach, the library of scFv antibodies to integrins can be used to define integrin expression and other markers and ultimately to target this cell population.

scFV Phage Libraries

One approach for a phage display library to identify an antibody composition that specifically binds to a cell surface receptor on a metastatic cell, for example, an activated integrin receptor, has been the use of scFv phage-libraries (see, e.g., Huston et al., *Proc. Natl. Acad. Sci U.S.A.*, 85: 5879-5883, 1988; Chaudhary et al., *Proc. Natl. Acad. Sci U.S.A.*, 87: 1066-1070, 1990. Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys), which are incorporated herein by reference. The display of Fab libraries is also known, for instance as described in WO92/01047 (CAT/MRC) and WO91/17271 (Affymax).

Hybrid antibodies or hybrid antibody fragments that are cloned into a display vector can be selected against the appropriate antigen associated with a metastatic cell, e.g., a cell surface receptor or an activated cell surface receptor on a metastatic tumor cell, in order to identify variants that maintained good binding activity because the antibody or antibody fragment will be present on the surface of the phage or phagemid particle. See for example Barbas III et al., *Phage Display, A Laboratory Manual*, Cold Spring Harbor Laboratory Press, Cold Spring Harbor, N.Y., 2001, the contents of which are incorporated herein by reference. For example, in the case of Fab fragments, the light chain and heavy chain Fd products are under the control of a lac promoter, and each chain has a leader signal fused to it in order to be directed to the periplasmic space of the bacterial host. It is in this space that the antibody fragments will be able to properly assemble. The heavy chain fragments are expressed as a fusion with a phage coat protein domain which allows the assembled antibody fragment to be incorporated into the coat of a newly made phage or phagemid particle. Generation of new phagemid particles requires the addition of helper phage which contain all the necessary phage genes. Once a library of antibody fragments is presented on the phage or phagemid surface, a process termed panning follows. This is a method whereby) the antibodies displayed on the surface of phage or phagemid particles are bound to the desired antigen, ii) non-binders are washed away, iii) bound particles are eluted from the antigen, and iv) eluted particles are exposed to fresh bacterial hosts in order to amplify the enriched pool for an additional round of selection. Typically three or four rounds of panning are performed prior to screening antibody clones for specific binding. In this way phage/phagemid particles allow the linkage of binding phenotype (antibody) with the genotype (DNA) making the use of antibody display technology very successful. However, other vector formats could be used for this humanization process, such as cloning the antibody fragment library into a lytic phage vector (modified T7 or Lambda Zap systems) for selection and/or screening.

After selection of desired hybrid antibodies and/or hybrid antibody fragments, it is contemplated that they can be produced in large volume by any technique known to those skilled in the art, e.g., prokaryotic or eukaryotic cell expression and the like. For example, hybrid antibodies or fragments may be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which may be manipulated as described herein, thereby producing a vector for the expression of a hybrid antibody heavy chain.

In a detailed embodiment, a single-chain Fv (scFv) antibody library can be prepared from the peripheral blood lymphocytes of 5, 10, 15, or 20 or more patients with various cancer diseases. Completely human high-affinity scFv antibodies can then be selected by using synthetic sialyl Lewis$^x$ and Lewis$^x$ BSA conjugates. In one study, these human scFv antibodies were specific for sialyl Lewis$^x$ and Lewis$^x$, as demonstrated by ELISA, BIAcore, and flow cytometry binding to the cell surface of pancreatic adenocarcinoma cells. Nucleotide sequencing revealed that at least four unique scFv genes were obtained. The $K_d$ values ranged from 1.1 to $6.2 \times 10^{-7}$ M that were comparable to the affinities of mAbs derived from the secondary immune response. These antibodies could be valuable reagents for probing the structure and function of carbohydrate antigens and in the treatment of human tumor diseases. Mao et al., *Proc. Natl. Acad. Sci. U.S.A.* 96: 6953-6958, 1999.

In a further detailed embodiment, phage displayed combinatorial antibody libraries can be used to generate and select a wide variety of antibodies to an appropriate antigen associated with a metastatic cell, e.g., a cell surface receptor or an activated cell surface receptor on a metastatic tumor cell. The phage coat proteins pVII and pIX can be used to display the heterodimeric structure of the antibody Fv region. Aspects of this technology have been extended to construct a large, human single-chain Fv (scFv) library of $4.5 \times 10^9$ members displayed on pIX of filamentous bacteriophage. Furthermore, the diversity, quality, and utility of the library were demonstrated by the selection of scFv clones against six different protein antigens. Notably, more than 90% of the selected clones showed positive binding for their respective antigens after as few as three rounds of panning. Analyzed scFvs were also found to be of high affinity. For example, kinetic analysis (BIAcore) revealed that scFvs against staphylococcal enterotoxin B and cholera toxin B subunit had a nanomolar and subnanomolar dissociation constant, respectively, affording affinities comparable to, or exceeding that, of mAbs obtained from immunization. High specificity was also attained, not only between very distinct proteins, but also in the case of more closely related proteins, e.g., *Ricinus communis* ("ricin") agglutinins ($RCA_{60}$ and $RCA_{120}$), despite >80% sequence homology between the two. The results suggested that the performance of pIX-display libraries can potentially exceed that of the pIII-display format and make it ideally suited for panning a wide variety of target antigens. Gao et al., *Proc. Natl. Acad. Sci. U.S.A.* 99: 12612-12616, 2001.

Specific binding between an antibody or other binding agent and an antigen means a binding affinity of at least $10^{-6}$ M. Preferred binding agents bind with affinities of at least about $10^{-7}$ M, and preferably $10^{-8}$ M to $10^{-9}$ M, $10^{-10}$ M, $10^{-11}$ M, or $10^{-12}$ M. The term epitope means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

"Patient", "subject" or "mammal" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

"Treating" or "treatment" includes the administration of the antibody compositions, compounds or agents of the present invention to prevent or delay the onset of the symptoms, complications, or biochemical indicia of a disease, alleviating the symptoms or arresting or inhibiting further development of the disease, condition, or disorder (e.g., cancer, metastatic cancer, or metastatic breast cancer). Treatment can be prophylactic (to prevent or delay the onset of the disease, or to prevent the manifestation of clinical or subclinical symptoms thereof) or therapeutic suppression or alleviation of symptoms after the manifestation of the disease.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancerous" or "malignant cell" is understood as a cell having specific structural properties, lacking differentiation and being capable of invasion and metastasis. Examples of cancers are, breast, lung, brain, bone, liver, kidney, colon, and prostate cancer. (see DeVita et al., Eds., *Cancer Principles and Practice of Oncology*, 6th. Ed., Lippincott Williams & Wilkins, Philadelphia, Pa., 2001; this reference is herein incorporated by reference in its entirety for all purposes).

"Cancer-associated" refers to the relationship of a nucleic acid and its expression, or lack thereof, or a protein and its level or activity, or lack thereof, to the onset of malignancy in a subject cell. For example, cancer can be associated with expression of a particular gene that is not expressed, or is expressed at a lower level, in a normal healthy cell. Conversely, a cancer-associated gene can be one that is not expressed in a malignant cell (or in a cell undergoing transformation), or is expressed at a lower level in the malignant cell than it is expressed in a normal healthy cell.

In the context of the cancer, the term "transformation" refers to the change that a normal cell undergoes as it becomes malignant. In eukaryotes, the term "transformation" can be used to describe the conversion of normal cells to malignant cells in cell culture.

"Proliferating cells" are those which are actively undergoing cell division and growing exponentially. "Loss of cell proliferation control" refers to the property of cells that have lost the cell cycle controls that normally ensure appropriate restriction of cell division. Cells that have lost such controls proliferate at a faster than normal rate, without stimulatory signals, and do not respond to inhibitory signals.

"Advanced cancer" means cancer that is no longer localized to the primary tumor site, or a cancer that is Stage III or IV according to the American Joint Committee on Cancer (AJCC).

"Well tolerated" refers to the absence of adverse changes in health status that occur as a result of the treatment and would affect treatment decisions.

"Metastatic" refers to tumor cells, e.g., human breast cancer cells, that are able to establish secondary tumor lesions in the lungs, liver, bone or brain of immune deficient mice upon injection into the mammary fat pad and/or the circulation of the immune deficient mouse.

"Non-metastatic" refers to tumor cells, e.g., human breast cancer cells, that are unable to establish secondary tumor lesions in the lungs, liver, bone or brain or other target organs of breast cancer metastasis in immune deficient mice upon injection into the mammary fat pad and/or the circulation. The human tumor cells used herein and addressed herein as non-metastatic are able to establish primary tumors upon injection into the mammary fat pad of the immune deficient mouse, but they are unable to disseminate from those primary tumors.

"Lymphocyte" as used herein has the normal meaning in the art, and refers to any of the mononuclear, nonphagocytic leukocytes, found in the blood, lymph, and lymphoid tissues, e.g., B and T lymphocytes.

"Epitope" refers to a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

An intact "antibody" comprises at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. The term antibody includes antigen-binding portions of an intact antibody that retain capacity to bind activated integrin receptor. Examples of binding include (i) a Fab fragment, a monovalent fragment consisting of the $V_L$, $V_H$, $C_L$ and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the V$_L$ and V$_H$ domains of a single arm of an antibody, (v) a dAb fragment (Ward et al., *Nature* 341: 544-546, 1989), which consists of a VH domain; and (vi) an isolated complementarity determining region (CDR).

"Single chain antibodies" or "single chain Fv (scFv)" refers to an antibody fusion molecule of the two domains of the Fv fragment, V$_L$ and V$_H$. Although the two domains of the Fv fragment, V$_L$ and V$_H$, are coded for by separate genes, they can be joined, using recombinant methods, by a synthetic linker that enables them to be made as a single protein chain in which the V$_L$ and V$_H$ regions pair to form monovalent molecules (known as single chain Fv (scFv); see, e.g., Bird et al., *Science* 242: 423-426, 1988; and Huston et al., *Proc. Natl. Acad. Sci. USA*, 85: 5879-5883, 1988). Such single chain antibodies are included by reference to the term "antibody" fragments can be prepared by recombinant techniques or enzymatic or chemical cleavage of intact antibodies.

"Human sequence antibody" includes antibodies having variable and constant regions (if present) derived from human germline immunoglobulin sequences. The human sequence antibodies of the invention can include amino acid residues not encoded by human germline immunoglobulin sequences (e.g., mutations introduced by random or site-specific mutagenesis in vitro or by somatic mutation in vivo). Such antibodies can be generated in non-human transgenic animals, e.g., as described in PCT Publication Nos. WO 01/14424 and WO 00/37504. However, the term "human sequence antibody", as used herein, is not intended to include antibodies in which CDR sequences derived from the germline of another mammalian species, such as a mouse, have been grafted onto human framework sequences (e.g., humanized antibodies).

Also, recombinant immunoglobulins may be produced. See, Cabilly, U.S. Pat. No. 4,816,567, incorporated herein by reference in its entirety and for all purposes; and Queen et al., *Proc. Nat'l Acad. Sci. USA* 86: 10029-10033, 1989.

"Monoclonal antibody" refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

"Polyclonal antibody" refers to a preparation of more than 1 (two or more) different antibodies to a cell surface receptor, e.g., human activated integrin receptor. Such a preparation includes antibodies binding to a range of different epitopes. Antibodies to activated integrin receptor can bind to an epitope on human activated integrin receptor so as to inhibit activated integrin receptor from interacting with a counterreceptor or co-receptor. These and other antibodies suitable for use in the present invention can be prepared according to methods that are well known in the art and/or are described in the references cited here. In preferred embodiments, anti-activated integrin receptor antibodies used in the invention are "human antibodies"—e.g.,. antibodies isolated from a human—or they are "human sequence antibodies" (defined supra).

"Immune cell response" refers to the response of immune system cells to external or internal stimuli (e.g., antigen, cell surface receptors, activated integrin receptors, cytokines, chemokines, and other cells) producing biochemical changes in the immune cells that result in immune cell migration, killing of target cells, phagocytosis, production of antibodies, other soluble effectors of the immune response, and the like.

"Immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, metastatic breast cancer cells, invading pathogens, cells or tissues infected with pathogens, or, in cases of autoimmunity or pathological inflammation, normal human cells or tissues.

"T lymphocyte response" and "T lymphocyte activity" are used here interchangeably to refer to the component of immune response dependent on T lymphocytes (e.g., the proliferation and/or differentiation of T lymphocytes into helper, cytotoxic killer, or suppressor T lymphocytes, the provision of signals by helper T lymphocytes to B lymphocytes that cause or prevent antibody production, the killing of specific target cells by cytotoxic T lymphocytes, and the release of soluble factors such as cytokines that modulate the function of other immune cells).

Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen et al., *Immunity*, 2: 373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.*, 86: 4230-4, 1989); (4) mast cells can be incubated with reagents that cross-link their Fc-epsilon receptors and histamine release measured by enzyme immunoassay (Siraganian et al., *TIPS*, 4: 432-437, 1983).

Similarly, products of an immune response in either a model organism (e.g., mouse) or a human patient can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood*, 72: 1310-5, 1988); (3) the proliferation of peripheral blood mononuclear cells in response to mitogens or mixed lymphocyte reaction can be measured using $^3$H-thymidine; (4) the phagocitic capacity of granulocytes, macrophages, and other phagocytes in PBMCs can be measured by placing PMBCs in wells together with labeled particles (Peters et al., *Blood*, 72: 1310-5, 1988); and (5) the differentiation of immune system cells can be measured by labeling PBMCs with antibodies to CD molecules such as CD4 and CD8 and measuring the fraction of the PBMCs expressing these markers.

For convenience, immune responses are often described in the present invention as being either "primary" or "secondary" immune responses. A primary immune response, which is also described as a "protective" immune response, refers to an immune response produced in an individual as a result of some initial exposure (e.g. the initial "immunization") to a particular antigen, e.g., cell surface receptor, or activated integrin receptor. Such an immunization can occur, for example, as the result of some natural exposure to the antigen (for example, from initial infection by some pathogen that exhibits or presents the antigen) or from antigen presented by cancer cells of some tumor in the individual (for example, a metastatic breast cancer cell). Alternatively, the immunization can occur as a result of vaccinating the individual with a vaccine containing the antigen. For example, the vaccine can be a cancer vaccine comprising one or more antigens from a cancer cell e.g., a metastatic breast cancer cell.

A primary immune response can become weakened or attenuated over time and can even disappear or at least become so attenuated that it cannot be detected. Accordingly, the present invention also relates to a "secondary" immune response, which is also described here as a "memory immune response." The term secondary immune response refers to an immune response elicited in an individual after a primary immune response has already been produced. Thus, a secondary or immune response can be elicited, e.g., to enhance an existing immune response that has become weakened or attenuated, or to recreate a previous immune response that has either disappeared or can no longer be detected. An agent that can be administrated to elicit a secondary immune response is after referred to as a "booster" since the agent can be said to "boost" the primary immune response.

As an example, and not by way of limitation, a secondary immune response can be elicited by re-introducing to the individual an antigen that elicited the primary immune response (for example, by re-administrating a vaccine). However, a secondary immune response to an antigen can also be elicited by administrating other agents that can not contain the actual antigen. For example, the present invention provides methods for potentiating a secondary immune response by administrating an antibody to activated integrin receptor to an individual. In such methods the actual antigen need not necessarily be administered with the antibody to activated integrin receptor and the composition containing the antibody need not necessarily contain the antigen. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by $CD^{4+}$ cells. A first exposure to an antigen primes the immune system and additional exposure(s) results in a DTH.

"Immunologically cross-reactive" or "immunologically reactive" refers to an antigen which is specifically reactive with an antibody which was generated using the same ("immunologically reactive") or different ("immunologically cross-reactive") antigen. Generally, the antigen is activated integrin receptor, or more typically an αvβ3 integrin receptor or subsequence thereof.

"Immunologically reactive conditions" refers to conditions which allow an antibody, generated to a particular epitope of an antigen, to bind to that epitope to a detectably greater degree than the antibody binds to substantially all other epitopes, generally at least two times above background binding, preferably at least five times above background binding. Immunologically reactive conditions are dependent upon the format of the antibody binding reaction and typically are those utilized in immunoassay protocols. See, Harlow and Lane, *Antibodies, A Laboratory Manual,* Cold Spring Harbor Publications, New York, 1988 for a description of immunoassay formats and conditions.

"Cell surface receptor" refers to molecules and complexes of molecules capable of receiving a signal and the transmission of such a signal across the plasma membrane of a cell. An example of a "cell surface receptor" of the present invention is an activated integrin receptor, for example, an activated αvβ3 integrin receptor on a metastatic cell.

"Nonspecific T cell activation" refers to the stimulation of T cells independent of their antigenic specificity.

"Effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fe receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens. An effector cell can also phagocytose a target antigen, target cell, metastatic cancer cell, or microorganism.

"Target cell" refers to any undesirable cell in a subject (e.g., a human or animal) that can be targeted by the Ab or Ab composition of the invention. The target cell can be a cell expressing or overexpressing human activated integrin receptor. Cells expressing human activated integrin receptor can include tumor cells, e.g. breast cancer cells or metastatic breast cancer cells.

Targets of interest for antibody compositions metastatic cancer cells, e.g., metastatic breast cancer cells, include, but are not limited to, cell surface receptors, growth factor receptors, antibodies, including anti-idiotypic antibodies and autoantibodies present in cancer, such as metastatic cancer and metastatic breast cancer. Other targets are adhesion proteins such as integrins, selecting, and immunoglobulin superfamily members. Springer, *Nature,* 346: 425-433, 1990; Osborn, *Cell,* 62: 3, 1990; Hynes, *Cell,* 69: 11, 1992. Other targets of interest are growth factor receptors (e.g., FGFR, PDGFR, EGF, her/neu, NGFR, and VEGF) and their ligands. Other targets are G-protein receptors and include substance K receptor, the angiotensin receptor, the α- and β-adrenergic receptors, the serotonin receptors, and PAF receptor. See, e.g., Gilman, *Ann. Rev. Biochem.* 56: 625-649, 1987. Other targets include ion channels (e.g., calcium, sodium, potassium channels, channel proteins that mediate multidrug resistance), muscarinic receptors, acetylcholine receptors, GABA receptors, glutamate receptors, and dopamine receptors (see Harpold, U.S. Pat. No. 5,401,629 and U.S. Pat. No. 5,436,128). Other targets are cytokines, such as interleukins IL-1 through IL-13, tumor necrosis factors α- and β, interferons α-, β- and γ, tumor growth factor Beta (TGF-β), colony stimulating factor (CSF) and granulocyte monocyte colony stimulating factor (GM-CSF). See Aggrawal et al., eds., *Human Cytokines: Handbook for Basic & Clinical Research,* Blackwell Scientific, Boston, Mass., 1991. Other targets are hormones, enzymes, and intracellular and intercellular messengers, such as adenyl cyclase, guanyl cyclase, and phospholipase C. Drugs are also targets of interest. Target molecules can be human, mammalian or bacterial. Other targets are antigens, such as proteins, glycoproteins and carbohydrates from microbial pathogens, both viral and bacterial, and tumors. Still other targets are described in U.S. Pat. No. 4,366,241, incorporated herein by reference in its entirety and for all purposes. Some agents screened by the target merely bind to a target. Other agents agonize or antagonize the target.

Cancer Treatment

Blockade of activated integrin receptor by antibody compositions can enhance the memory or secondary immune response to cancerous cells in the patient. Antibodies to activated integrin receptor can be combined with an immunogenic agent, such as cancerous cells, purified tumor antigens (including recombinant proteins, peptides, and carbohydrate molecules), cells, and cells transfected with genes encoding immune stimulating cytokines and cell surface antigens, or used alone, to stimulate immunity.

Antibodies to activated integrin receptor is effective when following a vaccination protocol. Many experimental strategies for vaccination against tumors have been devised (see Rosenberg, *ASCO Educational Book* Spring: 60-62, 2000; Logothetis, *ASCO Educational Book* Spring: 300-302, 2000; Khayat, *ASCO Educational Book Spring:* 414-428, 2000; Foon, *ASCO Educational Book* Spring: 730-738, 2000; see also Restifo et al., *Cancer: Principles and Practice of Oncology*, 61: 3023-3043, 1997. In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination. Dranoff et al., *Proc. Natl. Acad. Sci U.S.A.*, 90: 3539-43, 1993.

Antibodies to activated integrin receptor can boost GMCSF-modified tumor cell vaccines improves efficacy of vaccines in a number of experimental tumor models such as mammary carcinoma (Hurwitz et al., 1998, supra), primary prostate cancer (Hurwitz et al., *Cancer Research*, 60: 2444-8, 2000) and melanoma (van Elsas et al., *J. Exp. Med.*, 190: 355-66, 1999). In these instances, non-immunogenic tumors, such as the B 16 melanoma, have been rendered susceptible to destruction by the immune system. The tumor cell vaccine can also be modified to express other immune activators such as IL2, and costimulatory molecules, among others.

The study of gene expression and large scale gene expression patterns in various tumors has led to the definition of so called "tumor specific antigens" (Rosenberg, Immunity, 10: 281-7, 1999). In many cases, these tumor specific antigens are differentiation antigens expressed in the tumors and in the cell from which the tumor arose, for example melanocyte antigens gp100, MAGE antigens, Trp-2. More importantly, many of these antigens can be shown to be the targets of tumor specific T cells found in the host. Antibodies to activated integrin receptor can be used as a boosting agent in conjunction with vaccines based on recombinant versions of proteins and/or peptides found to be expressed in a tumor in order to potentiate a secondary or memory immune response to these proteins. These proteins are normally viewed by the immune system as self antigens and are therefore tolerant to them. The tumor antigen can also include the protein telomerase, which is required for the synthesis of telomeres of chromosomes and which is expressed in more than 85% of human cancers and in only a limited number of somatic tissues (Kim et al., *Science*, 266: 2011-2013, 1994). These somatic tissues can be protected from immune attack by various means. Tumor antigen can also be "neo-antigens" expressed in cancer cells because of somatic mutations that alter protein sequence or create fusion proteins between two unrelated sequences (e.g. bcr-abl in the Philadelphia chromosome), or idiotype from B cell tumors. Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which can be used in conjunction with antibodies to activated integrin receptor is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot et al., *Science*, 269: 1585-1588, 1995; Tamura et al., *Science*, 278: 117-120, 1997.

Dendritic cells (DC) are potent antigen presenting cells that can be used to prime antigen-specific responses to activated integrin receptors on metastatic tumor cells. DC's can be produced ex vivo and loaded with various protein and peptide antigens as well as tumor cell extracts (Nestle et al., *Nature Medicine*, 4: 328-332, 1998). DCs can also be transduced by genetic means to express these tumor antigens as well. DCs have also been fused directly to tumor cells for the purposes of immunization (Kugler et al., *Nature Medicine*, 6: 332-336, 2000). As a method of vaccination, DC immunization can be effectively boosted with antibodies to activated integrin receptor to activate more potent anti-tumor responses.

Another type of melanoma vaccine that can be combined with antibodies to activated integrin receptor is a vaccine prepared from a melanoma cell line lysate, in conjunction with an immunological adjuvant, such as the MELACINE™ vaccine, a mixture of lysates from two human melanoma cell lines plus DETOX™ immunological adjuvant. Vaccine treatment can be boosted with anti-activated integrin receptor, with or without additional chemotherapeutic treatment.

Antibodies to activated integrin receptor can also be used to boost immunity induced through standard cancer treatments. In these instances, it can be possible to reduce the dose of chemotherapeutic reagent administered (Mokyr et al., *Cancer Research*, 58: 5301-5304, 1998). The scientific rationale behind the combined use of antibodies to activated integrin receptor and chemotherapy is that cell death, that is a consequence of the cytotoxic action of most chemotherapeutic compounds, should result in increased levels of tumor antigen in the antigen presentation pathway. Thus, antibodies to activated integrin receptor can boost an immune response primed to chemotherapy release of tumor cells. Examples of chemotherapeutic agents combined with treatment with antibodies to activated integrin receptor can include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochlorperazine, rituximab, saproin, tamoxifen, taxol, topotecan hydrochloride, trastuzumab, vinblastine, vincristine and vinorelbine tartrate. For prostate cancer treatment, a preferred chemotherapeutic agent with which anti-activated integrin receptor can be combined is paclitaxel (Taxol™). For melanoma cancer treatment, a preferred chemotherapeutic agent with which anti-activated integrin receptor can be combined is dacarbazine (DTIC).

Other combination therapies that can result in immune system priming through cell death are radiation, surgery, and hormone deprivation (Kwon et al., *Proc. Natl. Acad. Sci U.S.A.*, 96: 15074-9, 1999. Each of these protocols creates a source of tumor antigen in the host. For example, any manipulation of the tumor at the time of surgery can greatly increase the number of cancer cells in the blood (Schwartz et al., *Principles of Surgery.* 4$^{th}$ ed., p. 338, 1984). Angiogenesis inhibitors can also be combined with antibodies to activated integrin receptor. Inhibition of angiogenesis leads to tumor cell death which can feed tumor antigen into host antigen presentation pathways. All of these cause tumor release and possible immune system priming that antibodies to activated integrin receptor can boost.

Antibody Therapeutics

As is well understood in the art, biospecific capture reagents include antibodies, binding fragments of antibodies which bind to activated integrin receptors on metastatic cells (e.g., single chain antibodies, Fab' fragments, F(ab)'2 fragments, and scFv proteins and affibodies (Affibody, Teknikringen 30, floor 6, Box 700 04, Stockholm SE-10044, Sweden; See U.S. Pat. No. 5,831,012, incorporated herein by reference in its entirety and for all purposes)). Depending on intended use, they also may include receptors and other proteins that specifically bind another biomolecule.

The hybrid antibodies and hybrid antibody fragments include complete antibody molecules having full length heavy and light chains, or any fragment thereof, such as Fab, Fab', F(ab')$_2$, Fd, scFv, antibody light chains and antibody heavy chains. Chimeric antibodies which have variable regions as described herein and constant regions from various species are also suitable. See, for example, U.S. application No. 20030022244.

Initially, a predetermined target object is chosen to which an antibody may be raised. Techniques for generating monoclonal antibodies directed to target objects are well known to those skilled in the art. Examples of such techniques include, but are not limited to, those involving display libraries, xeno or humab mice, hybridomas, and the like Target objects include any substance which is capable of exhibiting antigenicity and are usually proteins or protein polysaccharides. Examples include receptors, enzymes, hormones, growth factors, peptides and the like. It should be understood that not only are naturally occurring antibodies suitable for use in accordance with the present disclosure, but engineered antibodies and antibody fragments which are directed to a predetermined object are also suitable.

Antibodies (Abs) that can be subjected to the techniques set forth herein include monoclonal and polyclonal Abs, and antibody fragments such as Fab, Fab', F(ab')$_2$, Fd, scFv, diabodies, antibody light chains, antibody heavy chains and/or antibody fragments derived from phage or phagemid display technologies. To begin with, an initial antibody is obtained from an originating species. More particularly, the nucleic acid or amino acid sequence of the variable portion of the light chain, heavy chain or both, of an originating species antibody having specificity for a target antigen is needed. The originating species is any species which was used to generate the antibodies or antibody libraries, e.g., rat, mice, rabbit, chicken, monkey, human, and the like Techniques for generating and cloning monoclonal antibodies are well known to those skilled in the art. After a desired antibody is obtained, the variable regions ($V_H$ and $V_L$) are separated into component parts (i.e, frameworks (FRs) and CDRs) using any possible definition of CDRs (e.g., Kabat alone, Chothia alone, Kabat and Chothia combined, and any others known to those skilled in the art). Once that has been obtained, the selection of appropriate target species frameworks is necessary. One embodiment involves alignment of each individual framework region from the originating species antibody sequence with variable amino acid sequences or gene sequences from the target species. Programs for searching for alignments are well known in the art, e.g., BLAST and the like. For example, if the target species is human, a source of such amino acid sequences or gene sequences (germline or rearranged antibody sequences) may be found in any suitable reference database such as Genbank, the NCBI protein databank (www.ncbi.nlm.nih.gov/BLAST/), VBASE, a database of human antibody genes (www.mrc-cpe.cam.ac.uk/imt-doc), and the Kabat database of immunoglobulins (www.immuno.bme.nwu.edu) or translated products thereof. If the alignments are done based on the nucleotide sequences, then the selected genes should be analyzed to determine which genes of that subset have the closest amino acid homology to the originating species antibody. It is contemplated that amino acid sequences or gene sequences which approach a higher degree homology as compared to other sequences in the database can be utilized and manipulated in accordance with the procedures described herein. Moreover, amino acid sequences or genes which have lesser homology can be utilized when they encode products which, when manipulated and selected in accordance with the procedures described herein, exhibit specificity for the predetermined target antigen. In certain embodiments, an acceptable range of homology is greater than about 50%. It should be understood that target species may be other than human.

The term "treating" refers to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with ocular disease. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

"Treating" or "treatment" of cancer or metastatic cancer using the methods of the present invention includes preventing the onset of symptoms in a subject that may be at increased risk of ocular infection but does not yet experience or exhibit symptoms of infection, inhibiting the symptoms of infection (slowing or arresting its development), providing relief from the symptoms or side-effects of infection (including palliative treatment), and relieving the symptoms of infection (causing regression).

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

The terms "identical" or percent "identity," in the context of two or more nucleic acids or polypeptide sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence encoding a collectin described herein or amino acid sequence of a collectin described herein), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." This term also refers to, or can be applied to, the compliment of a test sequence. The term also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman, *Adv. Appl. Math*, 2: 482, 1981, by the homology alignment algorithm of Needleman and Wunsch, *J. Mol. Biol*, 48:443, 1970, by the search for similarity method of Pearson and Lipman, *Proc. Nat'l. Acad. Sci. USA*, 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., eds., *Current Protocols in Molecular Biology*. 1995 supplement).

A preferred example of algorithm that is suitable for determining percent sequence identity and sequence similarity are the BLAST and BLAST 2.0 algorithms, which are described in Altschul et al., *Nuc. Acids Res,* 25:3389-3402, 1977 and Altschul et al., *J. Mol. Biol,* 215:403-410, 1990, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, $M=5$, $N=-4$ and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci.* USA, 89:10915, 1989) alignments (B) of 50, expectation (E) of 10, $M=5$, $N=-4$, and a comparison of both strands.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., *Molecular Biology of the Cell*, 3rd ed., 1994) and Cantor and Schimmel, *Biophysical Chemistry Part I: The Conformation of Biological Macromolecules*, 1980. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity, e.g., a kinase domain. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript can be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, "Techniques in Biochemistry and Molecular Biology—Hybridization with Nucleic Probes," *Overview of principles of hybridization and the strategy of nucleic acid assays*, 1993. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., Ausubel et al, supra.

For PCR, a temperature of about 36° C. is typical for low stringency amplification, although annealing temperatures can vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec. –2 min., and an extension phase of about 72° C. for 1-2 min. Protocols and guidelines for low and high stringency amplification reactions are provided, e.g., in Innis et al., *PCR Protocols, A Guide to Methods and Applications,* Academic Press, Inc. N.Y., 1990.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g. $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compositions of the invention can be administered. In some embodiments of the present invention, the patient will be suffering from a condition that causes lowered resistance to disease, e.g., HIV. In an exemplary embodiment of the present invention, to identify subject patients for treatment with a pharmaceutical composition comprising one or more collectins and/or surfactant proteins according to the methods of the invention, accepted screening methods are employed to determine the status of an existing disease or condition in a subject or risk factors associated with a targeted or suspected disease or condition. These screening methods include, for example, ocular examinations to determine whether a subject is suffering from an ocular disease. These and other routine methods allow the clinician to select subjects in need of therapy. In certain embodiments of the present invention, ophthalmic compositions for storing, cleaning, re-wetting and/or disinfecting a contact lens, as well as artificial tear compositions and/or contact lenses will contain one or more collectins and/or surfactant proteins thereby inhibiting the development of ocular disease in contact-lens wearers.

"Concomitant administration" of a known cancer therapeutic drug with a pharmaceutical composition of the present invention means administration of the drug and the collectin and/or surfactant protein composition at such time that both the known drug and the composition of the present invention will have a therapeutic effect. Such concomitant administration may involve concurrent (i.e. at the same time), prior, or subsequent administration of the antimicrobial drug with respect to the administration of a compound of the present invention. A person of ordinary skill in the art, would have no difficulty determining the appropriate timing, sequence and dosages of administration for particular drugs and compositions of the present invention.

After selecting suitable frame work region candidates from the same family and/or the same family member, either or both the heavy and light chain variable regions are produced by grafting the CDRs from the originating species into the hybrid framework regions. Assembly of hybrid antibodies or hybrid antibody fragments having hybrid variable chain regions with regard to either of the above aspects can be accomplished using conventional methods known to those skilled in the art. For example, DNA sequences encoding the hybrid variable domains described herein (i.e., frameworks based on the target species and CDRs from the originating species) may be produced by oligonucleotide synthesis and/or PCR. The nucleic acid encoding CDR regions may also be isolated from the originating species antibodies using suitable restriction enzymes and ligated into the target species framework by ligating with suitable ligation enzymes. Alternatively, the framework regions of the variable chains of the originating species antibody may be changed by site-directed mutagenesis.

Since the hybrids are constructed from choices among multiple candidates corresponding to each framework region, there exist many combinations of sequences which are amenable to construction in accordance with the principles described herein. Accordingly, libraries of hybrids can be assembled having members with different combinations of individual framework regions. Such libraries can be electronic database collections of sequences or physical collections of hybrids.

Assembly of a physical antibody or antibody fragment library is preferably accomplished using synthetic oligonucleotides. In one example, oligonucleotides are designed to have overlapping regions so that they could anneal and be filled in by a polymerase, such as with polymerase chain reaction (PCR). Multiple steps of overlap extension are performed in order to generate the $V_L$ and $V_H$ gene inserts. Those fragments are designed with regions of overlap with human constant domains so that they could be fused by overlap extension to produce full length light chains and Fd heavy chain fragments. The light and heavy Fd chain regions may be linked together by overlap extension to create a single Fab library insert to be cloned into a display vector. Alternative methods for the assembly of the humanized library genes can also be used. For example, the library may be assembled from overlapping oligonucleotides using a Ligase Chain Reaction (LCR) approach. Chalmers et al., *Biotechniques*, 30-2: 249-252, 2001.

Various forms of antibody fragments may be generated and cloned into an appropriate vector to create a hybrid antibody library or hybrid antibody fragment library. For example variable genes can be cloned into a vector that contains, in-frame, the remaining portion of the necessary constant domain. Examples of additional fragments that can be cloned include whole light chains, the Fd portion of heavy chains, or fragments that contain both light chain and heavy chain Fd coding sequence. Alternatively, the antibody fragments used for humanization may be single chain antibodies (scFv).

Any selection display system may be used in conjunction with a library according to the present disclosure. Selection protocols for isolating desired members of large libraries are known in the art, as typified by phage display techniques. Such systems, in which diverse peptide sequences are displayed on the surface of filamentous bacteriophage have proven useful for creating libraries of antibody fragments (and the nucleotide sequences that encode them) for the in vitro selection and amplification of specific antibody fragments that bind a target antigen. Scott et al., *Science*, 249: 386, 1990. The nucleotide sequences encoding the VH and VL regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pIII or pVIII). Alternatively, antibody fragments are displayed externally on lambda phage or T7 capsids (phagebodies). An advantage of phage-based display systems is that, because they are biological systems, selected library members can be amplified simply by growing the phage containing the selected library member in bacterial cells. Furthermore, since the nucleotide sequence that encode the polypeptide library member is contained on a phage or phagemid vector, sequencing, expression and subsequent genetic manipulation is relatively straightforward. Methods for the construction of bacteriophage antibody display libraries and lambda phage expression libraries are well known in the art. McCafferty et al., *Nature*, 348: 552, 1990; Kang et al., *Proc. Natl. Acad. Sci. U.S.A.*, 88: 4363, 1991.

The present invention further relates to antibodies and T-cell antigen receptors (TCR) which specifically bind the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH$_1$, CH$_2$, and CH$_3$ domains. Also included in the invention are any combinations of variable region(s) and hinge region, CH$_1$, CH$_2$, and CH$_3$ domains. The present invention further includes monoclonal, polyclonal, chimeric, humanized, and human monoclonal and human polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt et al., *J. Immunol.* 147: 60-69, 1991; U.S. Pat. Nos. 5,573,920; 4,474,893; 5,601,819; 4,714,681; 4,925,648, each incorporated herein by reference in their entirety and for all purposes; Kostelny et al., *J. Immunol.* 148: 1547-1553, 1992.

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or $K_d$ less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Antibodies to activated integrin receptors vention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow and Lane, supra, incorporated herein by reference in its entirety and for all purposes.

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387, each incorporated herein by reference in their entirety and for all purposes.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not a limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art and taught in Harlow and Lane, supra; Hammerling et al., *Monoclonal Antibodies and T-Cell Hybridomas*, 563-681, 1981, said references incorporated by reference in their entireties. Fab and F(ab')$_2$ fragments may be produced by proteolytic cleavage, using enzymes such as papain (to produce Fab fragments) or pepsin (to produce F(ab')$_2$ fragments).

Alternatively, antibodies to activated integrin receptor can be produced through the application of recombinant DNA and phage display technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182: 41-50, 1995; Ames et al., *J. Immunol. Methods* 184: 177-186, 1995; Kettleborough et al., *Eur. J. Immunol.* 24: 952-958, 1994; Persic et al., *Gene* 187: 9-18, 1997; Burton et al., *Advances in Immunology* 57: 191-280, 1994; PCT/GB91/01134; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727 and 5,733,743, each incorporated herein by reference in their entirety and for all purposes.

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax et al., *BioTechniques* 12: 864-869, 1992; and Sawai et al., *AJRI* 34: 26-34, 1995; and Better et al., *Science* 240: 1041-1043, 1988.

Examples of techniques which can be used to produce single-chain Fvs and antibodies include those described in U.S. Pat. Nos. 4,946,778 and 5,258,498, each incorporated herein by reference in their entirety and for all purposes; Huston et al., *Methods in Enzymology*, 203: 46-88, 1991; Shu, L. et al., *PNAS* 90: 7995-7999, 1993; and Skerra et al., *Science* 240: 1038-1040, 1988. For some uses, including in vivo use of antibodies in humans and in vitro detection assays, it may be preferable to use chimeric, humanized, or human antibodies. Methods for producing chimeric antibodies are known in the art. See e.g., Morrison, *Science* 229: 1202, 1985; Oi et al., *BioTechniques* 4: 214, 1986; Gillies et al., *J. Immunol. Methods*, 125: 191-202, 1989; and U.S. Pat. No. 5,807,715. Antibodies can be humanized using a variety of techniques including CDR-grafting (EP 0 239 400; WO 91/09967; and U.S. Pat. Nos. 5,530,101 and 5,585,089), veneering or resurfacing (EP 0 592 106; EP 0 519 596; Padlan E. A., Molecular *Immunology*, 28: 489-498, 1991; Studnicka et al., *Protein Engineering* 7: 805-814, 1994; Roguska et al., *PNAS* 91: 969-973, 1994), and chain shuffling (U.S. Pat. No. 5,565,332). Human antibodies can be made by a variety of methods known in the art including phage display methods described above. See also, U.S. Pat. Nos. 4,444,887; 4,716,111; 5,545,806; and 5,814,318; and WO 98/46645; WO 98/50433; WO 98/24893; WO 98/16654; WO 96/34096; WO 96/33735; and WO 91/10741, each incorporated herein by reference in their entirety and for all purposes.

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and WO 93/21232; EP 0 439 095; Naramura et al., Immunol. Lett. 39: 91-99, 1994; U.S. Pat. No. 5,474,981, incorporated herein by reference in its entirety and for all purposes; Gillies et al., PNAS 89: 1428-1432, 1992; Fell et al., J. Immunol. 146: 2446-2452, 1991.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, $CH_1$ domain, $CH_2$ domain, and $CH_3$ domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 0 307 434, EP 0 367 166; WO 96/04388; and WO 91/06570, each incorporated herein by reference in their entirety and for all purposes; Ashkenazi et al., PNAS, 88: 10535-10539, 1991; Zheng et al., J. Immunol., 154: 5590-5600, 1995; and Vil et al., PNAS, 89: 11337-11341, 1992.

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097, each incorporated herein by reference in their entirety and for all purposes; Deng et al., Blood 92: 1981-1988, 1998; Chen, et al., Cancer Res., 58: 3668-3678, 1998; Harrop et al., J. Immunol. 161: 1786-1794, 1998; Zhu et al., Cancer Res., 58: 3209-3214, 1998; Yoon, et al., J. Immunol., 160: 3170-3179, 1998; Prat et al., J. Cell. Sci., 111: 237-247, 1998; Pitard et al., J. Immunol. Methods, 205: 177-190, 1997; Liautard et al., Cytokinde, 9: 233-241, 1997; Carlson et al., J. Biol. Chem., 272: 11295-11301, 1997; Taryman et al., Neuron, 14: 755-762, 1995; Muller et al., Structure, 6: 1153-1167, 1998; Bartunek et al., Cytokinem, 8: 14-20, 1996. As discussed above, antibodies to activated integrin receptors on metatstatic cells can, in turn, be utilized to generate anti-idiotype antibodies that "mimic" polypeptides of the invention using techniques well known to those skilled in the art. (See, e.g., Greenspan et al., FASEB J. 7: 437-444, 1989 and Nissinoff, J. Immunol. 147: 2429-2438, 1991). For example, antibodies which bind to and competitively inhibit polypeptide multimerization and/or binding of a polypeptide of the invention to ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

"Inhibitors," "activators," and "modulators" of activated integrin receptor on metastatic cells are used to refer to inhibitory, activating, or modulating molecules, respectively, identified using in vitro and in vivo assays for integrin receptor binding or signaling, e.g., ligands, agonists, antagonists, and their homologs and mimetics.

The term "modulator" includes inhibitors and activators. Inhibitors are agents that, e.g., bind to, partially or totally block stimulation, decrease, prevent, delay activation, inactivate, desensitize, or down regulate the activity of activated integrin receptors, e.g., antagonists. Activators are agents that, e.g., bind to, stimulate, increase, open, activate, facilitate, enhance activation, sensitize or up regulate the activity of activated integrin receptors, e.g., agonists. Modulators include agents that, e.g., alter the interaction of activated integrin receptor with: proteins that bind activators or inhibitors, receptors, including proteins, peptides, lipids, carbohydrates, polysaccharides, or combinations of the above, e.g., lipoproteins, glycoproteins, and the like. Modulators include genetically modified versions of naturally-occurring activated integrin receptor ligands, e.g., with altered activity, as well as naturally occurring and synthetic ligands, antagonists, agonists, small chemical molecules and the like. Such assays for inhibitors and activators include, e.g., applying putative modulator compounds to a cell expressing an activated integrin receptor and then determining the functional effects on integrin receptor signaling, as described herein. Samples or assays comprising activated integrin receptor that are treated with a potential activator, inhibitor, or modulator are compared to control samples without the inhibitor, activator, or modulator to examine the extent of inhibition. Control samples (untreated with inhibitors) can be assigned a relative integrin receptor activity value of 100%. Inhibition of activated integrin receptor is achieved when the integrin receptor activity value relative to the control is about 80%, optionally 50% or 25-0%. Activation of integrin receptor is achieved when the integrin receptor activity value relative to the control is 110%, optionally 150%, optionally 200-500%, or 1000-3000% higher.

The ability of a molecule to bind to activated integrin receptor can be determined, for example, by the ability of the putative ligand to bind to activated integrin receptor immunoadhesin coated on an assay plate. Specificity of binding can be determined by comparing binding to non-activated integrin receptor.

In one embodiment, antibody binding to activated integrin receptor can be assayed by either immobilizing the ligand or the receptor. For example, the assay can include immobilizing activated integrin receptor fused to a His tag onto Ni-activated NTA resin beads. Antibody can be added in an appropriate buffer and the beads incubated for a period of time at a given temperature. After washes to remove unbound material, the bound protein can be released with, for example, SDS, buffers with a high pH, and the like and analyzed.

Fusion Proteins

Antibodies to activated integrin receptor can be used to generate fusion proteins. For example, the antibodies of the present invention, when fused to a second protein, can be used as an antigenic tag. Antibodies raised against activated integrin receptor can be used to indirectly detect the second protein by binding to the polypeptide. Moreover, because secreted proteins target cellular locations based on trafficking signals, the integrin receptor can be used as a targeting molecule once fused to other proteins.

Examples of domains that can be fused to polypeptides include not only heterologous signal sequences, but also other heterologous functional regions. The fusion does not necessarily need to be direct, but may occur through linker sequences.

Moreover, fusion proteins may also be engineered to improve characteristics of the polypeptide. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, antibody compositions or cell surface receptors, or integrin receptors, including fragments, and specifically epitopes, can be combined with parts of the constant domain of immunoglobulins (IgG), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. EP A 394,827; Traunecker et al., *Nature,* 331: 84-86, 1988. Fusion proteins having disulfide-linked dimeric structures (due to the IgG) can also be more efficient in binding and neutralizing other molecules, than the monomeric secreted protein or protein fragment alone. Fountoulakis et al., *J. Biochem.* 270: 3958-3964,1995.

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. Bennett et al., *J. Molecular Recognition* 8: 52-58, 1995; K. Johanson et al., *J. Biol. Chem.,* 270: 9459-9471 1995.

Moreover, the polypeptides can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., *Cell* 37: 767, 1984.

Thus, any of these above fusions can be engineered using the polynucleotides or the polypeptides of the present invention.

Expression of Recombinant Antibodies

Chimeric, humanized and human antibodies to cell surface receptor, e.g., activated integrin receptor on metastatic cells, are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies. See U.S. Application No. 20020199213 incorporated herein by reference in its entirety and for all purposes.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, *From Genes To Clones*, VCH Publishers, NY, 1987. A number of suitable host cell lines capable of secreting intact heterologous proteins have been developed in the art, and include Chinese hamster ovary (CHO) cell lines, various COS cell lines, HeLa cells, L cells and myeloma cell lines. Preferably, the cells are nonhuman. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Queen et al., *Immunol. Rev.* 89: 49, 1986. Preferred expression control sequences are promoters derived from endogenous genes, cytomegalovirus, SV40, adenovirus, bovine papillomavirus, and the like. Co, et al., *J Immunol.* 148: 1149, 1992.

Alternatively, antibody coding sequences can be incorporated in transgenes for introduction into the genome of a transgenic animal and subsequent expression in the milk of the transgenic animal. See, e.g., U.S. Pat. Nos. 5,741,957; 5,304,489; and 5,849,992, each incorporated herein by reference in their entirety and for all purposes. Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., *Molecular Cloning*). For production of transgenic animals, transgenes can be microinjected into fertilized oocytes, or can be incorporated into the genome of embryonic stem cells, and the nuclei of such cells transferred into enucleated oocytes.

Once expressed, collections of antibodies are purified from culture media and host cells. Antibodies can be purified according to standard procedures of the art, including HPLC purification, column chromatography, gel electrophoresis and the like. Usually, antibody chains are expressed with signal sequences and are thus released to the culture media. However, if antibody chains are not naturally secreted by host cells, the antibody chains can be released by treatment with mild detergent. Antibody chains can then be purified by conventional methods including ammonium sulfate precipitation, affinity chromatography to immobilized target, column chromatography, gel electrophoresis and the like (see generally Scopes, *Protein Purification*, Springer-Verlag, N.Y., 1982).

The above methods result in libraries of nucleic acid sequences encoding antibody chains having specific affinity for a chosen target. The libraries of nucleic acids typically have at least 5, 10, 20, 50, 100, 1000, $10^4$, $10^5$, $10^6$, $10^7$, $10^8$, or $10^9$ different members. Usually, no single member constitutes more than 25 or 50% of the total sequences in the library. Typically, at least 25, 50%, 75, 90, 95, 99 or 99.9% of library members encode antibody chains with specific affinity for the target molecules. In the case of double chain antibody libraries, a pair of nucleic acid segments encoding heavy and light chains respectively is considered a library member. The nucleic acid libraries can exist in free form, as components of any vector or transfected as a component of a vector into host cells.

The nucleic acid libraries can be expressed to generate polyclonal libraries of antibodies having specific affinity for a target. The composition of such libraries is determined from the composition of the nucleotide libraries. Thus, such libraries typically have at least 5, 10, 20, 50, 100, 1000, $10^4$, $10^5$, $10^6$, $10^7$, $10^8$, or $10^9$ members with different amino acid composition. Usually, no single member constitutes more than 25 or 50% of the total polypeptides in the library. The percentage of antibody chains in an antibody chain library having specific affinity for a target is typically lower than the percentage of corresponding nucleic acids encoding the antibody chains. The difference is due to the fact that not all polypeptides fold into a structure appropriate for binding despite having the appropriate primary amino acid sequence to support appropriate folding. In some libraries, at least 25, 50, 75, 90, 95, 99 or 99.9% of antibody chains have specific affinity for the target molecules. Again, in libraries of multi-chain antibodies, each antibody (such as a Fab or intact antibody) is considered a library member. The different antibody chains differ from each other in terms of fine binding specificity and affinity for the target. Some such libraries comprise members binding to different epitopes on the same antigen. Some such libraries comprises at least two members that bind to the same antigen without competing with each other.

Polyclonal libraries of human antibodies resulting from the above methods are distinguished from natural populations of human antibodies both by the high percentages of high affinity binders in the present libraries, and in that the present libraries typically do not show the same diversity of antibodies present in natural populations. The reduced diversity in the present libraries is due to the nonhuman transgenic animals that provide the source materials not including all human immunoglobulin genes. For example, some polyclonal antibody libraries are free of antibodies having lambda light chains. Some polyclonal antibody libraries of the invention have antibody heavy chains encoded by fewer than 10, 20, 30 or 40 $V_H$ genes. Some polyclonal antibody libraries of the invention have antibody light chains encoded by fewer than 10, 20, 30 or 40 $V_L$ genes.

Modified Antibodies

Also included in the invention are modified antibodies to cell surface receptors, e.g., activated integrin receptors, on metastatic cells.

"Modified antibody" refers to antibodies and derivatives of human single chain Fv (scFv) antibody fragments optimized chemically or by molecular engineering into different formats, including but not limited to diabodies, triabodies or bispecific antibodies, pegylated derivatives, variants derived from molecular evolution to enhance affinity, stability, or valency. Modified antibodies also include formats such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody.

The antibody conjugates of the invention can be used to modify a given biological response or create a biological response (e.g., to recruit effector cells). The drug moiety is not to be construed as limited to classical chemical therapeutic agents. For example, the drug moiety can be a protein or polypeptide possessing a desired biological activity. Such proteins can include, for example, an enzymatically active toxin, or active fragment thereof, such as abrin, ricin A, pseudomonas exotoxin, or diphtheria toxin; a protein such as tumor necrosis factor or interferon-alpha; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth. factors. Other derivatives can include antibody fusion proteins with apoptosis inducing moieties such as TRIAL, tumor necrosis factor-related apoptosis-inducing ligand, and reporter molecules such as luciferase or fluorescent probes and nano-particles for non-invasive imaging or targeted delivery of pay-load molecules to sites with tumor burden and micro- and macro-metastases.

In certain preferred embodiments of the invention, the antibodies and antibody compositions of the invention, for example, can be coupled or conjugated to one or more therapeutic or cytotoxic moieties. As used herein, "cytotoxic moiety" simply means a moiety that inhibits cell growth or promotes cell death when proximate to or absorbed by a cell. Suitable cytotoxic moieties in this regard include radioactive agents or isotopes (radionuclides), chemotoxic agents such as differentiation inducers, inhibitors and small chemotoxic drugs, toxin proteins and derivatives thereof, as well as nucleotide sequences (or their antisense sequence). Therefore, the cytotoxic moiety can be, by way of non-limiting example, a chemotherapeutic agent, a photoactivated toxin or a radioactive agent.

In general, therapeutic agents can be conjugated to the antibodies and antibody compositions of the invention, for example, by any suitable technique, with appropriate consideration of the need for pharmokinetic stability and reduced overall toxicity to the patient. A therapeutic agent can be coupled to a suitable antibody moiety either directly or indirectly (e.g. via a linker group). A direct reaction between an agent and an antibody is possible when each possesses a functional group capable of reacting with the other. For example, a nucleophilic group, such as an amino or sulfhydryl group, can be capable of reacting with a carbonyl-containing group, such as an anhydride or an acid halide, or with an alkyl group containing a good leaving group (e.g., a halide). Alternatively, a suitable chemical linker group can be used. A linker group can function as a spacer to distance an antibody from an agent in order to avoid interference with binding capabilities. A linker group can also serve to increase the chemical reactivity of a substituent on a moiety or an antibody, and thus increase the coupling efficiency. An increase in chemical reactivity can also facilitate the use of moieties, or functional groups on moieties, which otherwise would not be possible.

Suitable linkage chemistries include maleimidyl linkers and alkyl halide linkers (which react with a sulfhydryl on the antibody moiety) and succinimidyl linkers (which react with a primary amine on the antibody moiety). Several primary amine and sulfhydryl groups are present on immunoglobulins, and additional groups can be designed into recombinant immunoglobulin molecules. It will be evident to those skilled in the art that a variety of bifunctional or polyfunctional reagents, both homo- and hetero-functional (such as those described in the catalog of the Pierce Chemical Co., Rockford, Ill.), can be employed as a linker group. Coupling can be effected, for example, through amino groups, carboxyl groups, sulfhydryl groups or oxidized carbohydrate residues (see, e.g., U.S. Pat. No. 4,671,958).

As an alternative coupling method, cytotoxic agents can be coupled to the antibodies and antibody compositions of the invention, for example, through an oxidized carbohydrate group at a glycosylation site, as described in U.S. Pat. Nos. 5,057,313 and 5,156,840. Yet another alternative method of coupling the antibody and antibody compositions to the cytotoxic or imaging moiety is by the use of a non-covalent binding pair, such as streptavidin/biotin, or avidin/biotin. In these embodiments, one member of the pair is covalently coupled to the antibody moiety and the other member of the binding pair is covalently coupled to the cytotoxic or imaging moiety.

Where a cytotoxic moiety is more potent when free from the antibody portion of the immunoconjugates of the present invention, it can be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

It can be desirable to couple more than one therapeutic, cytotoxic and/or imaging moiety to an antibody or antibody composition of the invention. By poly-derivatizing the antibodies of the invention, several cytotoxic strategies can be simultaneously implemented, an antibody can be made useful as a contrasting agent for several visualization techniques, or a therapeutic antibody can be labeled for tracking by a visualization technique. In one embodiment, multiple molecules of a cytotoxic moiety are coupled to one antibody molecule. In another embodiment, more than one type of moiety can be coupled to one antibody. For instance, a therapeutic moiety, such as an polynucleotide or antisense sequence, can be conjugated to an antibody in conjunction with a chemotoxic or radiotoxic moiety, to increase the effectiveness of the chemo- or radiotoxic therapy, as well as lowering the required dosage necessary to obtain the desired therapeutic effect. Regardless of the particular embodiment, immunoconjugates with more than one moiety can be prepared in a variety of ways. For example, more than one moiety can be coupled directly to an antibody molecule, or linkers that provide multiple sites for attachment (e.g., dendrimers) can be used. Alternatively, a carrier with the capacity to hold more than one cytotoxic moiety can be used.

As explained above, a carrier can bear the agents in a variety of ways, including covalent bonding either directly or via a linker group, and non-covalent associations. Suitable covalent-bond carriers include proteins such as albumins (e.g., U.S. Pat. No. 4,507,234), peptides, and polysaccharides such as aminodextran (e.g., U.S. Pat. No. 4,699,784), each of which have multiple sites for the attachment of moieties. A carrier can also bear an agent by non-covalent associations, such as non-covalent bonding or by encapsulation, such as within a liposome vesicle (e.g., U.S. Pat. Nos. 4,429,008 and 4,873,088). Encapsulation carriers are especially useful in chemotoxic therapeutic embodiments, as they can allow the therapeutic compositions to gradually release a chemotoxic moiety over time while concentrating it in the vicinity of the target cells.

Preferred radionuclides for use as cytotoxic moieties are radionulcides which are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use. $^{131}$I is particularly preferred, as are other .beta.-radiation emitting nuclides, which have an effective range of several millimeters. $^{123}$I, $^{125}$I, $^{131}$I, or $^{211}$At can be conjugated to antibody moieties for use in the compositions and methods utilizing any of several known conjugation reagents, including lodogen, N-succinimidyl 3-[$^{211}$At]astatobenzoate, N-succinimidyl 3-[$^{131}$I]iodobenzoate (SIB), and, N-succinimidyl 5-[$^{131}$I]iodob-3-pyridinecarboxylate (SIPC). Any iodine isotope can be utilized in the recited iodo-reagents. Other radionuclides can be conjugated to the antibody or antibody compositions of the invention by suitable chelation agents known to those of skill in the nuclear medicine arts.

Preferred chemotoxic agents include small-molecule drugs such as methotrexate, and pyrimidine and purine analogs. Preferred chemotoxin differentiation inducers include phorbol esters and butyric acid. Chemotoxic moieties can be directly conjugated to the antibody or antibody compositions of the invention via a chemical linker, or can encapsulated in a carrier, which is in turn coupled to the antibody or antibody compositions of the invention.

Preferred toxin proteins for use as cytotoxic moieties include ricin, abrin, diphtheria toxin, cholera toxin, gelonin, *Pseudomonas exotoxin, Shigella toxin,* pokeweed antiviral protein, and other toxin proteins known in the medicinal biochemistry arts. As these toxin agents can elicit undesirable immune responses in the patient, especially if injected intravascularly, it is preferred that they be encapsulated in a carrier for coupling to the antibody and antibody compositions of the invention.

The cytotoxic moiety of the immunotoxin may be a cytotoxic drug or an enzymatically active toxin of bacterial or plant origin, or an enzymatically active fragment ("A chain") of such a toxin. Enzymatically active toxins and fragments thereof used are diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolacca americana proteins (PAPI, PAPII, and PAP-S), momordica charantia inhibitor, curcin, crotin, sapaonaria officinalis inhibitor, gelonin, mitogellin, restrictocin, phenomycin, and enomycin. In another embodiment, the antibodies are conjugated to small molecule anti-cancer drugs. Conjugates of the monoclonal antibody and such cytotoxic moieties are made using a variety of bifunctional protein coupling agents. Examples of such reagents are SPDP, IT, bifunctional derivatives of imidoesters such a dimethyl adipimidate HC1, active esters such as disuccinimidyl suberate, aldehydes such as glutaraldehyde, bis-azido compounds such as bis (p-azidobenzoyl) hexanediamine, bis-diazonium derivatives such as bis-(p-diazoniumbenzoyl)-ethylenediamine, diisocyanates such as tolylene 2,6-diisocyanate, and bis-active fluorine compounds such as 1,5-difluoro-2,4-dinitrobenzene. The lysing portion of a toxin may be joined to the Fab fragment of antibodies.

Advantageously, the antibodies and antibody compositions of the invention specifically binding the external domain of the target receptor, e.g. the activated αβ3 integrin receptor, can be conjugated to ricin A chain. Most advantageously the ricin A chain is deglycosylated and produced through recombinant means. An advantageous method of making the ricin immunotoxin is described in Vitetta et al., *Science* 238, 1098, 1987, which is incorporated by reference in its entirety.

The term "contacted" when applied to a cell is used herein to describe the process by which an antibody, antibody composition, cytotoxic agent or moiety, gene, protein and/or antisense sequence, is delivered to a target cell or is placed in direct proximity with the target cell. This delivery may be in vitro or in vivo and may involve the use of a recombinant vector system.

In another aspect, the present invention features an antibody or antibody composition of the invention, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates which include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, duocarmycin, saporin, dihydroxy anthracin didne, mitoxantrone, mithramycin, actinomycin D, 1-dehydrotestosterone, glucocorticoids, procaine, tetracaine, lidocaine, propranolol, and puromycin and analogs or homologs thereof.

Suitable therapeutic agents for forming immunoconjugates of the invention include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin (adriamycin), cisplatin bleomycin sulfate, carmustine, chlorambucil, cyclophosphamide hydroxyurea or ricin A.

Antibodies and antibody compositions of the invention also can be conjugated to a radiotoxin, e.g., radioactive iodine, to generate cytotoxic radiopharmaceuticals for treating, for example, a cancer. The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known. See, e.g., Arnon et al., "Monoclonal Antibodies For Immunotargeting Of Drugs In Cancer Therapy", in Reisfeld et al., eds., *Monoclonal Antibodies And Cancer Therapy*, Alan R. Liss, Inc., pp. 243-56, 1985); Hellstrom et al., "Antibodies For Drug Delivery", in *Controlled Drug Delivery* 2nd Ed., Marcel Dekker, Inc., Robinson et al., eds., pp. 623-53, 1987; Thorpe, "Antibody Carriers Of Cytotoxic Agents In Cancer Therapy: A Review", in *Monoclonal Antibodies '84: Biological And Clinical Applications,* Pinchera et al., eds., pp. 475-506, 1985; "Analysis, Results, And Future Prospective Of The Therapeutic Use Of Radiolabeled Antibody In Cancer Therapy", in *Monoclonal Antibodies For Cancer Detection And Therapy,* Baldwin et al., eds., Academic Press, pp. 303-16 1985, and Thorpe et al., "The Preparation And Cytotoxic Properties Of Antibody-Toxin Conjugates", *Immunol. Rev.,* 62: 119-58, 1982.

Uses of Polypeptides or Antibody Compositions

Each of the polypeptides or antibody compositions, e.g., antibodies to cell surface receptors, cell surface receptor, such as, activated integrin receptor on a metastatic cell, identified herein can be used in numerous ways. The following description should be considered exemplary and utilizes known techniques.

A polypeptide or antibody composition of the present invention can be used to assay protein levels in a biological sample using antibody-based techniques. For example, protein expression in tissues can be studied with classical immunohistological methods. Jalkanen et al., *J. Cell. Biol.* 101: 976-985, 1985; Jalkanen et al., *J. Cell. Biol.* 105: 3087-3096, 1987. Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agent, such as iodine ($^{125}$I, $^{121}$I), carbon ($^{14}$C), sulfur ($^{35}$S), tritium ($^{3}$H), indium ($^{112}$In), and technetium ($^{99}$mTc), and fluorescent labels, such as fluorescein and rhodamine, and biotin.

In addition to assaying secreted protein levels in a biological sample, proteins or antibody compositions can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant scFv clone.

A protein-specific antibody or antibody fragment which has been labeled with an appropriate detectable imaging moiety, such as a radioisotope (for example, $^{131}$I, $^{112}$In, $^{99}$mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled antibody or antibody fragment will then preferentially accumulate at the location of cells which contain the specific protein. In vivo tumor imaging is described in Burchiel et al., *Tumor Imaging: The Radiochemical Detection of Cancer* 13, 1982.

Thus, the invention provides a diagnostic method of a disorder, which involves (a) assaying the expression of a polypeptide by measuring binding of an antibody composition of the present invention in cells or body fluid of an individual; (b) comparing the level of gene expression with a standard gene expression level, whereby an increase or decrease in the assayed polypeptide gene expression level compared to the standard expression level is indicative of a disorder.

Moreover, polypeptides or antibody compositions of the present invention can be used to treat disease. For example, patients can be administered a polypeptide or antibody compositions of the present invention in an effort to replace absent or decreased levels of the polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibody compositions of the present invention can also be used to treat disease. For example, administration of an antibody directed to a polypeptide of the present invention can bind and reduce overproduction of the polypeptide. Similarly, administration of an antibody can activate the polypeptide, such as by binding to a polypeptide bound to a membrane receptor.

Pharmaceutical Compositions

Antibody compositions that specifically binds to an activated integrin receptor on a metastatic tumor cell, ligand mimetics, derivatives and analogs thereof, useful in the present compositions and methods can be administered to a human patient per se, in the form of a stereoisomer, prodrug, pharmaceutically acceptable salt, hydrate, solvate, acid salt hydrate, N-oxide or isomorphic crystalline form thereof, or in the form of a pharmaceutical composition where the compound is mixed with suitable carriers or excipient(s) in a therapeutically effective amount, for example, cancer or metastatic cancer.

Pharmaceutically acceptable carriers are determined in part by the particular composition being administered, as well as by the particular method used to administer the composition. Accordingly, there is a wide variety of suitable formulations of pharmaceutical compositions for administering the antibody compositions (see, e.g., *Remington's Pharmaceutical Sciences,* Mack Publishing Co., Easton, Pa. 18$^{th}$ ed., 1990, incorporated herein by reference). The pharmaceutical compositions generally comprise a differentially expressed protein, agonist or antagonist in a form suitable for administration to a patient. The pharmaceutical compositions are generally formulated as sterile, substantially isotonic and in full compliance with all Good Manufacturing Practice (GMP) regulations of the U.S. Food and Drug Administration.

Diagnostic Use

Characteristics of Antibodies and Antibody Compositions of the invention for Use as Diagnostic Reagents. Human antibodies for use in diagnostic methods to identify metastatic tumor cells, e.g., metastatic breast cancer cells, are preferably produced using the methods described above. The methods result in virtually unlimited numbers of antibodies and antibody compositions of the invention of any epitope binding specificity and very high binding affinity to any desired antigen. In general, the higher the binding affinity of an antibody for its target, the more stringent wash conditions can be performed in an immunoassay to remove nonspecifically bound material without removing target antigen. Accordingly, antibodies and antibody compositions of the invention used in the above assays usually have binding affinities of at least $10^8$, $10^9$, $10^{10}$, $10^{11}$ or $10^{12}$ M$^{-1}$. Further, it is desirable that antibodies used as diagnostic reagents have a sufficient on-rate to reach equilibrium under standard conditions in at least 12 hours, preferably at least five hours and more preferably at least one hour.

Antibodies and antibody compositions of the invention used in the claimed methods preferably have a high immunoreactivity, that is, percentages of antibodies molecules that are correctly folded so that they can specifically bind their target antigen. Such can be achieved by expression of sequences encoding the antibodies in *E. coli* as described above. Such expression usually results in immunoreactivity of at least 80%, 90%, 95% or 99%.

Some methods of the invention employ polyclonal preparations of antibodies and antibody compositions of the invention as diagnostic reagents, and other methods employ monoclonal isolates. The use of polyclonal mixtures has a number of advantages with respect to compositions made of one monoclonal antibody. By binding to multiple sites on a target, polyclonal antibodies or other polypeptides can generate a stronger signal (for diagnostics) than a monoclonal that binds to a single site. Further, a polyclonal preparation can bind to numerous variants of a prototypical target sequence (e.g., allelic variants, species variants, strain variants, drug-induced escape variants) whereas a monoclonal antibody may bind only to the prototypical sequence or a narrower range of variants thereto. However, monoclonal antibodies are advantageous for detecting a single antigen in the presence or potential presence of closely related antigens.

In methods employing polyclonal human antibodies prepared in accordance with the methods described above, the preparation typically contains an assortment of antibodies with different epitope specificities to the intended target antigen. In some methods employing monoclonal antibodies, it is desirable to have two antibodies of different epitope binding specificities. A difference in epitope binding specificities can be determined by a competition assay.

Samples and Target. Although human antibodies can be used as diagnostic reagents for any kind of sample, they are most useful as diagnostic reagents for human samples. Samples can be obtained from any tissue or body fluid of a patient. Preferred sources of samples include, whole blood, plasma, semen, saliva, tears, urine, fecal material, sweat, buccal, skin and hair. Samples can also be obtained from biopsies of internal organs or from cancers. Samples can be obtained from clinical patients for diagnosis or research or can be obtained from undiseased individuals, as controls or for basic research.

The methods can be used for detecting any type of target antigen. Exemplary target antigens including bacterial, fungal and viral pathogens that cause human disease, such as. HIV, hepatitis (A, B, & C), influenza, herpes, *Giardia, malaria, Leishmania, Staphylococcus aureus, Pseudomonas aeruginosa*. Other target antigens are human proteins whose expression levels or compositions have been correlated with human disease or other phenotype. Examples of such antigens include adhesion proteins, hormones, growth factors, cellular receptors, autoantigens, autoantibodies, and amyloid deposits. Other targets of interest include tumor cell antigens, such as carcinoembryonic antigen. Other antigens of interest are class I and class II MHC antigens.

Formats for Diagnostic Assays. Human antibodies can be used to detect a given target in a variety of standard assay formats. Such formats include immunoprecipitation, Western blotting, ELISA, radioimmunoassay, and immunometric assays. See Harlow & Lane, supra; U.S. Pat. Nos. 3,791,932; 3,839,153; 3,850,752; 3,879,262; 4,034,074; 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876, each incorporated herein by reference in their entirety and for all purposes.

Immunometric or sandwich assays are a preferred format. See U.S. Pat. Nos. 4,376,110; 4,486,530; 5,914,241; and 5,965,375, each incorporated herein by reference in their entirety and for all purposes. Such assays use one antibody or population of antibodies immobilized to a solid phase, and another antibody or population of antibodies in solution. Typically, the solution antibody or population of antibodies is labelled. If an antibody population is used, the population typically contains antibodies binding to different epitope specificities within the target antigen. Accordingly, the same population can be used for both solid phase and solution antibody. If monoclonal antibodies are used, first and second monoclonal antibodies having different binding specificities are used for the solid and solution phase. Solid phase and solution antibodies can be contacted with target antigen in either order or simultaneously. If the solid phase antibody is contacted first, the assay is referred to as being a forward assay. Conversely, if the solution antibody is contacted first, the assay is referred to as being a reverse assay. If target is contacted with both antibodies simultaneously, the assay is referred to as a simultaneous assay. After contacting the target with antibody, a sample is incubated for a period that usually varies from about 10 min to about 24 hr and is usually about 1 hr. A wash step is then performed to remove components of the sample not specifically bound to the antibody being used as a diagnostic reagent. When solid phase and solution antibodies are bound in separate steps, a wash can be performed after either or both binding steps. After washing, binding is quantified, typically by detecting label linked to the solid phase through binding of labelled solution antibody. Usually for a given pair of antibodies or populations of antibodies and given reaction conditions, a calibration curve is prepared from samples containing known concentrations of target antigen. Concentrations of antigen in samples being tested are then read by interpolation from the calibration curve. Analyte can be measured either from the amount of labelled solution antibody bound at equilibrium or by kinetic measurements of bound labelled solution antibody at a series of time points before equilibrium is reached. The slope of such a curve is a measure of the concentration of target in a sample Suitable supports for use in the above methods include, for example, nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™. (Amersham Pharmacia Biotech, Piscataway N.J., and the like. Immobilization can be by absorption or by covalent attachment. Optionally, antibodies can be joined to a linker molecule, such as biotin for attachment to a surface bound linker, such as avidin.

Labels

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^{3}H$, $^{14}C$, $^{35}S$, $^{125}I$, $^{121}I$, $^{112}In$, $^{99}mTc$), other imaging agents such as microbubbles (for ultrasound imaging), $^{18}F$, $^{11}C$, $^{15}O$, (for Positron emission tomography), $^{99m}TC$, $^{111}In$ (for Single photon emission tomography), enzymes (e.g., horse radish peroxidase, alkaline phosphatase and others commonly used in an ELISA), and calorimetric labels such as colloidal gold or colored glass or plastic (e.g. polystyrene, polypropylene, latex, and the like) beads. Patents that described the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also *Handbook of Fluorescent Probes and Research Chemicals*, 6$^{th}$ Ed., Molecular Probes, Inc., Eugene Oreg.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, and the like Chemiluminescent compounds include luciferin, and 2,3-dihydrophthalazinediones, e.g., luminol. For a review of various labeling or signal producing systems which may be used, see, U.S. Pat. No. 4,391,904, incorporated herein by reference in its entirety and for all purposes.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Frequently, the activated integrin receptor or αvβ3 integrin receptor proteins and antibodies to activated integrin receptor will be labeled by joining, either covalently or non-covalently, a substance which provides for a detectable signal.

Treatment Regimes

The invention provides pharmaceutical compositions comprising one or a combination of antibodies, e.g., antibodies to activated integrin receptor (monoclonal, polyclonal or single chain Fv; intact or binding fragments thereof) formulated together with a pharmaceutically acceptable carrier. Some compositions include a combination of multiple (e.g., two or more) monoclonal antibodies or antigen-binding portions thereof of the invention. In some compositions, each of the antibodies or antigen-binding portions thereof of the composition is a monoclonal antibody or a human sequence antibody that binds to a distinct, pre-selected epitope of an antigen.

In prophylactic applications, pharmaceutical compositions or medicaments are administered to a patient susceptible to, or otherwise at risk of a disease or condition (i.e., an immune disease) in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

Effective Dosages

Effective doses of the antibody compositions of the present invention, e.g., antibodies to activated integrin receptor, for the treatment of immune-related conditions and diseases, e.g., metastic cancer, described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody in the patient. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 µg to 10 mg, or 30-300 µg DNA per patient. Doses for infectious viral vectors vary from 10-100, or more, virions per dose.

Routes of Administration

Antibody compositions for inducing an immune response, e.g., antibodies to activated integrin receptor, for the treatment of immune-related conditions and diseases, e.g., metastic cancer, can be administered by parenteral, topical, intravenous, oral, subcutaneous, intraarterial, intracranial, intraperitoneal, intranasal or intramuscular means for prophylactic as inhalants for antibody preparations targeting brain lesions, and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection on intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in treating various diseases including various immune-related diseases. In the case of tumor metastasis to the brain, agents of the invention can also be administered in conjunction with other agents that increase passage of the agents of the invention across the blood-brain barrier (BBB).

Formulation

Antibody compositions for inducing an immune response, e.g., antibodies to activated integrin receptor, for the treatment of immune-related conditions and diseases, e.g., metastic cancer, are often administered as pharmaceutical compositions comprising an active therapeutic agent, i.e., and a variety of other pharmaceutically acceptable components. (See Remington's Pharmaceutical Science, 15$^{th}$ ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn et al., *Nature* 391: 851, 1998. Co-administration can be achieved by using the components as a mixture or as linked molecules obtained by chemical crosslinking or expression as a fusion protein.

Alternatively, transdermal delivery can be achieved using a skin patch or using transferosomes. Paul et al., *Eur. J. Immunol.* 25: 3521-24, 1995; Cevc et al., *Biochem. Biophys. Acta* 1368: 201-15, 1998.

The pharmaceutical compositions are generally formulated as sterile, substantially isotonic and in full compliance with all Good Manufacturing Practice (GMP) regulations of the U.S. Food and Drug Administration.

Toxicity

Preferably, a therapeutically effective dose of the antibody compositions described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, Kits Also within the scope of the invention are kits comprising the compositions (e.g., monoclonal antibodies, human sequence antibodies, human antibodies, multispecific and bispecific molecules) of the invention and instructions for use. The kit can further contain a least one additional reagent, or one or more additional human antibodies of the invention (e.g., a human antibody having a complementary activity which binds to an epitope in the antigen distinct from the first human antibody). Kits typically include a label indicating the intended use of the contents of the kit. The term label includes any writing, or recorded material supplied on or with the kit, or which otherwise accompanies the kit.

The following cDNA clones described in the specification and further described in the examples below have been deposited with the American Type Culture Collection, 10801 University Boulevard, Manassas, Va. 20110-2209 under the Budapest Treaty on Nov. 12, 2004. The cDNA clone for scFv Bc-12 has been given the ATCC Accession No. indicated: PTA-6303. The cDNA clone for scFv Bc-15 has been given the ATCC Accession No. indicated: PTA-6304.

EXEMPLARY EMBODIMENTS

Example 1

Cell Lines

Human M21 melanoma and UCLA-P3 lung adenocarcinoma cells were from Dr. D. L. Morton, John Wayne Cancer Center, Santa Monica, Calif. M21-L cells were from Dr. D. A. Cheresh, The Scripps Research Institute. M21-L4 and M21-L12 cells were described in Felding-Habermann et al., *Clin. Exp. Metastasis* 19: 427-436, 2002. MDA-MB 435 human breast cancer cells were from Dr. J. E. Price, M.D. Anderson Cancer Center, Houston, Tex. Variants from this cell line were selected in vivo from lung (Lung) or bone (Bone) metastases upon injecting the parental cells into the mammary fat pad of immune deficient mice. A β3 integrin negative variant (β3-) was selected in vitro by treating the parental cells with an anti-β3 saporin conjugate. β3-cells were transfected either with β3 wild type ($β3_{WT}$) or mutant $β3_{D723R}$ ($β3_{D723R}$) cDNA. Felding-Habermann, et al., *Proc. Natl. Acad. Sci. U.S.A* 98: 1853-1858, 2001. Primary metastatic cells from blood samples of stage IV breast cancer patients (BCM1, BCM2, BMS) were isolated by immuno magnetic bead sorting with antiepithelial antibody BerEP4 (Dynal). These cells express integrin αvβ3 at levels comparable to those of the MDA-MB 435 cell variants. Rolli et al., *Proc. Natl. Acad. Sci. U.S.A* 100: 9482-9487, 2003. Cells were cultured in EMEM, 10% FBS, pyruvate, L-glutamine, vitamins, and nonessential amino acids.

Example 2 scFv Antibody Library and Phage Display

A single-chain Fv antibody library was generated from total RNA of peripheral blood lymphocytes from 20 cancer patients, 5 of whom had breast cancer. From this library, phage displaying scFvs on gene III were rescued as detailed. Mao et al., *Proc. Natl. Acad. Sci. U.S.A.* 96: 6953-6958, 1999.

Proteins. Recombinant tissue necrosis factor-α (TNF-α) (trimer, 51 kDa) was kindly provided by Siliang Hu (Shanghai Research Center of Biotechnology, Chinese Academy of Sciences, Shanghai, China). BSA (66 kDa), staphylococcal enterotoxin B (SEB) (28.5 kDa), cholera toxin B subunit (CTB) (pentamer, 58 kDa), *Ricinus communis* agglutinin ($RCA_{120}$, 120 kDa; "ricin" $RCA_{60}$, 60 kDa) were purchased from Sigma.

Construction of Phage-Display Vector pCGMT9. The vector pCGMT9 was derived from pCGMT. The gene IX (gIX) was amplified by PCR from single-stranded DNA of helper phage VCSM13 as the template by using primers P9 (5'-AAA TAG ACT AGT GGA GGC GGT GGC TCT ATG AGT GTT TTA GTG TAT TCT-3') (SEQ ID NO: 12), and P9rev (5'-GAT TTA GCT AGC TTA TTA TGA GGA AGT TTC CAT TAA ACG-3') (SEQ ID NO: 13). The PCR product was digested by SpeI and NheI and inserted into the pCGMT vector, which was cut with the same restriction enzymes. SpeI digestion and further DNA sequencing was used to characterize the orientation of gIX in the vector.

Preparation of the cDNA Template. Total RNA was prepared from 10 different samples of human peripheral blood lymphocytes (PBLs) by using a RNA Purification kit (Stratagene). First-strand cDNA was synthesized from total RNA by using a First-Strand cDNA Synthesis kit (Amersham Pharmacia) with random hexamers.

Amplification of Antibody Variable Region Genes. Both the $V_H$ and $V_L$ gene repertoires were PCR amplified by using the cDNA and a previously constructed scFv-phage library plasmid as templates. To amplify the $V_H$ and $V_L$ genes from the cDNA and plasmid template, the primers were designed based on those published previously and the most recent gene segments entered in the V-Base sequence directory. All primary PCR reactions were carried out with separate backward primers and combined forward primers. For the amplification of the $V_H$ gene repertoires, 12 separate PCR reactions were set up by using one of 12 different human $V_H$ (HV$_H$) back primers and an equimolar mixture of four human heavy chain J region (HJ$_H$) forward primers. For the κ and λ $V_L$ genes, the same approach was used with 13 separate reactions defined by individual HVκ/HV$_λ$ back primers and a mixture of HJκ/HJ$_λ$ forward primers. PCRs were performed in 100 μl volumes containing 2 μl of cDNA reaction mixture, 2 μM of primer solutions, 200 μM of dNTPs, 5% DMSO, and 10 μl of Pfu polymerase reaction buffer (Stratagene). After 5 min of denaturation at 94° C., 5 units of Pfu polymerase was added, followed by 30 cycles of 1 min at 94° C., 1 min at 57° C., and 1 min at 72° C., and at the end of cycling an incubation of 10 min at 72° C. After PCR, the various reactions afforded $V_H$, Vκ, and $V_λ$ subpools from each of the 10 different PBL samples and scFv-phage library plasmid that were mixed to give three final $V_H$, Vκ, and $V_λ$ pools ready for purification and assembly.

Construction of the scFv Library. The amplified $V_H$ and $V_L$ genes were gel-purified on agarose, and the scFv genes were assembled by overlap PCR using $V_H$ and $V_L$ fragments as templates. First, approximately 20 ng each of $V_H$ and $V_L$ were assembled with a linker by PCR without primers in which the short regions of complementarity built into the ends of the linker promoted hybridization of the various fragments. An initial denaturation step for 5 min at 94° C. was followed by five cycles of 1 min at 94° C., 1 min at 60° C., and 1.5 min at 72° C. in the absence of primers. After adding the outer primers HVH (SfiI) and HJL (SfiI), 30 cycles of 30 s at 94° C., 30 s at 60° C., and 1.5 min at 72° C. were performed. The scFv genes were digested with SfiI, agarose gel-purified, and ligated into the phage-display vector pCGMT9 that had been cut with the same restriction enzyme. The ligated products were electroporated into *Escherichia coli* XLI-Blue competent cells to yield a diversity of $≈4.5×10^9$ independent transformants. After electroporation, cells were plated on LB agar containing 2% glucose, 50 μg/ml carbenicillin, and 20 μg/ml tetracycline in 40 dishes (150 mm×10 mm; Nunc) and incubated overnight at 30° C. The clones were scraped off the plates into 300 ml of superbroth (SB) medium with 10% glycerol and subsequently stored at −70° C.

The phage display library, generated from cancer patient blood lymphocyte cDNA libraries, contained approximately $2×10^8$ clones. In the subtractive panning strategy, clones were isolated that bound specifically to metastatic variants of the human breast cancer cell model and failed to bind to a non-metastatic variant of the same cell model. From these isolated clones, in each of three approaches, 20 clones were arbitrarily picked for further analysis and characterization. For each of these 20 clones, selective binding specificity was verified, comparing the metastatic versus non-metastatic variants of the breast cancer cell model. On average, 2 of the picked 20 clones strictly distinguished between the metastatic versus non-metastatic cell variants, binding only to the metastatic cells. Two clones were further analyzed and characterized in detail (scFvs Bc-12 and Bc-15). The remaining scFvs with specificity for metastatic breast cancer variants indicate that the subtractive panning strategy yields antibodies that react specifically with cells that have established metastatic activity. These antibodies will be characterized further in ongoing studies.

Rescue of scFv-Phage. To rescue the scFv-phage, 1 L of SB medium containing 2% glucose, 50 μg/ml carbenicillin, and 20 μg/ml tetracycline was inoculated overnight with $≈5×10^{10}$ cells from the library glycerol stock. The culture was shaken at 37° C. until $OD_{600}≈0.5$-$0.7$ was obtained. Then, $≈4×10^{13}$ plaque forming units of helper phage VCSM13 and 2 ml of 0.5 M isopropyl β-D-thiogalactopyranoside (IPTG) were added. After 30-min incubation at room temperature, the culture was diluted into 5 liters of SB medium containing 50 μg/ml carbenicillin, 20 μg/ml tetracycline, and 0.5 mM IPETG and grown for 2 h at 30° C. Kanamycin was then added to a final concentration of 70 μg/ml, and the culture was grown overnight at 30° C. Phage were prepared by polyethylene glycol (PEG)/NaCl precipitation.

Panning of scFv-Phage. The library was subjected to three or four rounds of panning. Specifc scFv-phage were affinity selected by using proteins adsorbed to immunotubes (Maxisorb, Nunc). For selection of BSA, TNF-α, SEB, CTB, $RCA_{60}$, and $RCA_{120}$, immunotubes were coated with the individual proteins overnight at room temperature by using 1 ml of 50 μg/ml protein in PBS (10 mM phosphate/150 mM NaCl, pH 7.4) for the first round, 10 μg/ml for the second round, and 5 μg/ml for the third and fourth rounds of panning. The immunotubes were blocked with Blotto (4% skimmed milk in PBS) for 1 h at room temperature and then $≈10^{13}$ cfu scFv-phage were added into the immunotube in 2% skimmed milk/2% BSA in PBS (BSA was omitted when panning against BSA). After 2 h of incubation with rocking at room temperature, the unbound and nonspecifically bound scFv-phage were eluted by using 10 washes with PBS/0.1% Tween-20 and 10 washes with PBS. The specifically bound scFv-phage was eluted with 1 ml elution buffer (100 mM HCl, adjusted to pH 2.2 with solid glycine and containing 0.1% BSA) for 10 min at room temperature. The eluate was neutralized with 60 μl of 2 M Tris base and was used to infect freshly prepared *E. coli* XL1-Blue cells. The scFv-phage were then amplified and rescued as outlined above and entered into the next round of panning.

ELISA of scFv-Phage Binding. Relative affinity and specificity of scFv-phage and soluble scFvs was assessed against the six protein antigens. BSA, TNF-α, SEB, CTB, $RCA_{60}$, and $RCA_{120}$ solutions at 10 μg/ml were coated on a microtiter plate at room temperature overnight. Any remaining binding sites were blocked with Blotto. Approximately 25 μl per well of scFv-phage or soluble scFv supernatant from overnight cell cultures was added and incubated for 1 h at 37° C. For scFv-phageELISA, after washing, 25 μl of anti-M13 mAb horseradish peroxidase (HRP) conjugate (Amersham Pharmacia) diluted 1:1000 in Blotto was added for 30 min at 37° C. For ELISA using soluble scFv, anti-Flag M2 mAb HRP conjugate (Sigma) in Blotto was added and incubated for 30 min at 37° C. Detection was accomplished by adding 50 μl of tetramethylbenzidine substrate (Pierce) and the absorbance was read at 450 nm.

Purification of scFvs and Affinity Measurements. The scFv genes were subcloned into expression vector pETFlag, expressed and purified to homogeneity. Dissociation constants ($K_d$) were calculated from the measured association ($k_{on}$) and dissociation ($k_{off}$) rate constants by using the BIAcore instrumentation and software (Amersham Pharmacia). For BIAcore experiments, protein antigens were immobilized on CM5 chips. After scFv binding measurements, chips were regenerated with 75 mM HCl.

Example 3

Subtractive Panning of Phage Antibodies

Phage displaying antibodies reactive with integrin αvβ3 were isolated by five rounds of subtractive panning on live breast cancer cells. In each round, the library (~$5\times10^{12}$ cfu) was first subtracted on $3\times10^7$ MDA-MB 435 variant cells expressing non activated αvβ3 suspended in serum free EMEM, 1% BSA, for 45 min at RT. The depleted library was then panned on $1\times10^7$ MDA-MB 435 variant cells expressing activated αvβ3. After 30 min at RT, the cells were centrifuged and washed 10 times in EMEM. Bound scFv phage was eluted with 100 mM glycine/HCl, 1% BSA, 150 mM NaCl, pH 2.4, neutralized with 1M Tris/HCl, pH 7.4, amplified in *E. coli* SL-1 Blue, and precipitated with PEG/NaCl for further subtraction, selection, purification or cell binding analysis by flow cytometry.

scFv purification. scFv gene fragments were subcloned into pETFlag (derived from pET-15b, Novagen) and transformed into *E. coli* B834(DE3). Expression was induced with 0.5 mM IPTG, and FLAG-tagged scFv fragments were purified on anti-Flag mAb M2 affinity agarose (Sigma) as described. Mao, S., et al., *Proc. Natl. Acad. Sci. U.S.A* 96: 6953-6958, 1999; Gao, C., et al., *J. Immunol. Methods* 274: 185-197, 2003. Monomeric scFv was purified by Sephacryl-100 FPLC (Amersham Pharmacia).

Flow cytometry. scFv binding to human tumor cells was analyzed by flow cytometry, initially with cloned scFv phage and then with purified scFv protein. Per sample, $2\times10^5$ tumor cells were blocked with goat serum and incubated either with scFv phage ($2-5\times10^{10}$) (1 h at RT) followed by mouse anti-M13 mAb (Serotec) (30 min on ice) and goat FITC-anti mouse (Pierce) (30 min on ice), or with purified scFv (1.25 to 40 µg/ml, routinely 10 to 15 µg/ml) (45 min on ice), followed by mouse anti-FLAG mAb M2 (Sigma) (30 min on ice) and goat FITC-anti mouse. Binding/washing buffer was TBS with or without divalent cations (1 mM $Ca^{2+}$, 1 mM $Mg^{2+}$, 0.2 mM $Mn^{2+}$). Alternatively, tumor cells were washed in 10 ml of plasma (prepared freshly from human blood anticoagulated with 50 nM D-Phe-D-Pro-D-arginyl chloromethyl ketone, PPACK, Felding-Habermann et al., *J. Biol. Chem.* 271: 5892-5900, 1996), resuspended in plasma and then incubated sequentially, without washing, with purified scFv (45 min on ice), followed by anti-FLAG M2 (30 min on ice) and FITC-anti mouse (30 min on ice). All samples were counter stained with propidium iodide (PI) and analyzed on a Becton-Dickinson FACScan, with live gate set to exclude PI positive cells.

Sequence analysis of scFvs. Nucleic acid sequencing of selected clones was carried out on a 373-A DNA sequencer (Applied Biosystems). All sequences were searched in the Kabat database (www.ncbi.nlm.nih.gov/) to compare them with previously sequenced $V_H$ and $V_L$ chains, and in the International Immnogenetics database (www.Genetik.uni-Koeln.de/dnaplot) to propose correlations of scFvs with potential germline gene sequences and assess V-segment usage. The GCG Wisconsin Package was used for alignments.

Cell adhesion and migration. Tumor cell adhesion under stationary conditions was analyzed as detailed earlier (19). Adhesion buffer was Hanks balanced salt solution (HBSS) pH 7.4, 0.5% BSA, 1 mM $MgCl_2$, 0.2 mM $MnCl_2$. For inhibition, cells were incubated for 5 min at RT either with 3 µM scFv or 200 µM GRGDSPK (SEQ ID NO: 11) peptide, then plated in the presence of inhibitor and allowed to attach for 30 min at 37° C. Haptotactic tumor cell migration toward fibrinogen was analyzed in transwell chambers as detailed earlier. Rolli, M., et al., *Proc. Natl. Acad. Sci. U.S.A* 100: 9482-9487, 2003. Before the assay, tumor cells were starved for 16 hrs at 37° C. in serum free EMEM, washed and then allowed to migrate in serum free EMEM in the presence or absence of 2 µM scFv or 200 µM GRGDSPK (SEQ ID NO: 11) peptide for 16 hrs at 37° C., 5% $CO_2$.

Tumor cell arrest during bloodflow. Breast cancer cell arrest during blood flow and interaction with platelets was measured as described. Felding-Habermann, et al., *Proc. Natl. Acad. Sci. U.S.A* 98: 1853-1858, 2001. Felding-Habermann et al., *J. Biol. Chem.* 271: 5892-5900, 1996. Briefly, tumor cells were suspended in human blood anticoagulated with 50 nM PPACK and perfused over a collagen I matrix at a venous wall shear rate of 50 $s^{-1}$, 2 dynes/$cm^2$. Adhesive events and cell interactions were visualized and recorded by fluorescence video microscopy and quantified by image acquisition at 30 predefined positions followed by computerized image analysis (MetaMorph, Universal Imaging). Tumor cells were stained with hydroethidine (red fluorescence) (20 µg/ml, 30 min, 37° C.), washed, and mixed with blood containing 10 µM mepacrine (green fluorescence). Blood cells, tumor cells, and platelets acquired green fluorescence and were visualized at 488/515 nm (excitation/emission). Tumor cells were identified by their unique red fluorescence at 543/590 nm. To test inhibition, tumor cells were incubated with 3 µM scFv for 5 min at 37° C., then mixed into blood, scFv added to 3 µM final concentration and perfused immediately.

Antibody internalization. Breast cancer cells grown in chamber slide wells were incubated with 20 µg/ml FITC-labeled scFv in serum free EMEM for 3 h either at 4° C. or 37° C., washed 10 times, fixed and permeabilized with 95% ethanol, stained with propidium iodide, mounted in antifade solution, and analyzed with a laser scanning confocal microscope.

Experimental metastasis in vivo. $1\times10^5$ BMS human metastatic breast cancer cells were injected into the lateral tail veins of 9 week old female C.B17/lcrTac-Prkdc scid mice (Taconic Farms) (n=8 to 10) together with a 50 µg bolus dose of scFv. I.v. Injections of 50 µg scFv bolus doses were repeated on days 2, 3 and 4 of the experiment. Control animals received vehicle only (PBS). For in vivo use, endotoxin was removed from scFv preparations on Detoxy-Gel resin (Pierce). Remaining traces ranged from 0.001 to 0.07 EU endotoxin/mg scFv (LAL test, Bio Whittaker). On day 32, mice were euthanized, dissected, the lungs excised, fixed in Bouin's solution, and metastatic foci counted at the lung surface under a dissecting microscope. The same lungs were embedded in paraffin, and 10 µm sections were cut and stained with hematoxylin/eosin. Per lung, 7 sets of three consecutive sections were collected, separated by 140 µm. The sections were randomized and coded, and the total number of metastatic foci counted.

To treat mice with established metastatic disease, $5\times10^5$ DsRed2 tagged MDA-MB 435 cells expressing constitutively activated αvβ3$_{D723R}$ were injected intravenously. After all mice in a control group had developed lung metastases after one week, the mice in treatment groups received intravenous injections of 40 µg scFv Bc-15, or scFv Mut-15 as control on day 7, 9, 11, 14, 16, and 18 after tumor cell inoculation. The mice were euthanized on day 19 and lung metastases counted under a fluorescence microscope. Care and use of the animals complied with NIH and AAALAC guidelines.

Example 4

Cancer Patient Derived scFv Antibodies Recognize Tumor Cell Integrin αvβ3 in an Activation Dependent Manner To generate therapeutic reagents that specifically react with activated αvβ3, a phage display library of single chain antibody fragments (scFv) was exploited. This library was derived from cancer patient blood lymphocyte cDNA libraries and allowed us to test the hypothesis that the expressed immune repertoire contains antibodies that recognize integrin αvβ3, and distinguish between its activated and non-activated forms. Mao et al., *Proc. Natl. Acad. Sci. U.S.A* 96: 6953-6958, 1999. A subtractive panning approach was designed based on variants of MDA-MB 435 human breast cancer cells. It has been demonstrated that the majority of the parental cell population expresses non-activated αvβ3, but contains a subset of cells expressing the activated receptor. Apparently, these cells are selected during metastasis, as variant cells isolated from lung and bone metastases in immune deficient mice express constitutively activated αvβ3. To establish a cell population that uniformly expresses non-activated αvβ3, MDA-MB 435 parental cells were cloned by limiting dilution, and clones tested for αvβ3 functionality. Twenty clones were identified, in which the receptor failed to support fibrinogen directed migration and αvβ3 dependent tumor cell arrest during blood flow, confirming a non-activated integrin. The pooled clones, termed Parent Combo, expressed αvβ3 at a level comparable to the parental population. A cell line, MDA-MB 435 Lung-Lung, was established which expressed αvβ3 in a constitutively activated form. This variant stems from a lung metastase of an immune deficient mouse whose mammary fat pad had been injected with parental MDA-MB 435 cells. Felding-Habermann et al., *Proc. Natl. Acad. Sci. U.S.A* 98: 1853-1858, 2001; Rolli et al., *Proc. Natl. Acad. Sci. U.S.A* 100: 9482-9487, 2003. To enrich for the ability to colonize the lung from the blood stream, the Lung variant was subsequently injected intravenously, and tumor cells cultured 3 weeks later from the excised lung. Parent Combo cells were used to subtract the scFv phage library to eliminate antibodies against antigens shared by the MDA-MB 435 cell variants. After 5 rounds of subtracting the phage library on Parent Combo cells and panning on Lung-Lung cells, scFv clones were analyzed by flow cytometry for their ability to bind integrin αvβ3 on human tumor cells, and to distinguish between the activated and non-activated forms of the receptor (FIG. 1). Each clone was tested on a panel of human tumor cells, which either express or lack αvβ3, but express αv or β3 in combination with other integrin subunits. These were M21 melanoma cells (αvβ3, no other β3 integrin), M21-LIIb cells (αIIbβ3, no αv integrin), and UCLA-P3 lung adenocarcinoma cells (αv integrins, but no αvβ3). Two scFv clones, Bc-12 and Bc-15, were identified that reacted only with cells expressing the αvβ3 heterodimer. A third scFv clone, Bc-20, reacted with αv positive cells, regardless of the associated β subunit (FIG. 1A). Bc-12 and Bc-15 failed to bind M21-L cells (no αv integrins)—but did react with M21-L4 cells, in which αvβ3 expression had been restored by transfection, confirming their reactivity with αvβ3. Felding-Habermann, B., et al., *Clin. Exp. Metastasis* 19: 427-436, 2002.

The recognition of αvβ3 by Bc-12 and Bc-15 showed a cation dependence. Binding was measurable in the presence of physiological $Ca^{2+}$ levels and greatly enhanced in the presence of $Mn^{2+}$, a metal ion that can activate integrins (FIG. 1A,B). To test this further, the effects of cation combinations on Bc-12 and Bc-15 binding were examined. $Mg^{2+}$ supported Bc-12 and Bc-15 binding at the same level as $Ca^{2+}$, and $Ca^{2+}$ reduced the enhancing effect of $Mn^{2+}$ (FIG. 1B). ScFv Bc-20 binding to αv-positive cells did not require divalent metal cations. This indicates that scFv Bc-12 and Bc-15 preferentially recognize activated integrin αvβ3 and demonstrates binding requirements reminiscent of natural plasma protein ligands of this receptor, such as fibrinogen, vitronectin and fibronectin. Smith, *Methods Cell Biol.* 69: 247-259, 2002; Hughes et al., *J. Biol. Chem.* 271: 6571-6574, 1996. To confirm that scFv Bc-12 and Bc-15 selectively recognize αvβ3 in its activated form, binding of these antibodies to in vitro generated and in vivo selected variants of the MDA-MB 435 breast cancer cell model was tested. Bc-12 and Bc-15 failed to bind β3-negative MDA-MB 435 cells ($β3^-$) and a β3 wild type expressing derivative of these cells ($β3_{WT}$), the latter of which was, however, recognized when activated with $Mn^{2+}$. The same $Mn^{2+}$ dependence was true for MDA-MB 435 Parent Combo cells which express non-activated αvβ3 (FIG. 1C). In contrast, Bc-12 and Bc-15 were able to bind an MDA-MB 435 variant expressing constitutively activated mutant $αvβ3_{D723R}$, without exogenous stimulation with $Mn^{2+}$. Binding was further enhanced when $Mn^{2+}$ was added. Importantly, scFvs Bc-12 and Bc-15 recognized in vivo selected MDA-MB 435 variants from bone and lung metastases, as well as metastatic cells isolated from breast cancer patient blood samples (FIG. 1C). These cells express αvβ3 in a constitutively activated form. Felding-Habermann et al., *Proc. Natl. Acad. Sci. U.S.A* 98: 1853-1858, 2001; Rolli et al., *Proc. Natl. Acad. Sci. U.S.A* 100: 9482-9487, 2003. Thus, the results indicate that Bc-12 and Bc-15 recognize αvβ3 and require its presentation in an activated, high affinity state.

Figure 2A:
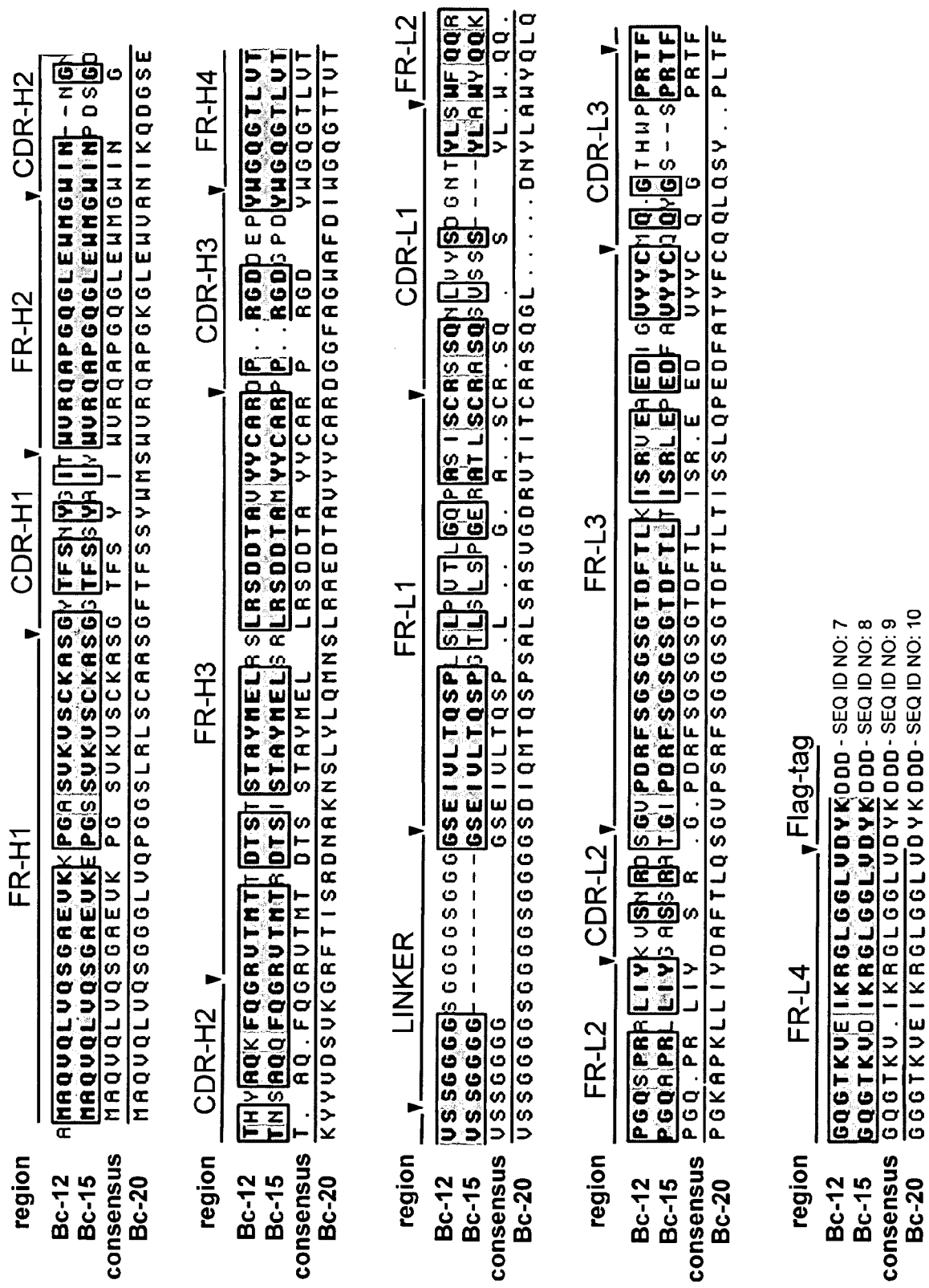
Figure 2B:
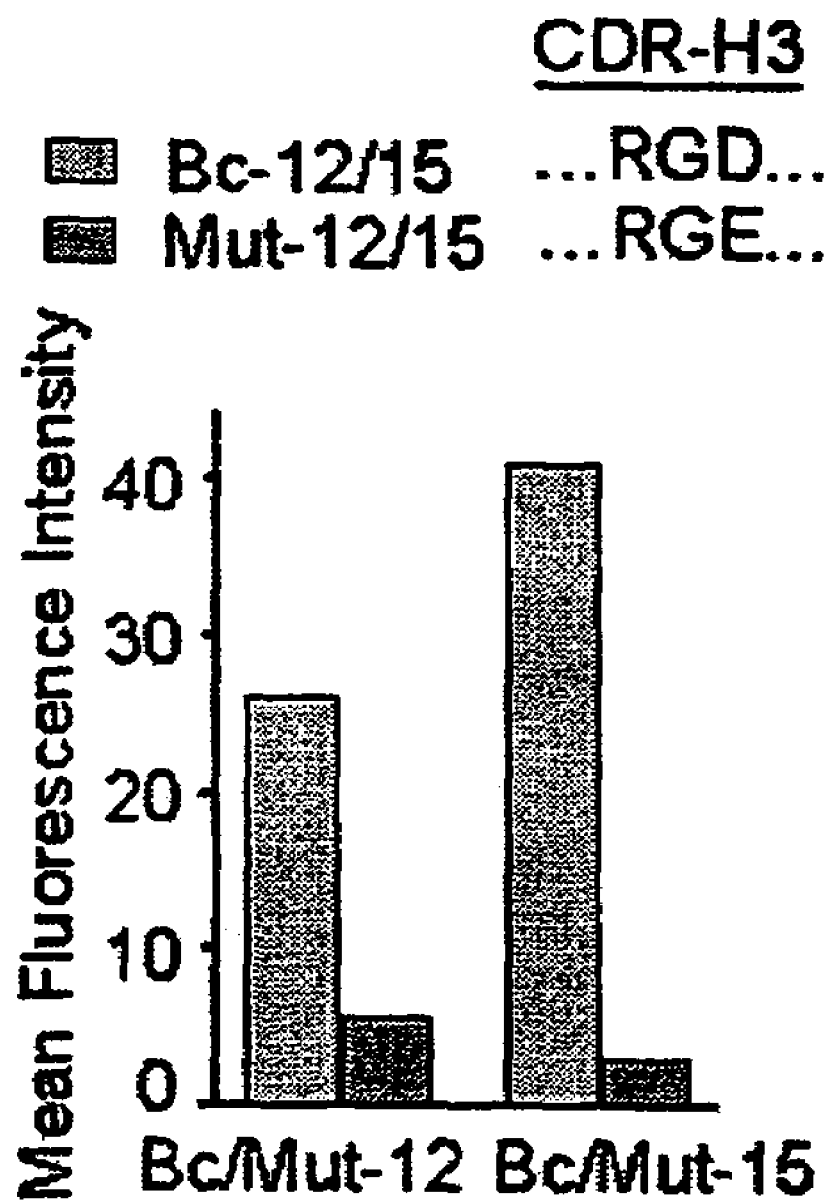

Patient derived scFv antibodies against activated αvβ3 are natural ligand mimetics. The findings that patient derived scFv antibodies Bc-12 and Bc-15 require divalent metal cations for binding to αvβ3 expressing tumor cells, and that the receptor had to be present in an activated functional form, indicate that Bc-12 and Bc-15 resemble natural ligands of αvβ3. To analyze similarities between the scFv antibodies and natural ligands, the DNA sequences of Bc-12, Bc-15 and Bc-20 were determined and translated (FIG. 2A). The DNA sequences of scFv Bc-12 cDNA and scFv Bc-15 cDNA are shown in FIG. 2C. The protein sequence showed that the third complementarity determining regions of the heavy chains (CDR-H3) in Bc-12 and Bc-15 contain an RGD ligand recognition motif. This motif, common to natural αvβ3 ligands, is absent in Bc-20 (FIG. 2). To examine the contribution of the RGD motif in CDR-H3 of scFv antibodies Bc-12 and Bc-15 to their specificity for activated integrin αvβ3, this sequence was changed to RGE by site directed mutagenesis. The D to E exchange within the RGD motif is known to reduce or abolish ligand recognition by αvβ3. Binding of the mutated scFvs to human breast cancer cells was strongly reduced in Mut-12, the RGE version of Bc-12, and abolished in Mut-15, the RGE version of Bc-15 (FIG. 2B). This indicates that RGD binding critically determines antibody-antigen recognition. However, the antibodies did not react with the αvβ3-related platelet integrin αIIbβ3, nor with other αv integrins or α5β1 (FIG. 1), which are known RGD binding receptors. Ruoslahti, *Annu. Rev. Cell Dev. Biol.* 12: 697-715, 1996. This implies that a synergistic binding region may exist, with contributions from both the antibody tertiary structure and the RGD sequence to the observed selective recognition of the activated conformation of αvβ3. The cDNA sequences for scFv Bc-12 and scFv Bc-15 are shown in FIG. 2C. The cDNA sequences for scFv Mut-12 and scFv Mut-15 are shown in FIG. 2D.

Figure 3:
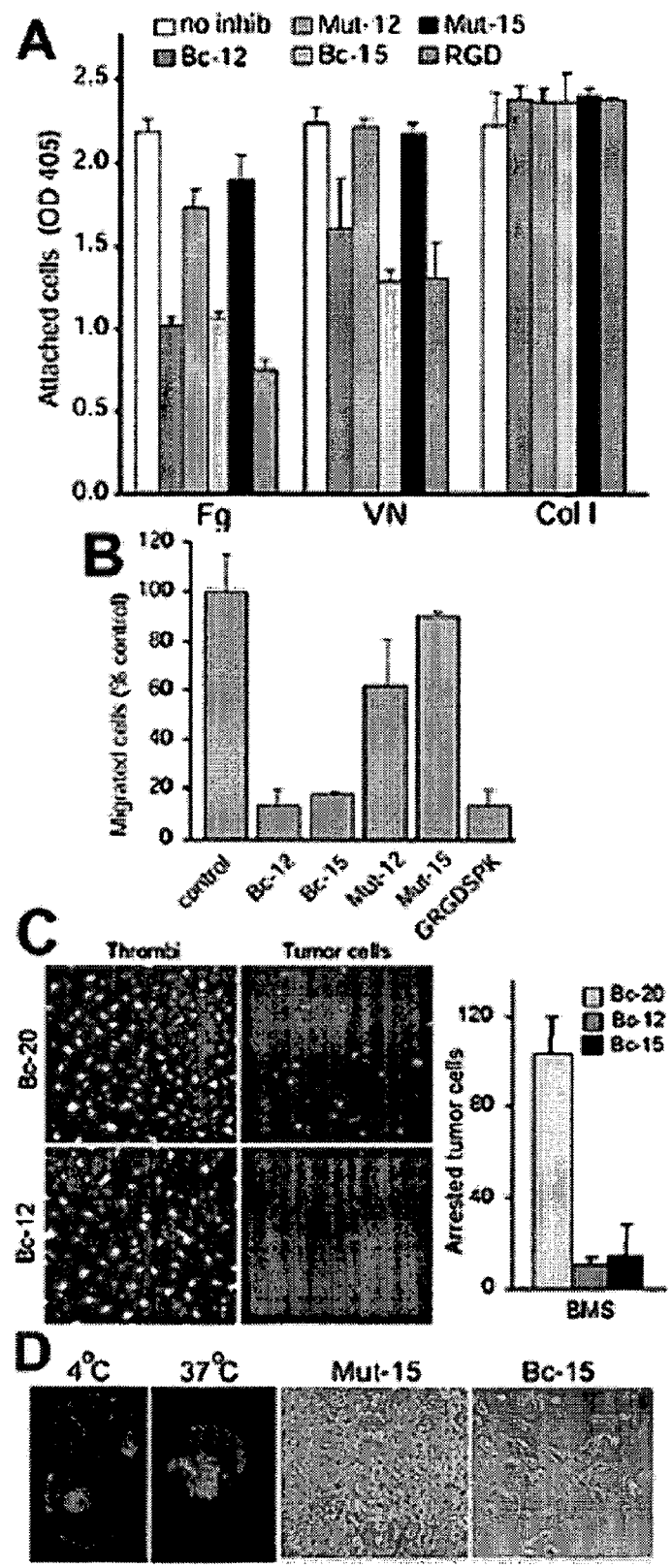
FIGS. 3A, 3B, 3C, 3D, 3E. scFv Bc-12 and Bc-15 inhibit $\alpha v\beta 3$ mediated adhesive breast cancer cell functions. (A) Adhesion of BMS human breast cancer cells to fibrinogen (Fg), vitronectin (VN) or type I collagen (Col I) in the absence or presence of 3 µM Bc-12, Bc-15 or their RGE mutants Mut-12, Mut-15, compared to 200 µM GRGDSPK peptide (SEQ ID NO: 11). Protein coating concentrations: 10 µg/ml (VN, Col I) or 20 µg/ml (Fg). Adhesion time: 30 min at 37° C. (B) Effect of scFvs on haptotactic BMS cell migration toward a fibrinogen substrate (16 hrs at 37° C. in transwell chambers with or without 2 µM Bc-12, Bc-15 or their RGE mutants Mut-12 or Mut-15, compared to 200 µM GRGDSPK peptide) (SEQ ID NO: 11). (C) Effect of scFvs on breast cancer cell arrest during blood flow. Metastatic BMS cells, labeled with hydroethidine, were suspended in human blood (anticoagulated with 50 nM PPACK) and perfused over a collagen I matrix at a venous wall shear rate of 50 $s^{-1}$. Under these conditions, breast cancer cells arrest by $\alpha v\beta 3$ mediated binding to adherent, thrombus forming platelets. Tumor cell adhesion was quantified by image acquisition at 30 predefined positions during blood flow. Left: representative images of platelet signal (thrombi, green fluorescence) and tumor cell signal (red fluorescence) at identical x,y positions. Right: Number of arrested tumor cells in the presence of 3 µM non-function blocking anti $\alpha v$ scFv Bc-20 or function blocking anti $\alpha v\beta 3$ scFvs Bc-12 or Bc-15. (D) scFv Bc-15 is internalized by human breast cancer cells and reduces cell proliferation. Left: confocal images of BMS cells incubated for 4 hrs with FITC-Bc-15 at 4° C. (binding) versus 37° C. (allowing internalization). Right: Phase contrast images of BMS cell cultures 4 days after seeding in the presence of 2 µM RGE containing scFv Mut-15, or RGD containing Bc-15. (E) Effect of scFv Bc-12 on the viability of matrix deprived BMS breast cancer cells in ultra-low-adhesion plates in the presence or absence of 3.7 µM scFv, or 14.36 µM camptothecin as apoptosis inducing control. Measurement of apoptosis was based on cytoplasmic histone-associated DNA fragments after 20 hrs.

Ligand mimetic scFv antibodies inhibit αvβ3 mediated adhesive tumor cell functions. Since the patient derived scFv antibodies Bc-12 and Bc-15 apparently mimic natural ligands of integrin αvβ3, it was hypothesized that these antibodies might interfere with αvβ3 mediated ligand binding and adhesive tumor cell functions. When applied under stationary conditions, Bc-12 and Bc-15 efficiently inhibited adhesion of BMS human breast cancer cells to immobilized fibrinogen, a process that is mediated exclusively by αvβ3 in these cells. Rolli et al., Proc. Natl. Acad. Sci. U.S.A 100: 9482-9487, 2003. The extent of inhibition by 3 μM scFv was similar to that observed with 200 μM GRGDSPK (SEQ ID NO: 11), a fibronectin derived peptide (FIG. 3A). BMS cell attachment to vitronectin was also inhibited by Bc-12 and Bc-15, but to a lesser degree. Adhesion to this protein is mediated by αvβ3 together with other αv integrins on these cells. The antibodies had no effect on breast cancer cell adhesion to collagen type I, which is mediated primarily by BMS cell integrin α2β1 with no involvement of αvβ3. Another function, critical for tumor cell dissemination, is matrix directed migration. Tumor cells often produce vascular permeability factors that cause leakage of adhesive plasma proteins into the tumor area. McDonald et al., Cancer Res. 62: 5381-5385, 2002. Thus, a gradient of fibrinogen and polymerizing fibrin, the most abundant of these proteins, may guide metastatic cells toward tumor supporting blood vessels. In the breast cancer cell model, migration toward immobilized fibrinogen or fibrin is exclusively mediated by integrin αvβ3 and requires the activated state of the receptor. Rolli et al., Proc. Natl. Acad. Sci. U.S.A 100: 9482-9487, 2003. It was therefore examined whether Bc-12 and Bc-15 can impact fibrinogen directed migration. At a 2 μM concentration, Bc-12 and Bc-15 inhibited BMS human breast cancer cell migration almost completely. This effect was similar to that seen with 200 μM GRGDSPK (SEQ ID NO: 11) peptide (FIG. 3B). RGE containing scFv Mut-15 had no effect and Mut-12 only a minor effect on fibrinogen directed migration.

In the circulation, metastatic tumor cells are intensely exposed to a cancer patient's immune surveillance, encountering potential function blocking antibodies like Bc-12 and Bc-15. The hostility of this environment toward metastatic cells is intensified by shear forces generated by blood flow which physically oppose tumor cell arrest within the vasculature, a process necessary for target organ colonization. It has been demonstrated that breast cancer cell integrin αvβ3 in its activated form can support arrest of metastatic cells during blood flow. Therefore experiments were designed to mimic blood flow conditions in the vasculature, and to examine whether the ligand mimetic scFv antibodies could interfere with breast cancer cell arrest. BMS breast cancer cells were prestained with a red fluorescent dye and mixed into human blood, which was spiked with a green fluorescent dye. The mixture was perfused over a thrombogenic collagen I matrix at a venous wall shear rate of 50 $sec^{-1}$. On this matrix, platelets attach easily and become activated. Ruggeri, Nat. Med. 8: 1227-1234, 2002. This triggers local thrombus formation mediated by activated platelet integrin αIIbβ3. Breast cancer cells that express activated integrin αvβ3 can utilize this receptor to interact with platelets during blood flow and attach to thrombi formed at the adhesive surface. Felding-Habermann et al., Proc. Natl. Acad. Sci. U.S.A 98: 1853-1858, 2001. scFv antibodies Bc-12 and Bc-15 efficiently inhibited this process, while the non-RGD containing anti αv antibody Bc-20 had no effect (FIG. 3C). Similar results were obtained with other metastatic breast cancer cell lines. The RGE containing scFv mutants Mut-12 and Mut-15 had no effect on breast cancer cell arrest during blood flow. These results indicate that the ligand mimetic scFv antibodies, which recognize integrin αvβ3 in a functionally activated form, can block breast cancer cell interaction with platelets, and thereby inhibit cancer cell arrest in flowing blood. Integrin αIIbβ3 mediated adhesive platelet functions were not affected by the antibodies (FIG. 3C, left images).

Figure 3E:
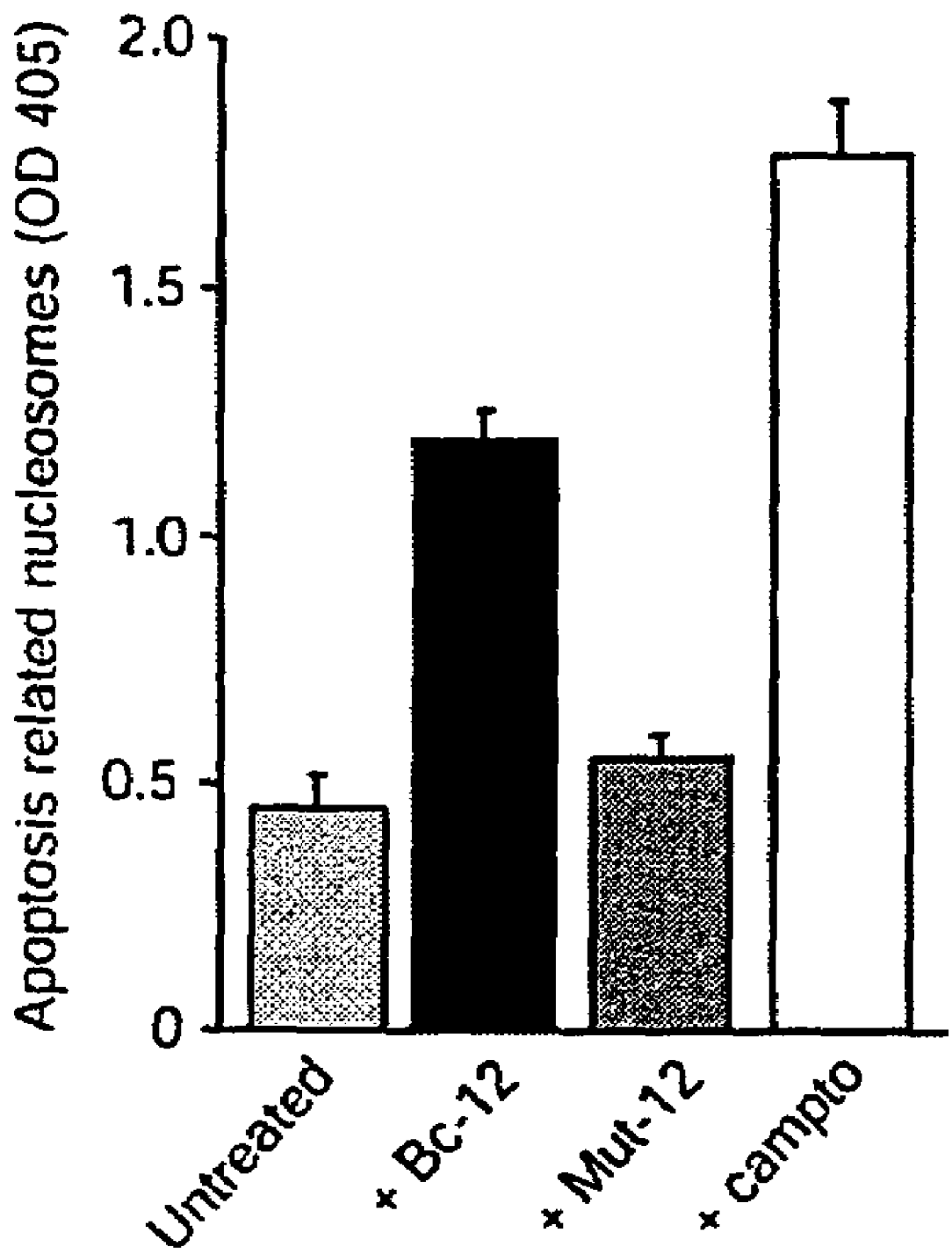

As ligand mimetics, scFvs Bc-12 and Bc-15 may impact not only breast cancer cell adhesive functions but also cell survival. It has been demonstrated that disruption of ligand binding to αvβ3 can stimulate apoptosis. Stupack et al., J. Cell Biol. 155: 459-470, 2001. Through an alternative pathway, internalized RGD containing compounds may directly induce cell death by activating the pro-apoptotic enzyme caspase-3 through an alternative pathway. Buckley et al., Nature 397: 534-539, 1999. scFvs Bc-12 and Bc-15 were efficiently bound and readily internalized by adherent BMS breast cancer cells at permissive temperature. The growth of several human breast cancer cell lines, isolated from patient blood samples, was retarded in the presence of the RGD containing scFvs Bc-12 and Bc-15, while their RGE mutant versions, Mut-12 and Mut-15, had no effect (FIG. 3D). Furthermore, when breast cancer cells were deprived of an adhesive matrix, as occurs in the circulation, exposure to scFv Bc-12 resulted in apoptotic cell death (FIG. 3E). Thus, patient derived, ligand mimetic antibodies can disrupt specific adhesive functions of activated integrin αvβ3 and affect the growth behavior of tumor cells bearing this receptor.

Figure 4:
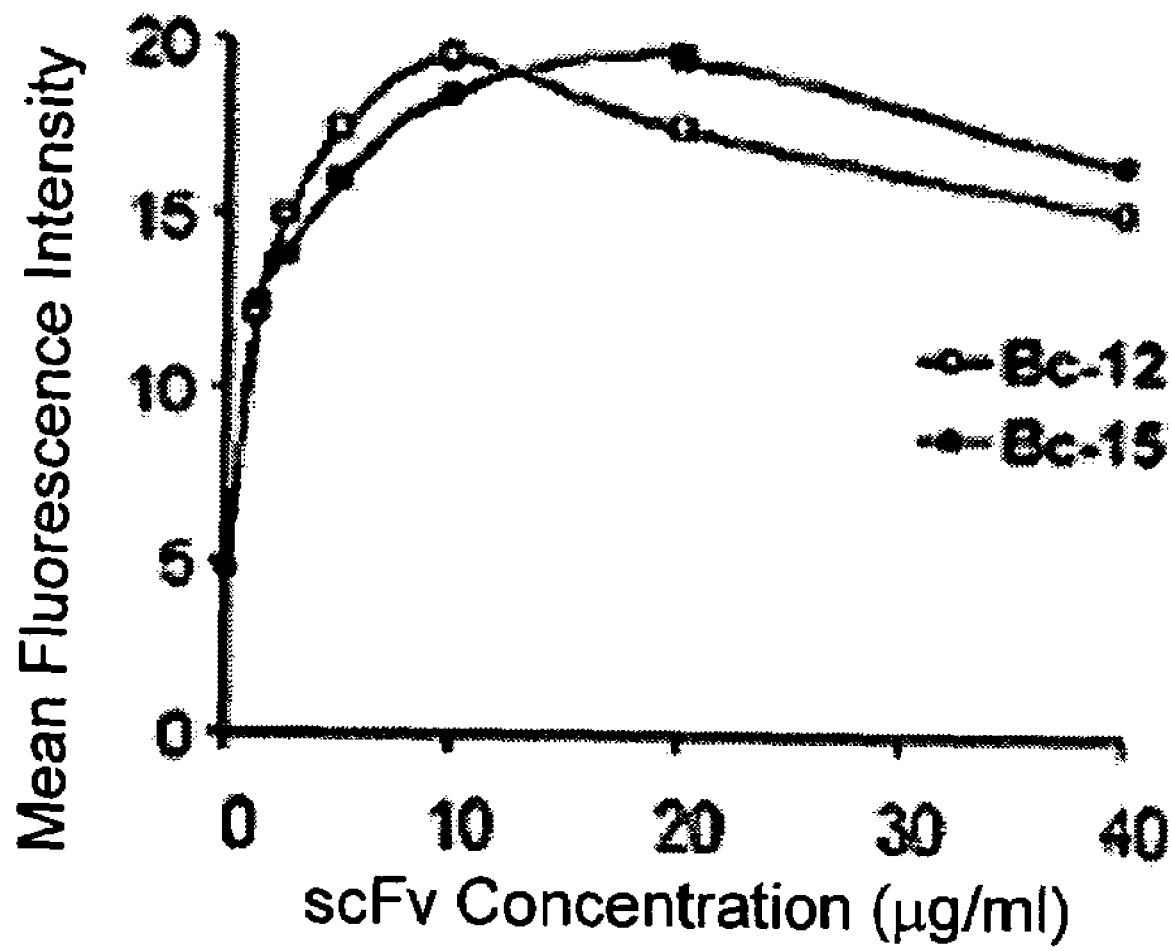
FIG. 4. Patient derived ligand mimetic scFvs Bc-12 and Bc-15 against activated $\alpha v\beta 3$ are internalized and bind to breast cancer cells in human plasma and affect breast cancer survival. Flow cytometric analysis with human metastatic breast cancer cells (BMS) isolated from a patient blood sample. All binding and washing steps were done in fresh human plasma prepared from blood anticoagulated with 50 nM PPACK.

Antimetastatic activity of scFv antibodies against activated αvβ3 inhibit hematogenous breast cancer metastasis in vivo. Having demonstrated that the immune repertoire of cancer patients contains antibodies that specifically recognize the activated, metastasis supporting form of integrin αvβ3, the next critical aspect investigated was whether binding of these antibodies to circulating tumor cells affects metastasis from the blood stream. To be effective in that microenvironment, the antibodies must bind tumor cell integrin αvβ3 in blood or plasma. The blood perfusion studies demonstrated that scFvs Bc-12 and -15 can inhibited breast cancer cell arrest during blood flow, indicating that these antibodies recognize tumor cells under those conditions. To confirm this, BMS breast cancer cells were incubated with increasing concentrations of Bc-12 or -15 in fresh human plasma. The antibodies bound the cells in a saturable manner with half maximal binding measured at 40 nM scFv (1 μg/ml) (FIG. 4). Similar results were obtained with other metastatic breast cancer cell lines. This demonstrates that RGD containing scFv antibodies Bc-12 and Bc-15 bind to tumor cell integrin αvβ3 in the presence of a multitude of RGD containing plasma proteins, the most abundant of which is fibrinogen at a physiological plasma concentration of 6-12 μM.

Figure 5:
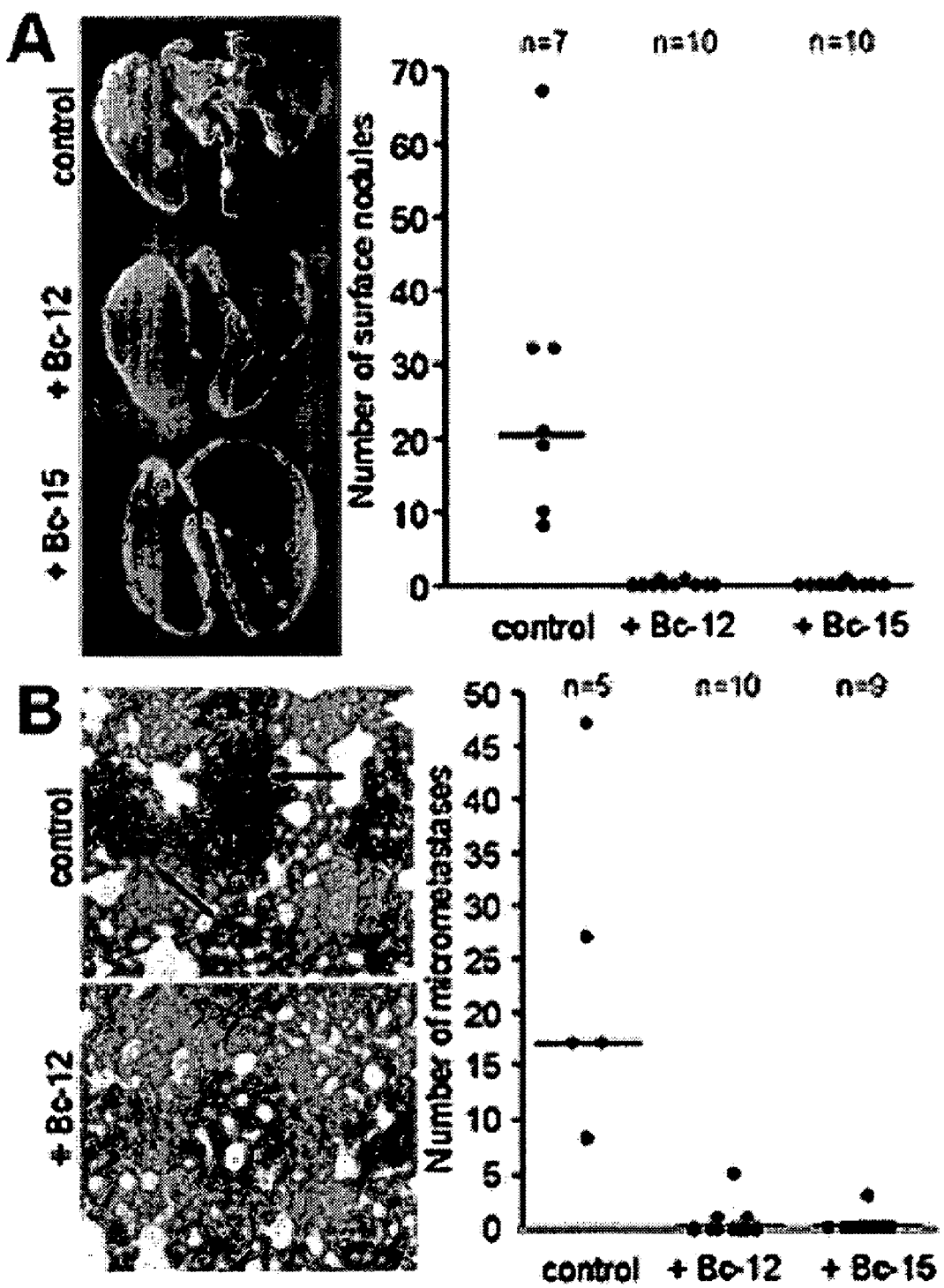
FIGS. 5A, 5B, 5C. ScFvs Bc-12 and Bc-15 prevent hematogenous breast cancer metastasis. (A) Left: Lungs of female SCID mice 32 days after i.v. injection with $1\times10^5$ BMS human breast cancer cells. The mice were treated with 50 μg Bc-12 or Bc-15 in 100 μl PBS (i.v.) on days 1, 2, 3 and 4. Controls received PBS only. Right: Numbers of lung surface metastases for each animal, horizontal lines indicate the median number of metastases per group. ScFv treated mice had significantly fewer metastases (P<0.001 by the Kruskal Wallis Test). (B) Left: Histological sections of the above mouse lungs, stained with hematoxylin/eosin. Metastases were counted in six sets of three consecutive sections separated by 140 μm for each lung. Right: Number of metastases counted in sections of individual lungs, horizontal lines indicate median number of metastases per animal group. ScFv treated mice had significantly fewer detectable metastases (P<0.005 by the Kruskal Wallis Test). (C) Effect of Bc-15 treatment on established breast cancer metastasis in the lungs. Female SCID mice were injected i.v. with $5\times10^5$ DsRed2-tagged MDA-MB 435 breast cancer cells expressing constitutively activated integrin $\alpha v\beta 3_{D723R}$. Mice were treated on day 7, 9, 11 and 14, 16, 18 by i.v. injections of scFv Bc-15 or its RGE mutant, Mut-15 (40 μg/dose). Metastatic foci were enumerated by fluorescence microscopy on day 19. Left: Images of typical tumor foci within the lung tissue in Mut-15 (top) or Bc-15 treated mice (bottom) (bar: 50 μm). Right: Number of metastatic foci within the lung tissue of each animal, horizontal line: median number of metastases per group. Bc-15 treated mice had significantly fewer metastases than mice treated with Mut-15 (P<0.001 by the two-sided Mann-Whitney rank sum Test).
Figure 5C:
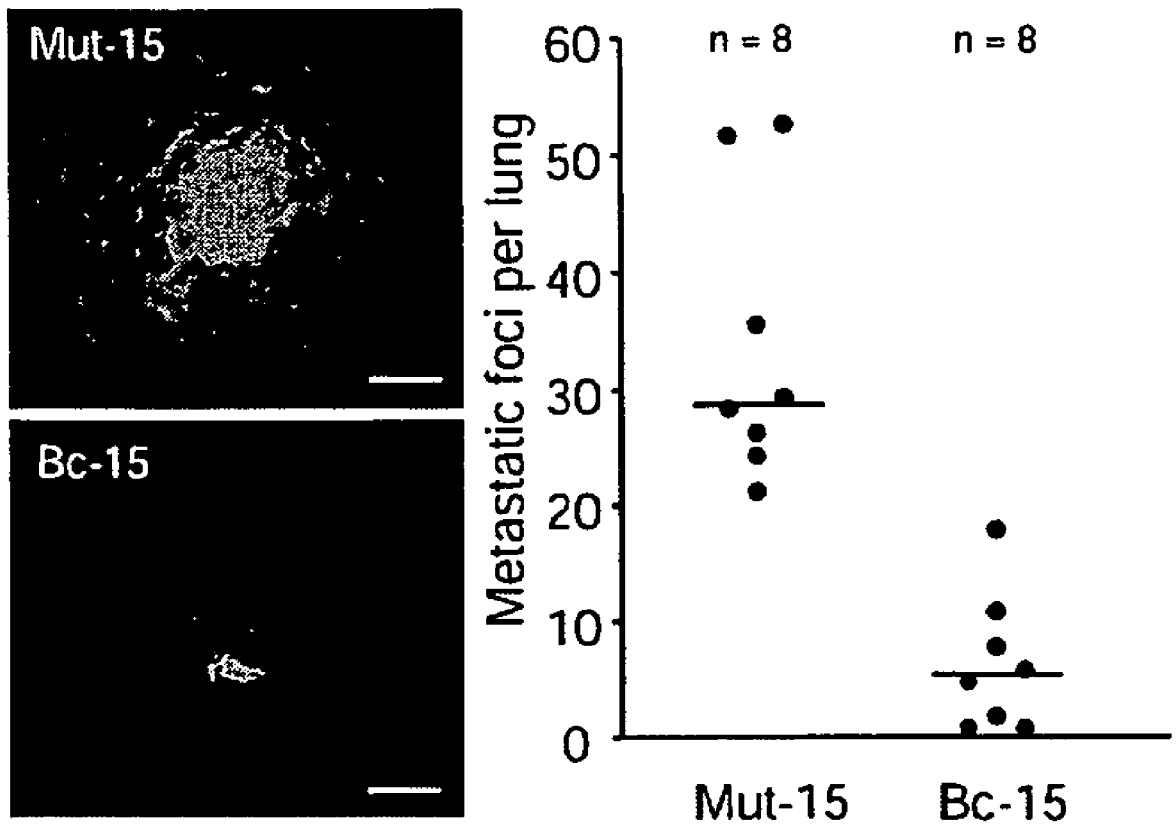
Figure 6:
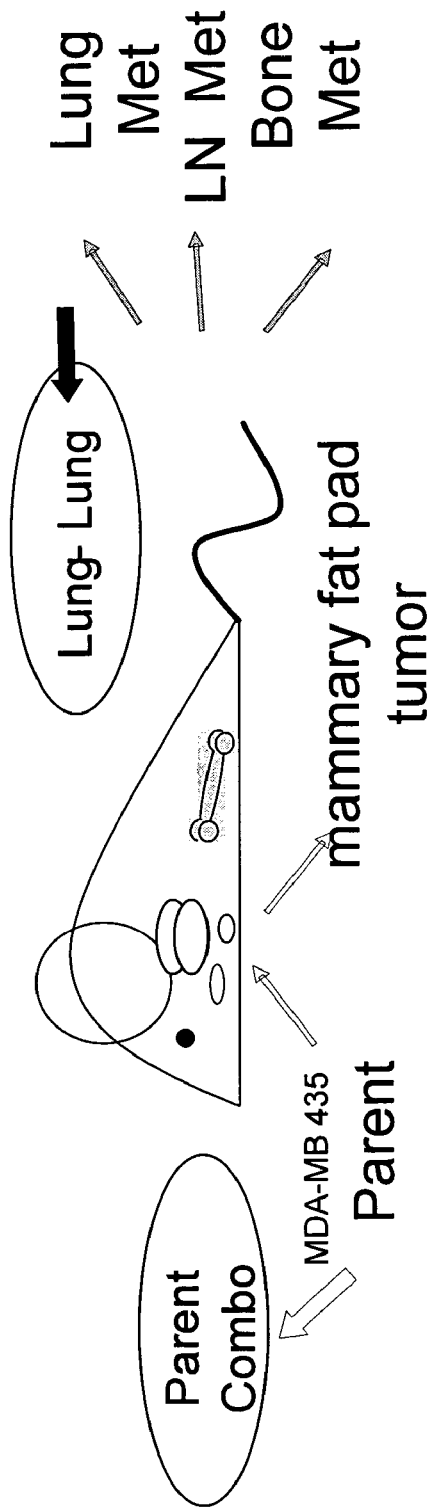
FIG. 6. αvβ3 integrin receptor expression in parental cell and tumor cell variants.
Figure 7:
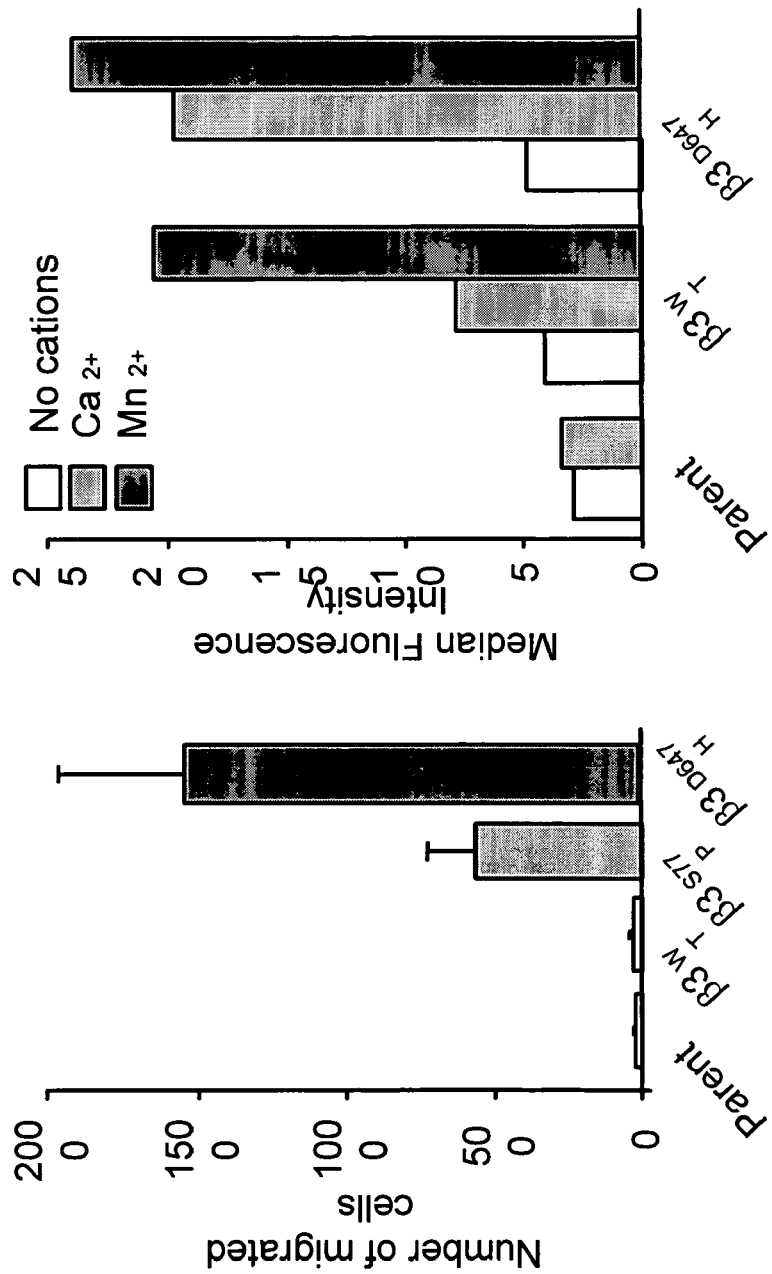
FIG. 7. scFvs Bc-12 and Bc-15 react with tumor cells expressing gain-of-function mutants of β3 found in metastatic breast cancer cells.
Figure 8:
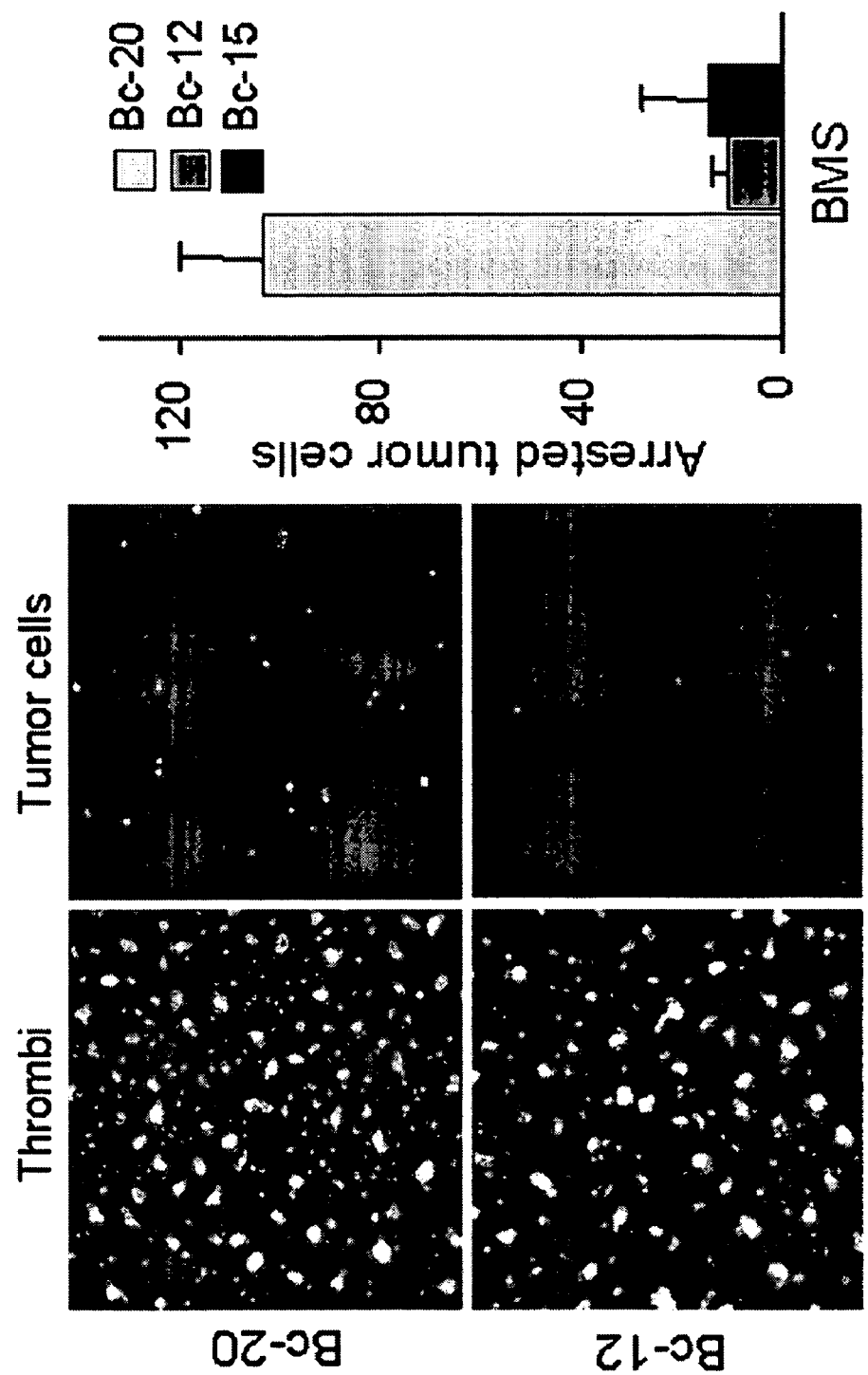
FIG. 8. scFvs Bc-12 and Bc-15 inhibit platelet mediated breast cancer cell arrest during blood flow.

To test directly whether targeting activated integrin αvβ3 with the ligand mimetic antibodies Bc-12 and-15 affects target organ colonization by circulating metastatic breast cancer cells, $1 \times 10^5$ BMS human breast cancer cells were injected intravenously into female C.B-17 SCID mice, together with 50 μg sterile, endotoxin free preparations of Bc-12 or Bc-15 (n=8-10 mice per group). At an average blood volume of 2 ml per mouse, this provides an initial scFv concentration of 1 μM. The clearance time for scFv antibody fragments in the circulation is less than 1 h. Kortt et al., *Biomol. Eng,* 18: 95-108, 2001. Tumor cells may remain in the circulation for several days. Therefore, scFv antibody injections (50 μg bolus doses, i.v.) were repeated on the second, third and fourth day. Antibody treated and control mice appeared healthy during the experiment. After 32 days, the mice were euthanized, dissected and analyzed by gross examination. No obvious abnormalities were observed. The lungs were excised, fixed, and metastatic foci counted at the lung surface. Each of the control treated mice had tumor foci on their lungs (range: 8 to 68 foci per lung). In stark contrast, only two animals in the Bc-12 treated group, and 1 animal in the Bc-15 treated group had one visible nodule at their lung surface (FIG. 5A). Similar results were obtained in a second experiment under more challenging conditions, using a higher cell dose and a different breast cancer cell type ($3 \times 10^5$ BCM1 cells/mouse).

To analyze whether scFv treatment had reduced or actually prevented metastatic colonization of the lung tissue, the lungs of each mouse were embedded in paraffin, sectioned, stained with hematoxylin/eosin, and examined histologically for evidence of metastatic colonies within the lung tissue. Per lung, six sets of three consecutive sections, separated by 140 μm, were collected. The sections were randomized and coded, and the total number of metastatic foci counted. All control animals had metastases in their lung tissues (range: 7 to 48 counts per lung), and those were of considerable size (FIG. 5B top image). In contrast, only 3 of 10 Bc-12 treated mice and 1 of 9 Bc-15 treated mice had microscopically detectable metastases in their lung tissue (range: 0 to 5 counts per lung) (FIG. 5B). Thus, injections with scFv Bc-12 or Bc-15 interfered with lung colonization by circulating breast cancer cells at a statistically significant level ($P<0.005$).

Taken together, the data imply that the circulating immune repertoire of at least some cancer patients contains antibodies against the activated form of integrin αvβ3. By amplifying these naturally occurring antibodies in vitro, their specificity and potential have been demonstrated for disrupting critical functions of circulating metastatic cells thereby inhibiting breast cancer metastasis in vivo. The next clinically relevant question will be whether targeting the activated form of αvβ3 can interfere with established breast tumors and ongoing spontaneous metastasis. This seems plausible since metastatic cells as well as tumor supporting angiogenic endothelial cells apparently bypass the normal control of adhesive, migratory and invasive properties by expressing constitutively activated integrin αvβ3. Felding-Habermann et al., *Proc. Natl. Acad. Sci. U.S.A* 98: 1853-1858, 2001; Kiosses et al., *Nat. Cell Biol.* 3: 316-320, 2001.

Example 5

Diagnosis, Prognosis and Treatment of Metastatic Cancer in a Mammalian Subject

These studies have shown that combinatorial antibody libraries of cancer patients contain antibodies with disease fighting potential. The studies have demonstrated that such antibodies can be isolated in vitro and that these antibodies can be used to inhibit metastasis in an experimental animal model. Based on this finding, one might expect a high frequency of similar antibodies with disease fighting potential in antibody libraries from patients who are long-term survivors of metastatic cancer. Such libraries can be generated and mined for the presence of such antibodies.

The present invention addresses diagnostic, prognostic and therapeutic approaches that can prevent breast cancer disease from becoming systemic. The present invention provides a further understanding of how to design and test drugs to treat metastases. Metastases are ultimately responsible for much of the suffering and mortality from breast cancer. The present invention addresses this need to identify and target molecular and functional markers that identify metastatic breast cancer cells and to generate therapeutic reagents for their specific inhibition.

Combinatorial antibody libraries can be isolated using antibody phage display technology and subtractive panning and screening strategy. Human tumor cell models of metastatic tumor cells are generated, for example, neoplastic tumors, solid tumor, breast cancer, hematological malignancy, leukemia, colorectal cancer, uterine cancer, uterine leiomyomas, ovarian cancer, endometrial cancer, polycystic ovary syndrome, endometrial polyps, prostate cancer, prostatic hypertrophy, pituitary cancer, adenomyosis, adenocarcinomas, meningioma, melanoma, bone cancer, multiple myeloma, CNS cancer, glioma, or astroblastoma.

Breast cancers are known to be extremely heterogeneous. The present invention has demonstrated that a subset of human breast cancer cells can be identified based on expression of an adhesion receptor, the integrin αvβ3, in its constitutively activated functional form. This activated integrin promotes platelet binding and tumor cells arrest in the vasculature. In this way, activation of integrin αvβ3 endows metastatic cells with key properties likely to be critical for successful dissemination and colonization of target organs. The combined immune repertoire of a number of cancer patients has been mined using antibody phage display technology by subtractive panning on poorly versus strongly metastatic variants of a human breast cancer cell line. This approach yielded single chain Fv (scFv) antibodies that specifically recognize the activated functional conformation of the tumor cell adhesion receptor, integrin αvβ3. The antibodies react selectively with metastatic variants of the breast cancer cell models described herein and with metastatic cells isolated from blood samples of stage IV breast cancer patients. These antibodies inhibit colonization of the lungs by human breast cancer cells in immune deficient mice.

Studies will investigate the ability of human single chain Fv (scFv) antibodies to report the activated form of integrin αvβ3 as a diagnostic marker of metastatic breast cancer cells. The scFv antibodies and their derivatives are useful to specifically detect metastatic breast cancer cells and report the localization of metastatic disease.

Studies will investigate the ability of human single chain Fv (scFv) antibodies to report the activated form of integrin αvβ3 as a prognostic marker of metastatic breast cancer. The scFv antibodies and their derivatives are useful to specifically detect breast cancer cells that have a propensity to metastasize.

Studies will analyze effects of human scFv antibodies and their derivatives against constitutively activated integrin αvβ3 on breast cancer metastasis. Targeted inhibition of cells expressing the activated form of integrin αvβ3 are useful to prevent breast cancer metastasis and interfere with established metastatic disease.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed:

1. An isolated antibody which specifically binds to an activated αvβ3 integrin receptor which is differentially produced on a cell in a metastatic state compared to a non-metastatic cell, said antibody comprising SEQ ID NO: 2.

2. The antibody of claim 1, wherein said metastatic cell targets to a tissue selected from breast, brain, lung, liver, or bone.

3. A pharmaceutical composition comprising said antibody of claim 1.

4. The antibody of claim 1, wherein the antibody is a ligand mimetic.

5. The antibody of claim 1 consisting of SEQ ID NO: 2.

6. A method for treating cancer in a mammal comprising administering to the mammal an isolated antibody which specifically binds to an activated αvβ3 integrin receptor which is differentially produced on a cell in a metastatic state as compared to a non-metastatic cell, said anitbody comprising SEQ ID NO: 2.

7. The method of claim 6, wherein the cancer is breast cancer metastasis in said mammal.

8. The method of claim 6, said antibody consisting of SEQ ID NO: 2.

* * * * *

UNITED STATES PATENT AND TRADEMARK OFFICE
CERTIFICATE OF CORRECTION

| | | |
|---|---|---|
| PATENT NO. | : 7,271,245 B2 | Page 1 of 1 |
| APPLICATION NO. | : 11/056825 | |
| DATED | : September 18, 2007 | |
| INVENTOR(S) | : Felding-Habermann et al. | |

It is certified that error appears in the above-identified patent and that said Letters Patent is hereby corrected as shown below:

Column 1, lines 14-19. Delete the paragraph in its entirety and insert therefor

-- A portion of the work described herein was supported by grant numbers Al 47127, CA 95458, and M01 RR 00833 from the National Institutes Of Health, and DAMD 17-99-1-9368 from the U.S. Army Breast Cancer Research Program. The United States Government has certain rights in this invention. --

Signed and Sealed this

Sixth Day of May, 2008

JON W. DUDAS
*Director of the United States Patent and Trademark Office*